(12) United States Patent
Hattori et al.

(10) Patent No.: US 8,143,274 B2
(45) Date of Patent: Mar. 27, 2012

(54) 1-(2H)-ISOQUINOLONE DERIVATIVE

(75) Inventors: Kazuo Hattori, Kanagawa (JP); Satoshi Niizuma, Kanagawa (JP); Takehiro Okada, Kanagawa (JP); Hiroyuki Eda, Kanagawa (JP); Kenji Tatsuno, Kanagawa (JP); Miyuki Yoshida, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 823 days.

(21) Appl. No.: 10/588,611

(22) PCT Filed: Feb. 7, 2005

(86) PCT No.: PCT/JP2005/001764
§ 371 (c)(1),
(2), (4) Date: Aug. 7, 2006

(87) PCT Pub. No.: WO2005/075431
PCT Pub. Date: Aug. 18, 2005

(65) Prior Publication Data
US 2007/0185160 A1 Aug. 9, 2007

(30) Foreign Application Priority Data
Feb. 6, 2004 (JP) .................................. 2004-30885

(51) Int. Cl.
C07D 217/24 (2006.01)
A61K 31/47 (2006.01)
(52) U.S. Cl. .......................................... 514/309; 546/141
(58) Field of Classification Search ........................ None
See application file for complete search history.

(56) References Cited

U.S. PATENT DOCUMENTS
4,942,163 A 7/1990 Behrens

FOREIGN PATENT DOCUMENTS
WO WO 98/51307 11/1998
WO WO 99/11624 A1 3/1999

OTHER PUBLICATIONS

Izumi et al, Journal of Heterocyclic Chemistry (1994), 31(1), pp. 145-152.*
Wu et al., Toxicology, 236, pp. 1-6, 2007.*
Noboru Yagi et al., "Syntheses of N-Substituted-7-acylamino-3-phenylisocarbostyril and 6-Phenylbenzimidazo[2,1-a]-isoquinoline Derivatives and their Fluorescence Spectra", *Yuki Gosei Kagaku Kyokaishi*, vol. 27, pp. 51-58, 1969.
Won-Jea Cho et al., "Synthesis and Biological Evaluation of 3-Arylisoquinolines As Antitumor Agents", *Bioorganic & Medical Chemistry Letters*, vol. 8, pp. 41-46, 1998.
Alain Rose et al., "Oxygen Heterocycles. Part XIII. From 3-Arylisoquinolines and 4-Aryl-5H-2,3-benzodiazepines", *J. Chem. Soc.*, (C), 1968, pp. 2205-2208.
Graham S. Poindexter, "Convenient Preparation of 3-Substituted 1(2H)-Isoquinolinones", *J. Org. Chem.*, vol. 47, pp. 3787-3788, 1982.
Won-Jea Cho et al., "Synthesis and Antitumor Activity of 3-Arylisoquinoline Derivatives", *Arch. Pharm. Res.*, vol. 20, No. 3, pp. 264-268, 1997.
Seung Hoon Cheon et al., "Structure-Activity Relationship Studies of Isoquinolinone Type Anticancer Agent", *Arch. Pharm. Res.*, vol. 24, No. 4, pp. 276-280, 2001.
Won-Jea Cho et al., "Molecular Modeling of 3-Arylisoquinoline Antitumor Agents Active Against A-549. A Comparative Molecular Field Analysis Study", *Bioorganic & Medical Chemistry Letters*, vol. 10, pp. 2953-2961, 2002.
Thanh Nguyen Le et al., "A facile synthesis of benzo[c]phenanthridine alkaloids: oxynitidine and oxysanguinarine using lithiated toluamide-benzonitrile cycloaddition", *Tetrahedron Letters*, vol. 45, pp. 2763-2766, 2004.
Thanh Nguyen Le et al., "A Versatile Total Synthesis of Benzo[c]phenanthridine and Protoberberine Alkaloids Using Lithiated Toluamide-Benzonitrile Cycloaddition", *J. Org. Chem.*, vol. 69, pp. 2768-2772, 2004.
John P. Wolfe et al, "Simple, Efficient Catalyst System for the Palladium-Catalyzed Amination of Aryl Chlorides, Bromides, and Triflates", *J. Org. Chem.*, vol. 65, pp. 1158-1174, 2000.

(Continued)

*Primary Examiner* — Zinna Northington Davis
(74) *Attorney, Agent, or Firm* — Browdy and Neimark, PLLC

(57) ABSTRACT

The present invention provides: a compound represented by the following formula (I):

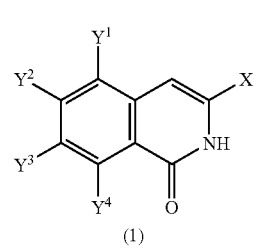

[Formula 1]

(1)

[wherein $Y^1$ and $Y^4$ represent a hydrogen atom or a halogen atom; either one of $Y^2$ and $Y^3$ represents —$NR^1R^2$, and the other represents a hydrogen atom or a halogen atom; X represents an aryl group or a heteroaryl group that may be substituted; $R^1$ represents a hydrogen atom, or a $C_{1-8}$ alkyl group that may be substituted; and $R^2$ represents a $C_{1-8}$ alkyl group that is substituted with one or more substituents, —$COOR^3$, —$COR^4$, —$COSR^5$, —$CONR^6R^7$, —$NR^{22}R^{23}$, or —C=$NR^{24}R^{25}$; or $R^1$ and $R^2$, together with a nitrogen atom to which they are bonded, may form a 4- to 10-membered hetero ring containing at least one nitrogen atom (wherein the hetero ring may be substituted with one or more substituents selected from Group C)], a prodrug thereof, or a pharmaceutically acceptable salt thereof; and a pharmaceutical, a pharmaceutical composition, or the like, which comprises the compound.

21 Claims, No Drawings

OTHER PUBLICATIONS

Michele C. Harris et al., "Improved Functional Group Compatibility in the Palladium-Catalyzed Synthesis of Aryl Amines", *Organic Letters*, vol. 4, No. 17, pp. 2885-2888, 2002.

Xiaohua Huang et al., "New Ammonia Equivalents for the Pd-Catalyzed Amination of Aryl Halides", *Organic Letters*, vol. 3, No. 21, pp. 3417-3419, 2001.

Kentaro Okano et al., "Synthesis of Secondary Arylamines through Copper-Mediated Intermolecular Aryl Amination", *Organic Letters*, vol. 5, No. 26, pp. 4987-4990, 2003.

Artis Klapars et al., "A General and Efficient Copper Catalyst Arylation for the Amidation of Aryl Halides and the *N*-Arylation of Nitrogen Heterocycles", *J. Am. Chem. Soc.*, vol. 123, pp. 7727-7729, 2001.

Artis Klapars et al., "A General and Efficient Copper Catalyst for the Amidation of Aryl Halides", *J. Am. Chem. Soc.*, vol. 124, pp. 7421-7428, 2002.

Teruo Umemoto et al., "Synthesis, Properties, and Reactivity of *N,N*-Difluoribipyridinium and Related Salts and their Applications as Reactive and Easy-to-Handle Electrophilic Fluorinating Agents with High Effective Flourine Content", *J. Org. Chem.*, vol. 63, pp. 3379-3385, 1998.

J. Hodge Markgraf et al., :Strained Heterocyclic Systems. 16. 1-Azatriptycene, *Heterocycles*, vol. 29, No. 4, pp. 649-651, 1989.

Fujio et al., "Preparation of fused heterocyclic compounds such as 2H-isoquinolin-I-one and 3H-quinazolin-4-one derivatives as poly(ADP-ribose) polymerase inhibitors and medicinal use thereof", WO021094790 A1 (Nov. 28, 2002), Abstract (See attached Supplementary European Search Report dated Sep. 16, 2009).

Hattori et al., "Preparation of 2H-isoquinolin-l-one derivatives and use thereof as anticancer agents", W020051075432 A1 (Aug. 18,2005) (See attached Supplementary European Search Report dated Sep. 16, 2009).

Izumi T., "Synthesis of Isocoumarin. 1-Isoquinolone and 4 (IH) -Quinolone Derivatives via Seleno-intermediates", Journal of Heterocyclic Chemistry, 1994, vol. 31, No. 1, pp. 145-152 (English language translation provided).

Office Action in the Japanese Patent Office in Japanese Patent 2005-517767 on Mar. 10, 2011.

\* cited by examiner

1-(2H)-ISOQUINOLONE DERIVATIVE

CONTINUING DATA

This application is a 371 of PCT/JP05/01764 filed Feb. 7, 2005.

TECHNICAL FIELD

The present invention relates to a novel 1-(2H)-isoquinolone derivative and a pharmaceutical comprising the same as an active ingredient. The present invention particularly relates to an antitumor agent useful as a therapeutic agent for diseases such as solid cancer.

BACKGROUND ART

Regarding a method for synthesizing a 1-(2H)-isoquinoline derivative having a substituent at the 3-position, several reports have already been made. For example, in 1968, Rose et al. have reported a method of allowing ammonia to act on a 3-aryl isocoumarin derivative, so as to synthesize a 1-(2H)-isoquinolone derivative (refer to Non-Patent Document 1). In addition, in 1982, Poindexter has reported a method of synthesizing a 1-(2H)-isoquinolone derivative by the reaction of N,2-dimethylbenzamide with a nitrile derivative (refer to Non-Patent Document 2).

Moreover, the pharmacological activity of such an isoquinolone derivative has also been reported. Researchers of Octamer have reported an isoquinolone derivative having anti-inflammatory action (refer to Patent Document 1). Also, researchers of Guilford have reported that 3-phenyl-1-(2H)-isoquinolone has an inhibitory activity on poly(ADP-ribose) polymerase, and that it is used as a radiosensitizer (refer to Patent Document 3). Moreover, with regard to an isoquinolone derivative having anticancer action, in 1989, researchers of Du Pont have reported that a 3-(1-naphthyl)-1-(2H)-isoquinolone derivative exhibits anticancer action (refer to Patent Document 2). Thereafter, Won-Jea Cho et al. have reported a 3-aryl isoquinolone derivative having anticancer action (refer to Non-Patent Documents 3 to 8). However, the anticancer activities of such isoquinolone derivatives have not been necessarily sufficient. Thus, it has been desired that a compound having higher anticancer activity and also having preferred physical properties be developed.

[Patent Document 1] International Publication WO98/51307
[Patent Document 2] U.S. Pat. No. 4,942,163
[Patent Document 3] International Publication WO99/11624
[Non-Patent Document 1] J. Chem. Soc. (C), pp. 2205-2208 (1968)
[Non-Patent Document 2] J. Org. Chem., vol. 47, pp. 3787-3788 (1982)
[Non-Patent Document 3] Arch. Pharm. Res., vol. 20, pp. 264-268 (1997)
[Non-Patent Document 4] Bioorg. Med. Chem. Lett., vol. 8, pp. 41-46 (1998)
[Non-Patent Document 5] Arch. Pharm. Res., vol. 24, pp. 276-280 (2001)
[Non-Patent Document 6] Bioorg. Med. Chem., vol. 10, pp. 2953-2961 (2002)
[Non-Patent Document 7] Tetrahedron Lett., vol. 45, pp. 2763-2766 (2004)
[Non-Patent Document 8] J. Org. Chem., vol. 69, pp. 2768-2772 (2004)

DISCLOSURE OF THE INVENTION

Problems to be Solved by the Invention

It is an object of the present invention to provide a compound, which has high antitumor activity and is useful as a therapeutic and preventive agent effective for proliferative diseases such as cancer, a production method thereof, an intermediate compound useful for such production, and a pharmaceutical composition comprising such a compound.

Means for Solving the Problems

The present inventors have conducted intensive studies directed towards providing a novel therapeutic and preventive agent, which is effective for proliferative diseases such as cancer. As a result, the inventors have found that the compound of the present invention has excellent antitumor activity, thereby completing the present invention.

That is to say, an aspect of the present invention provides a compound represented by the following formula (1):

[Formula 1]

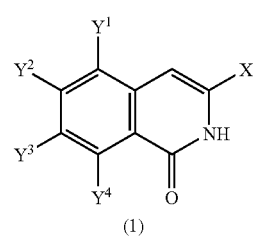

(1)

[wherein, $Y^1$ and $Y^4$ are independently selected from a hydrogen atom and a halogen atom, either one of $Y^2$ and $Y^3$ represents $-NR^1R^2$, and the other represents a hydrogen atom or a halogen atom;

X represents an aryl group or a heteroaryl group, and the aryl group or heteroaryl group may be substituted with one or more substituents selected from Group A;

Group A consists of a $C_{1-8}$ alkyl group (wherein the alkyl group may be substituted with one or more substituents selected from a halogen atom, an aryl group, a heteroaryl group, $-OR^{11}$, and $-NR^{12}R^{13}$), a $C_{2-7}$ alkenyl group (wherein the $C_{2-7}$ alkenyl group may be substituted with one or more substituents selected from a halogen atom, a $C_{1-8}$ alkyl group, an aryl $C_{1-6}$ alkyl group, an aryl group, and a heteroaryl group), a $C_{2-7}$ alkynyl group (wherein the $C_{2-7}$ alkynyl group may be substituted with one or more substituents selected from a halogen atom, a $C_{1-8}$ alkyl group, an aryl $C_{1-6}$ alkyl group, an aryl group, and a heteroaryl group), a halogen atom, a hydroxyl group, an aryl group, a heteroaryl group, a cyano group, an amino group (wherein the nitrogen atom of the amino group may be substituted with one or two substituents selected from a $C_{1-8}$ alkyl group, which may be substituted with $-OR^{11}$ or $-NR^{12}R^{13}$, an aryl group, an aryl $C_{1-6}$ alkyl group, and a heteroaryl group), $-S(O)_nR^{14}$ (wherein n represents an integer between 0 and 2), a $C_{1-6}$ alkoxy group (wherein the alkoxy group may be substituted with one or more groups selected from an aryl group, a heteroaryl group, $-OR^{11}$, $-NR^{12}R^{13}$, and a halogen atom), a 4- to 7-membered hetero ring group (wherein the hetero ring group may be substituted with one or more substituents selected from Group D), an aryloxy group, a heteroaryloxy group, and a $C_{1-6}$ alkylenedioxy group; wherein $R^{11}$, $R^{12}$, $R^{13}$, and $R^{14}$ are independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an amino group, a $C_{1-6}$ alkylamino group, a di($C_{1-6}$ alkyl)amino group, an aryl group, and a heteroaryl group), an aryl group, and a heteroaryl group; or $R^{12}$ and $R^{13}$, together with nitrogen to which they are bonded, may form a 4- to 7-membered hetero ring containing at least one nitrogen atom;

$R^1$ represents a hydrogen atom, or a $C_{1-8}$ alkyl group that may be substituted with one or more substituents selected from Group B;

$R^2$ represents a $C_{1-8}$ alkyl group that is substituted with one or more substituents selected from Group B, —COOR³, —COR⁴, COSR⁵, CONR⁶R⁷, —NR²²R²³, or —N=CR²⁴R²⁵; or $R^1$ and $R^2$, together with a nitrogen atom to which they are bonded, may form a 4- to 10-membered hetero ring containing at least one nitrogen atom (wherein the hetero ring may be substituted with one or more substituents selected from Group C); wherein $R^3$ represents a hydrogen atom, a $C_{1-8}$ alkyl group, a $C_{2-7}$ alkenyl group, a $C_{2-7}$ alkynyl group (wherein the alkyl group, alkenyl group, and alkynyl group may be substituted with one or more substituents selected from a halogen atom, a hydroxyl group, a $C_{1-6}$ alkoxy group (wherein the alkoxy group may be substituted with one or more substituents selected from a hydroxyl group, a $C_{1-6}$ alkoxy group, and a phenyl group), a $C_{3-8}$ cycloalkyl group, an aryl group, and a heteroaryl group), a $C_{3-8}$ cycloalkyl group, an aryl group, or a heteroaryl group;

$R^4$ is selected from a hydrogen atom, a $C_{1-8}$ alkyl group that may be substituted with one or more $R^{20}$s, an aryl group, and a heteroaryl group;

$R^5$ is selected from a hydrogen atom, a $C_{1-8}$ alkyl group, an aryl group, and a heteroaryl group;

$R^{20}$ represents a hydroxyl group, a halogen atom, an aryl group, a heteroaryl group, a $C_{1-6}$ alkoxy group (wherein the alkoxy group may be substituted with one or more substituents selected from a halogen atom, an aryl group, and a heteroaryl group), an aryloxy group, a heteroaryloxy group, an amino group (wherein the nitrogen atom of the amino group may be substituted with one or two substituents selected from a $C_{1-8}$ alkyl group, an aryl group, an aryl $C_{1-6}$ alkyl group, a heteroaryl group, and —COOR²¹), or a 4- to 7-membered hetero ring group containing at least one nitrogen atom (wherein the hetero ring group may be substituted with a $C_{1-8}$ alkyl group);

$R^{21}$ represents a $C_{1-8}$ alkyl group, an aryl $C_{1-6}$ alkyl group, or an aryl group;

$R^6$ and $R^7$ are independently selected from a hydrogen atom, a $C_{1-8}$ alkyl group, an aryl group, and a heteroaryl group;

$R^{22}$ and $R^{23}$ are independently selected from a hydrogen atom, a $C_{1-8}$ alkyl group, an aryl group, and a heteroaryl group;

$R^{24}$ and $R^{25}$ are independently selected from a hydrogen atom, a $C_{1-8}$ alkyl group, an aryl group, and a heteroaryl group;

Group B consists of a halogen atom, a $C_{1-6}$ alkylcarbonyl group, a $C_{1-6}$ alkylaminocarbonyl group, a $C_{1-6}$ alkoxycarbonyl group, an aryl group (wherein the aryl group may be substituted with one or more substituents selected from a halogen atom, a $C_{1-8}$ alkyl group, a $C_{1-8}$ haloalkyl group, a hydroxyl group, a $C_{1-6}$ alkoxy group, and a $C_{1-6}$ haloalkoxy group), a heteroaryl group, —OR³¹, and —NR³²R³³; wherein $R^{31}$, $R^{32}$, and $R^{33}$ are independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an aryl group, an amino group, a $C_{1-6}$ alkylamino group, and a di($C_{1-6}$ alkyl)amino group), an aryl group, a heteroaryl group, and —COOR³⁴; wherein $R^{34}$ represents a $C_{1-8}$ alkyl group, an aryl $C_{1-6}$ alkyl group, or an aryl group; or $R^{32}$ and $R^{33}$, together with a nitrogen atom to which they are bonded, may form a 4- to 7-membered hetero ring containing at least one nitrogen atom (wherein the hetero ring group may be substituted with one or more groups selected from Group D);

Group C consists of an aryl group, a heteroaryl group, a $C_{1-6}$ alkylcarbonyl group, a $C_{1-6}$ alkylaminocarbonyl group, a $C_{1-6}$ alkoxycarbonyl group, a hydroxyl group, a $C_{1-8}$ alkyl group, a $C_{1-6}$ alkoxy group (wherein the alkyl group and alkoxy group may be substituted with one or more substituents selected from a halogen atom, an aryl group, a heteroaryl group, —NR⁴¹R⁴², and —OR⁴³), an aryloxy group, and a heteroaryloxy group; wherein $R^{41}$, $R^{42}$, and $R^{43}$ are independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an amino group, a $C_{1-6}$ alkylamino group, and a di($C_{1-6}$ alkyl) amino group), an aryl $C_{1-6}$ alkyl group, an aryl group, and a heteroaryl group; or $R^{41}$ and $R^{42}$, together with a nitrogen atom to which they are bonded, may form a 4- to 7-membered hetero ring containing at least one nitrogen atom; and Group D consists of a halogen atom, an aryl group, a heteroaryl group, an aryloxy group, a heteroaryloxy group, an amino group (wherein the nitrogen atom of the amino group may be substituted with one or two substituents selected from a $C_{1-8}$ alkyl group, a hydroxy $C_{1-6}$ alkyl group, a $C_{1-6}$ alkoxy $C_{1-6}$ alkyl group, a $C_{1-6}$ alkylamino $C_{1-6}$ alkyl group, a di($C_{1-6}$ alkyl)amino $C_{1-6}$ alkyl group, an aryl group, an aryl $C_{1-6}$ alkyl group, and a heteroaryl group), a hydroxyl group, a $C_{1-6}$ alkoxy group (wherein the alkoxy group may be substituted with one or more substituents selected from a halogen atom, a hydroxyl group, a $C_{1-6}$ alkoxy group, a $C_{1-6}$ alkylamino group, and di($C_{1-6}$ alkyl)amino group), a $C_{1-6}$ alkoxycarbonyl group, a $C_{1-8}$ alkyl group (wherein the alkyl group may be substituted with one or more substituents selected from a halogen atom, a hydroxyl group, a $C_{1-6}$ alkoxy group, a $C_{1-6}$ alkoxycarbonyl group, an amino group, an aryl group, a heteroaryl group, a $C_{1-6}$ alkylamino group, and a di($C_{1-6}$ alkyl) amino group)], a prodrug thereof, or a pharmaceutically acceptable salt thereof.

Another aspect of the present invention provides the compound represented by the above formula (1), the prodrug thereof, or the pharmaceutically acceptable salt thereof, wherein $Y^3$ represents —NR¹R².

A further aspect of the present invention provides the compound represented by the above formula (1), the prodrug thereof, or the pharmaceutically acceptable salt thereof, wherein $Y^1$, $Y^2$, and $Y^4$ represent a hydrogen atom;

$Y^3$ represents —NR¹R²;

X represents an aryl group or a heteroaryl group, and the aryl group may be substituted with one or more substituents selected from Group A;

Group A consists of a $C_{1-8}$ alkyl group (wherein the alkyl group may be substituted with one or more substituents selected from a halogen atom and —$NR^{12}R^{13}$), a halogen atom, a hydroxyl group, an aryl group, an amino group (wherein the nitrogen atom of the amino group may be substituted with one or two substituents selected from a $C_{1-8}$ alkyl group and an aryl group), —$SR^{14}$, a $C_{1-6}$ alkoxy group (wherein the alkoxy group may be substituted with one or more groups selected from —$OR^{11}$ and a halogen atom), and a 4- to 7-membered hetero ring group (wherein the nitrogen atom of the hetero ring group may be substituted with one or two substituents selected from a $C_{1-8}$ alkyl group and a $C_{1-6}$ alkoxycarbonyl group); wherein $R^{11}$, $R^{12}$, $R^{13}$, and $R^{14}$ are independently selected from a hydrogen atom, a $C_{1-8}$ alkyl group, and an aryl group; or $R^{12}$ and $R^{13}$, together with nitrogen to which they are bonded, may form a 4- to 7-membered hetero ring containing at least one nitrogen atom;

$R^1$ represents a hydrogen atom, or a $C_{1-8}$ alkyl group that may be substituted with one or more substituents selected from Group B;

$R^2$ represents a $C_{1-8}$ alkyl group that is substituted with one or more substituents selected from Group B, —$COOR^3$, —$COR^4$, —$COSR^5$, —$CONR^6R^7$, —$NR^{22}R^{23}$, or —$N=CR^{24}R^{25}$; or $R^1$ and $R^2$, together with a nitrogen atom to which they are bonded, may form a 4- to 10-membered hetero ring containing at least one nitrogen atom (wherein the hetero ring may be substituted with one or more substituents selected from Group C); wherein $R^3$ represents a $C_{1-8}$ alkyl group (wherein the alkyl group may be substituted with one or more substituents selected from a halogen atom, a hydroxyl group, a $C_{1-6}$ alkoxy group (wherein the alkoxy group may be substituted with one or more substituents selected from a hydroxyl group, a $C_{1-6}$ alkoxy group, and a phenyl group), a $C_{3-8}$ cycloalkyl group, an aryl group, and a heteroaryl group), a $C_{2-7}$ alkenyl group, a $C_{2-7}$ alkynyl group, a $C_{3-8}$ cycloalkyl group, an aryl group, or a heteroaryl group;

$R^4$ is selected from a hydrogen atom, a $C_{1-8}$ alkyl group that may be substituted with one or more $R^{20}$s, an aryl group, and a heteroaryl group, and $R^5$ is selected from a $C_{1-8}$ alkyl group and an aryl group;

$R^{20}$ represents a hydroxyl group, a halogen atom, an aryl group, a heteroaryl group, a $C_{1-6}$ alkoxy group, an aryloxy group, an aryl $C_{1-6}$ alkoxy group, an amino group (wherein the nitrogen atom of the amino group may be substituted with one or two substituents selected from a $C_{1-8}$ alkyl group, an aryl group, and —$COOR^{21}$), or a 4- to 7-membered hetero ring group containing at least one nitrogen atom (wherein the hetero ring group may be substituted with a $C_{1-8}$ alkyl group);

$R^{21}$ represents a $C_{1-8}$ alkyl group, an aryl $C_{1-6}$ alkyl group, or an aryl group;

$R^6$ and $R^7$ are independently selected from a hydrogen atom, a $C_{1-8}$ alkyl group, and an aryl group;

$R^{22}$, $R^{23}$, $R^{24}$, and $R^{25}$ are independently selected from a hydrogen atom, a $C_{1-8}$ alkyl group, an aryl group, and a heteroaryl group;

Group B consists of a halogen atom, a $C_{1-6}$ alkoxycarbonyl group, an aryl group, —$OR^3$, and —$NR^{32}R^{33}$; wherein $R^{31}$, $R^{32}$, and $R^{33}$ are independently selected from a hydrogen atom, a $C_{1-8}$ alkyl group, an aryl $C_{1-6}$ alkyl group, an aryl group, a heteroaryl group, and —$COOR^{34}$; wherein $R^{34}$ represents a $C_{1-8}$ alkyl group, an aryl $C_{1-6}$ alkyl group, or an aryl group; or $R^{32}$ and $R^{33}$, together with a nitrogen atom to which they are bonded, may form a 4- to 7-membered hetero ring containing at least one nitrogen atom; and Group C consists of a $C_{1-6}$ alkoxycarbonyl group, a hydroxyl group, a $C_{1-8}$ alkyl group, an aryl $C_{1-6}$ alkoxy $C_{1-8}$ alkyl group, a hydroxy $C_{1-8}$ alkyl group, an aryloxy group, and a heteroaryloxy group.

A further aspect of the present invention provides the compound represented by the above formula (1), the prodrug thereof, or the pharmaceutically acceptable salt thereof, wherein $R^1$ and $R^2$, together with a nitrogen atom to which they are bonded, form a 4- to 10-membered hetero ring containing at least one nitrogen atom, wherein the hetero ring may have a substituent selected from Group C.

A further aspect of the present invention provides the compound represented by the above formula (1), the prodrug thereof, or the pharmaceutically acceptable salt thereof, wherein $Y^2$ or $Y^3$ represents a morpholinyl group, an azetidinyl group, a pyrrolidinyl group, or piperidinyl group, and the hetero ring group may be substituted with one or more substituents selected from a hydroxyl group and a hydroxy $C_{1-6}$ alkyl group.

A further aspect of the present invention provides the compound represented by the above formula (1), the prodrug thereof, or the pharmaceutically acceptable salt thereof, wherein $Y^2$ or $Y^3$ represents a morpholinyl group, an azetidinyl group, a pyrrolidinyl group, a 3-hydroxypyrrolidinyl group, a 2-hydroxymethylpyrrolidinyl group, a 3-hydroxymethylpyrrolidinyl group, a piperidinyl group, a 3-hydroxypiperidinyl group, a 4-hydroxypiperidinyl group, a 2-hydroxymethylpiperidinyl group, a 3-hydroxymethylpiperidinyl group, a 4-hydroxymethylpiperidinyl group, or a 4-hydroxy-4-hydroxymethylpiperidinyl group.

A further aspect of the present invention provides the compound represented by the above formula (1), the prodrug thereof, or the pharmaceutically acceptable salt thereof, wherein $R^1$ represents a hydrogen atom or a $C_{1-8}$ alkyl group (wherein the alkyl group may be substituted with one or more substituents selected from Group B); and $R^2$ represents a $C_{1-8}$ alkyl group that is substituted with one or more substituents selected from Group B, —$COOR^3$, or —$COCH_2NHCOOR^{21}$.

A further aspect of the present invention provides the compound represented by the above formula (1), the prodrug thereof, or the pharmaceutically acceptable salt thereof, wherein $R^1$ represents a hydrogen atom; and $R^2$ represents —$COOR^3$, —$COSR^5$, —$CONR^6R^7$, or —$COR^4$.

A further aspect of the present invention provides the compound represented by the above formula (1), the prodrug thereof, or the pharmaceutically acceptable salt thereof, wherein $R^2$ represents —$COOR^3$.

A further aspect of the present invention provides the compound represented by the above formula (1), the prodrug thereof, or the pharmaceutically acceptable salt thereof, wherein $R^3$ represents a $C_{1-8}$ alkyl group, a $C_{2-7}$ alkenyl group, or a $C_{2-7}$ alkynyl group (wherein the alkyl group, alkenyl group, and alkynyl group may be substituted with one or more substituents selected from a halogen atom, a hydroxyl group, or a $C_{1-6}$ alkoxy group (wherein the alkoxy group may be substituted with one or more substituents selected from a hydroxyl group, a $C_{1-6}$ alkoxy group, and a phenyl group)).

A further aspect of the present invention provides the compound represented by the above formula (1), the prodrug thereof, or the pharmaceutically acceptable salt thereof, wherein $R^3$ represents a $C_{1-8}$ alkyl group that is substituted with one or more hydroxyl groups, a $C_{2-7}$ alkenyl group that is substituted with one or more hydroxyl groups, or a $C_{2-7}$ alkynyl group that is substituted with one or more hydroxyl groups.

A further aspect of the present invention provides the compound represented by the above formula (1), the prodrug thereof, or the pharmaceutically acceptable salt thereof, wherein $R^3$ represents a $C_{1-6}$ alkyl group that is substituted with one or more hydroxyl groups.

A further aspect of the present invention provides the compound represented by the above formula (1), the prodrug thereof, or the pharmaceutically acceptable salt thereof, wherein $Y^2$ or $Y^3$ represents a bis(hydroxy $C_{1-6}$ alkyl)amino group, a methyl(hydroxy $C_{1-6}$ alkyl)amino group, a hydroxy $C_{1-6}$ alkylamino group, a methyl(morpholinyl $C_{1-6}$ alkyl) amino group, an amino $C_{1-6}$ alkylamino group, a $C_{1-6}$ alkoxycarbonylamino group, or a hydroxy $C_{1-6}$ alkoxycarbonylamino group.

A further aspect of the present invention provides the compound represented by the above formula (1), the prodrug thereof, or the pharmaceutically acceptable salt thereof, wherein $Y^2$ or $Y^3$ represents a bis(2-hydroxyethyl)amino group, a methyl(2-hydroxyethyl)amino group, a 2-hydroxyethylamino group, a methyl(2-morpholin-4-ylethyl)amino group, a methyl(2-aminoethyl)amino group, or a 2-hydroxyethyloxycarbonylamino group.

A further aspect of the present invention provides the compound represented by the above formula (1), the prodrug thereof, or the pharmaceutically acceptable salt thereof, wherein X represents a phenyl group or a heteroaryl group, and the phenyl group or heteroaryl group may be substituted with one or more substituents selected from Group A.

A further aspect of the present invention provides the compound represented by the above formula (1), the prodrug thereof, or the pharmaceutically acceptable salt thereof, wherein X represents a phenyl group, and the phenyl group may be substituted with one or more substituents selected from Group A.

A further aspect of the present invention provides the compound represented by the above formula (1), the prodrug thereof, or the pharmaceutically acceptable salt thereof, wherein X represents a phenyl group or a heteroaryl group, and the phenyl group or heteroaryl group may be substituted with one or more substituents selected from Group A; and Group A consists of a $C_{1-8}$ alkyl group that is substituted with one or more halogen atoms, an aryl group, a $C_{1-6}$ alkylthio group, a di($C_{1-6}$ alkyl)amino group, a 4- to 7-membered hetero ring group containing at least one nitrogen atom, a $C_{1-8}$ alkyl group, a $C_{2-7}$ alkenyl group, a $C_{2-7}$ alkynyl group, a $C_{1-6}$ alkoxy group (wherein the alkoxy group may be substituted with one or more halogen atoms), and a hydroxyl group.

A further aspect of the present invention provides the compound represented by the above formula (1), the prodrug thereof, or the pharmaceutically acceptable salt thereof, wherein X represents a phenyl group, and the phenyl group may be substituted with one or more substituents selected from an ethyl group, a trifluoromethyl group, a trifluoromethoxy group, a methylthio group, a methoxy group, a chloro group, a phenyl group, a dimethylamino group, a morpholinyl group, a piperidinyl group, and a pyrrolidinyl group.

A further aspect of the present invention provides the compound represented by the above formula (1), the prodrug thereof, or the pharmaceutically acceptable salt thereof, wherein X represents a phenyl group, which has, at least at the 2-position thereof, a $C_{1-8}$ alkyl group (wherein the alkyl group may be substituted with one or more halogen atoms), a $C_{1-6}$ alkylthio group, a di($C_{1-6}$ alkyl)amino group, a 4- to 7-membered hetero ring group containing at least one nitrogen atom, a $C_{1-6}$ alkoxy group (wherein the alkoxy group may be substituted with one or more halogen atoms), a phenyl group having an aryl group; or X represents a phenyl group, which has a hydroxy group at least at the 4-position thereof.

A further aspect of the present invention provides a compound represented by the following formula IV:

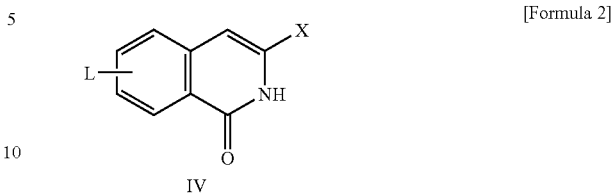

[Formula 2]

IV (wherein X represents a phenyl group or a heteroaryl group, and the phenyl group or heteroaryl group may be substituted with one or more substituents selected from Group A; and L represents a halogen atom that is bonded to the 6- or 7-position on an isoquinolone ring).

A further aspect of the present invention provides a method for producing the compound represented by the above formula (1), which comprises amination of the compound represented by formula VI.

A further aspect of the present invention provides a method for producing the compound represented by the above formula (1), which comprises allowing the compound represented by the formula VI to react with a suitable amine in the presence of a suitable solvent (for example, toluene, THF, 1,4-dioxane, xylene, dimethoxyethane, etc.), a suitable palladium catalyst (for example, $Pd(OAc)_2$, $Pd_2dba_3$, $PdCl_2[P(o\text{-}tol)_3]_2$, $Pd(O_2CCF_3)_2$, etc.), a ligand (for example, $P(o\text{-}tol)_3$, BINAP, DPPF, $P(t\text{-}Bu)_3$, 2-dicyclohexylphosphino-2'-(N,N-dimethylamino)biphenyl, 2-(di-t-butylphosphino)biphenyl, 2-(dicyclohexylphosphino)biphenyl, etc.), and a base (for example, t-BuONa, LiHMDS, $Cs_2CO_3$, $K_3PO_4$, etc.).

A further aspect of the present invention provides a pharmaceutical composition, which comprises, as an active ingredient, the compound represented by the above formula (1), the prodrug thereof, or the pharmaceutically acceptable salt thereof.

A further aspect of the present invention provides a therapeutic or preventive agent used for malignant tumor, which comprises, as an active ingredient, the compound represented by the above formula (1), the prodrug thereof, or the pharmaceutically acceptable salt thereof. Examples of malignant tumor herein include solid cancer.

Effects of the Invention

The present invention provides a 1-(2H)-isoquinolone derivative having excellent antitumor action. In addition, the present invention also provides a compound, which is useful as a therapeutic and preventive agent effective for proliferative diseases such as cancer, a production method thereof, an intermediate compound useful for such production, and a pharmaceutical composition comprising such a compound.

EMBODIMENT FOR CARRYING OUT THE INVENTION

In the present invention, the term "aryl group" is used to mean an aromatic hydrocarbon group containing 6 to 10 carbon atoms, which includes phenyl, 1-naphthyl, 2-naphthyl, and others.

In the present invention, the term "heteroaryl group" is used to mean a 5- to 10-membered aromatic hetero ring group containing a heteroatom selected from one or more oxygen atoms, nitrogen atoms, and sulfur atoms. Examples of such a heteroaryl group may include furyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridinyl, pyrimidinyl, pyrazinyl, pyridazinyl, indolyl, quinolinyl, and isoquinolyl.

In the present invention, the term "halogen atom" is used to mean a fluorine atom, a chlorine atom, a bromine atom, an iodine atom, or the like. A preferred example of such a halogen atom is a fluorine atom.

In the present invention, the term "$C_{1-8}$ alkyl group" is used to mean a linear or branched alkyl group containing 1 to 8 carbon atoms. Examples of such a $C_{1-8}$ alkyl group may include methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl. A preferred example of such a $C_{1-8}$ alkyl group is a linear or branched $C_{1-8}$ alkyl group, and a more preferred example is a linear or branched $C_{1-6}$ alkyl group.

In the present invention, the term "$C_{3-8}$ cycloalkyl group" is used to mean a cyclic or partially cyclic alkyl group containing 3 to 8 carbon atoms. Examples of such a $C_{3-8}$ cycloalkyl group may include cyclopropyl, cyclobutyl, cyclopentyl, cyclohexyl, cycloheptyl, cyclooctyl, methylcyclopropyl, cyclopropylmethyl, and cyclohexylmethyl.

In the present invention, the term "$C_{2-7}$ alkenyl group" is used to mean a linear or branched alkenyl group containing 2 to 7 carbon atoms. Examples of such a $C_{2-7}$ alkenyl group may include ethenyl(vinyl), 1-propenyl, 2-propenyl(allyl), propen-2-yl, and 3-butenyl(homoallyl).

In the present invention, the term "$C_{2-7}$ alkynyl group" is used to mean a linear or branched alkynyl group containing 2 to 7 carbon atoms. Examples of such a $C_{2-7}$ alkynyl group may include ethynyl, 1-propynyl, 2-propynyl, 1-butynyl, 2-butynyl, and 3-butynyl.

In the present invention, the term "$C_{1-6}$ alkoxy group" is used to mean an alkyloxy group having a linear or branched alkyl group containing 1 to 6 carbon atoms, and a cyclic or partially cyclic alkyl group containing 3 to 6 carbon atoms, as alkyl portions thereof. Examples of such a $C_{1-6}$ alkoxy group may include methoxy, ethoxy, n-propoxy, i-propoxy, n-butoxy, s-butoxy, i-butoxy, t-butoxy, n-pentyloxy, 3-methylbutoxy, 2-methylbutoxy, 1-methylbutoxy, 1-ethylpropoxy, n-hexyloxy, 4-methylpentyloxy, 3-methylpentyloxy, 2-methylpentyloxy, 1-methylpentyloxy, 3-ethylbutoxy, 2-ethylbutoxy, cyclopropoxy, cyclobutoxy, cyclopentyloxy, cyclohexyloxy, and cyclopropylmethoxy.

In the present invention, the term "aryloxy group" is used to mean an aryloxy group having, as an aryl portion thereof, an aromatic hydrocarbon group containing 6 to 10 carbon atoms, which has already been defined above. Examples of such an aryloxy group may include phenoxy, 1-naphthyloxy, and 2-naphthyloxy.

In the present invention, the term "heteroaryloxy group" is used to mean a heteroaryloxy group having, as a heteroaryl portion thereof, a 5- to 10-membered aromatic hetero ring group containing a heteroatom selected from one or more oxygen atoms, nitrogen atoms, and sulfur atoms, which has already been defined above. Examples of such a heteroaryloxy group may include furyloxy, thienyloxy, pyrrolyloxy, imidazolyloxy, pyrazolyloxy, oxazolyloxy, isoxazolyloxy, thiazolyloxy, isothiazolyloxy, oxadiazolyloxy, thiadiazolyloxy, triazolyloxy, tetrazolyloxy, pyridinyloxy, pyrimidinyloxy, pyrazinyloxy, pyridazinyloxy, indolyloxy, quinolinyloxy, and isoquinolinyloxy.

In the present invention, the term "$C_{1-6}$ haloalkyl group" is used to mean an alkyl group substituted with one or more halogen atoms, which has, as alkyl portions thereof, a linear or branched alkyl group containing 1 to 6 carbon atoms, and a cyclic or partially cyclic alkyl group containing 3 to 6 carbon atoms. Examples of such a $C_{1-6}$ haloalkyl group may include trifluoromethyl, trichloromethyl, chlorodifluoromethyl, 2,2,2-trifluoroethyl, perfluoroethyl, 2,2,2-trichloroethyl, bromomethyl, dibromomethyl, tribromomethyl, iodomethyl, difluoromethyl, and dichloromethyl.

In the present invention, the term "$C_{1-6}$ haloalkoxy group" is used to mean an alkoxy group substituted with one or more halogen atoms, which has, as alkyl portions thereof, a linear or branched alkyl group containing 1 to 6 carbon atoms, and a cyclic or partially cyclic alkyl group containing 3 to 6 carbon atoms. Examples of such a $C_{1-6}$ haloalkoxy group may include trifluoromethoxy, trichloromethoxy, chlorodifluoromethoxy, 2,2,2-trifluoroethoxy, perfluoroethoxy, 2,2,2-trichloroethoxy, bromomethoxy, dibromomethoxy, tribromomethoxy, iodomethoxy, difluoromethoxy, and dichloromethoxy.

In the present invention, the term "$C_{1-6}$ alkylamino group" is used to mean an alkylamino group having, as alkyl portions thereof, a linear or branched alkyl group containing 1 to 6 carbon atoms, and a cyclic or partially cyclic alkyl group containing 3 to 6 carbon atoms. Examples of such a $C_{1-6}$ alkylamino group may include methylamino, ethylamino, n-propylamino, i-propylamino, n-butylamino, s-butylamino, i-butylamino, t-butylamino, n-pentylamino, 3-methylbutylamino, 2-methylbutylamino, 1-methylbutylamino, 1-ethylpropylamino, n-hexylamino, 4-methylpentylamino, 3-methylpentylamino, 2-methylpentylamino, 1-methylpentylamino, 3-ethylbutylamino, and 2-ethylbutylamino.

In the present invention, the term "di($C_{1-6}$ alkyl)amino group" is used to mean a dialkylamino group having, as two alkyl portions, a linear or branched alkyl group containing 1 to 6 carbon atoms, and a cyclic or partially cyclic alkyl group containing 3 to 6 carbon atoms. The above two alkyl portions may be either identical to or different from each other. Examples of such a di($C_{1-6}$ alkyl)amino group may include dimethylamino, diethylamino, di-n-propylamino, di-i-propylamino, di-n-butylamino, methyl-n-butylamino, methyl-s-butylamino, methyl-i-butylamino, methyl-t-butylamino, ethyl-n-butylamino, ethyl-s-butylamino, ethyl-i-butylamino, and ethyl-t-butylamino.

In the present invention, the term "$C_{1-6}$ alkylcarbonyl group" is used to mean an alkylcarbonyl group having, as alkyl portions thereof, a linear or branched alkyl group containing 1 to 6 carbon atoms, and a cyclic or partially cyclic alkyl group containing 3 to 6 carbon atoms.

In the present invention, the term "$C_{1-6}$ alkylaminocarbonyl group" is used to mean an alkylaminocarbonyl group having, as alkyl portions thereof, a linear or branched alkyl group containing 1 to 6 carbon atoms, and a cyclic or partially cyclic alkyl group containing 3 to 6 carbon atoms.

In the present invention, the term "amino $C_{1-6}$ alkoxycarbonyl group" is used to mean an aminoalkoxycarbonyl group having, as alkoxy portions thereof, a linear or branched alkoxy group containing 1 to 6 carbon atoms, and a cyclic or partially cyclic alkoxy group containing 3 to 6 carbon atoms.

In the present invention, the term "hydroxy $C_{1-6}$ alkyl group" is used to mean a hydroxyalkyl group having, as alkyl portions thereof, a linear or branched alkyl group containing 1 to 6 carbon atoms, and a cyclic or partially cyclic alkyl group containing 3 to 6 carbon atoms.

In the present invention, the term "$C_{1-6}$ alkylthio group" is used to mean an alkylthio group having, as alkyl portions thereof, a linear or branched alkyl group containing 1 to 6 carbon atoms, and a cyclic or partially cyclic alkyl group containing 3 to 6 carbon atoms. Examples of such a $C_{1-6}$ alkylthio group may include methylthio, ethylthio, n-propylthio, i-propylthio, n-butylthio, s-butylthio, i-butylthio, t-butylthio, n-pentylthio, 3-methylbutylthio, 2-methylbutylthio, 1-methylbutylthio, 1-ethylpropylthio, n-hexylthio, 4-methylpentylthio, 3-methylpentylthio, 2-methylpentylthio, 1-methylpentylthio, 3-ethylbutylthio, and 2-ethylbutylthio.

In the present invention, the term "aryl $C_{1-6}$ alkyl group" is used to mean an aralkyl group, which has, as an aryl group thereof, the above defined aromatic hydrocarbon group containing 6 to 10 carbon atoms, and as alkyl portions thereof, a linear or branched alkyl group containing 1 to 6 carbon atoms, and a cyclic or partially cyclic alkyl group containing 3 to 6 carbon atoms. Examples of such an aryl $C_{1-6}$ alkyl group may include benzyl, 1-phenethyl, and 2-phenethyl.

In the present invention, the term "a 4- to 7-membered hetero ring containing at least one nitrogen atom" is used to mean a saturated or unsaturated hetero ring containing 4 to 7 atoms in the ring thereof, which contains one or more nitrogen atoms and may also contain one or more hetero atoms selected from oxygen atoms and sulfur atoms. Aromatic hetero ring is also included herein. Herein, sulfur atoms contained in the ring may be oxidized, so as to form $S(O)_n$ (wherein n=1 or 2). Specific examples may include azetidine, pyrrolidine, piperidine, piperazine, pyrrole, imidazole, imidazoline, pyrazole, pyrazoline, oxazoline, morpholine, thiomorpholine, oxothiomorpholine, dioxothiomorpholine, pyridine, pyrazine, pyrimidine, pyridazine, hexamethyleneimine, and octahydroisoquinoline.

In the present invention, the term "4- to 7-hetero ring group containing at least one nitrogen atom" is used to mean a saturated or unsaturated hetero ring group containing 3 to 7 atoms in the ring thereof, which contains one or more nitrogen atoms and may also contain one or more heteroatoms selected from oxygen atoms and sulfur atoms. Herein, sulfur atoms contained in the ring may be oxidized, so as to form $S(O)_n$ (wherein n=1 or 2). Such a hetero ring group may have a monocyclic ring, condensed ring, or spiro ring skeleton, or may also be an aromatic hetero ring group. Specific examples may include azetidinyl, pyrrolidinyl, piperidinyl, piperazinyl, pyrrolyl, imidazolyl, imidazolinyl, pyrazolyl, pyrazolinyl, oxazolinyl, morpholinyl, thiomorpholinyl, oxothiomorpholinyl, dioxothiomorpholinyl, pyridinyl, pyrazinyl, pyrimidinyl, pyridazinyl, hexamethyleneimino, and octahydroisoquinolyl. The position of the above hetero ring group to be substituted is not particularly limited, as long as it is a substitutable position on a carbon atom or nitrogen atom.

In the present invention, the term "4- to 7-membered hetero ring group" is used to mean a saturated or unsaturated hetero ring group containing 4 to 7 atoms in the ring thereof, which may contain one or more heteroatoms or heteromolecules selected from nitrogen atoms, oxygen atoms, and sulfur atoms. An aromatic hetero ring is also included therein. Herein, sulfur atoms contained in the ring may be oxidized, so as to form $S(O)_n$ (wherein n=1 or 2). Specific examples may include azetidinyl, pyrrolidinyl, piperidinyl, piperazinyl, pyrrolyl, imidazolyl, imidazolinyl, pyrazolyl, pyrazolinyl, oxazolinyl, morpholinyl, thiomorpholinyl, oxothiomorpholinyl, dioxothiomorpholinyl, pyridinyl, pyrazinyl, pyrimidinyl, pyridazinyl, hexamethyleneimino, furyl, tetrahydrofuryl, thienyl, tetrahydrothienyl, dioxolanyl, oxathiolanyl, and dioxanyl. The position of the above hetero ring group to be substituted is not particularly limited, as long as it is a substitutable position on a carbon atom or nitrogen atom.

In the present invention, the term "4- to 10-membered hetero ring group containing at least one nitrogen atom" is used to mean a saturated or unsaturated hetero ring containing 3 to 10 atoms in the ring thereof, which contains one or more nitrogen atoms and may also contain one or more heteroatoms selected from oxygen atoms and sulfur atoms. An aromatic hetero ring, or a bicyclo hetero ring containing a condensed ring skeleton and a spiro ring skeleton, is also included therein. Herein, sulfur atoms contained in the ring may be oxidized, so as to form $S(O)_n$ (wherein n=1 or 2). Specific examples may include azetidine, pyrrolidine, piperidine, piperazine, pyrrole, imidazole, triazole, tetrazole, imidazoline, pyrazole, pyrazoline, oxazoline, morpholine, thiomorpholine, oxothiomorpholine, dioxothiomorpholine, hexamethyleneimine, decahydroquinoline, decahydroisoquinoline, indole, and octahydroindole.

A hetero ring group containing a spiro ring skeleton includes hetero ring groups containing hetero rings represented by the following formulas:

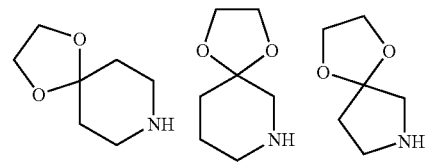

[Formula 3]

In the present invention, the term "$-S(O)_nR^{14}$" is used to mean $-SR^{14}$, $-SOR^{14}$, or $-SO_2R^{14}$. For example, such $-S(O)_nR^{14}$ includes $-S(O)_n$ ($C_{1-6}$ alkyl group), $-S(O)_n$ (aryl group), and $-S(O)_n$ (heteroaryl group). Specific examples of "$-S(O)_nR^{14}$" may include methylthio, ethylthio, n-propylthio, isopropylthio, trifluoromethylthio, benzylthio, 4-methylphenylthio, phenylthio, methylsulfinyl, ethylsulfinyl, n-propylsulfinyl, isopropylsulfinyl, trifluoromethylsulfinyl, benzylsulfinyl, 4-methylphenylsulfinyl, phenylsulfinyl, methylsulfonyl, ethylsulfonyl, n-propylsulfonyl, isopropylsulfonyl, trifluoromethylsulfonyl, benzylsulfonyl, 4-methylphenylsulfonyl, and phenylsulfonyl.

In the present invention, the term "$C_{1-6}$ alkylenedioxy group" is a divalent group "$-O-(C_{1-6}$ alkylene$)-O-$", which contains a linear or branched alkylene group containing 1 to 6 carbon atoms and is bonded to a carbon atom adjacent thereto. Examples of such a $C_{1-6}$ alkylenedioxy group may include methylenedioxy, ethylenedioxy, methylmethylenedioxy, and dimethylmethylenedioxy.

In the present specification, when any given group is substituted with one or more substituents, such substituents may be either identical to or different from one another. The number of such substituents ranges from 1 to the maximum number, which is substitutable on a chemical structure. The number of substituents is, for example, between 1 and 7, typically between 1 and 5, and particularly between 1 and 3.

The present invention includes a salt of the compound represented by the formula (1) and a pharmacologically acceptable salt of the prodrug of the above compound. These salts are produced by allowing the above compound or the prodrug thereof to come into contact with an acid or base, which can be used in production of a pharmaceutical. Examples of such a salt may include: hydrochloride, hydrobromide, hydroiodide, sulfate, sulfonate, phosphate, phosphonate, carboxylates such as acetate, citrate, malate, or salicylate, or alkali metal salts such as a sodium salt or a potassium salt; and alkali earth metal salts such as a magnesium salt or a calcium salt; and ammonium salts such as an ammonium salt, an alkylammonium salt, a dialkylammonium salt, a trialkylammonium salt, or a tetraalkylammonium salt.

The "prodrug" of the present invention means a derivative of the compound represented by the formula (1), which is enzymatically or nonenzymatically converted to the compound represented by the formula (1) or a pharmaceutically acceptable salt thereof under physiological conditions. When such a prodrug is administered to a patient, it may be inactive. However, such a prodrug is converted to the compound of the formula (1) and exists in the form of the compound of the formula (1) in vivo.

The compound represented by the formula (1) of the present invention may include compounds represented by the following formula, wherein X is a substitutable phenyl group:

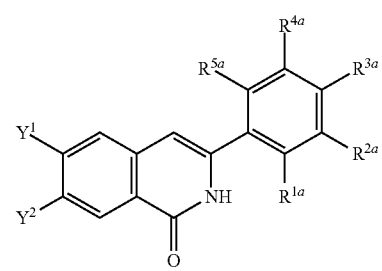

[Formula 4]

Specific examples of the present invention include the compound shown in the following Table 1, for example. However, such examples are not intended to limit the present invention. It is to be noted that compound names corresponding to the numbers shown in the table are also described.

In the following table, the symbol "Me" represents a methyl group, "Et" represents an ethyl group, "t-Bu" represents a t-butyl group, and "*" represents a binding portion.

TABLE 1

| Compound No. | $R^{1a}$ | $R^{2a}$ | $R^{3a}$ | $R^{4a}$ | $R^{5a}$ | $Y^1$ | $Y^2$ | Example |
|---|---|---|---|---|---|---|---|---|
| 1 | $CF_3$ | H | H | H | H | H | Cl | Example 1 Step B |
| 2 | H | H | H | H | H | H | Cl | Example 2 |
| 3 | $OCF_3$ | H | H | H | H | H | Cl | Example 3 |
| 4 | $CF_3$ | H | H | H | H | H | 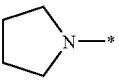 | Example 4 |
| 5 | H | H | H | H | H | H | 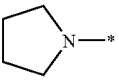 | Example 5 |
| 6 | $OCF_3$ | H | H | H | H | H | 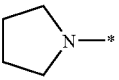 | Example 6 |
| 7 | $CF_3$ | H | H | H | H | H | 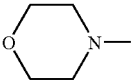 | Example 7 |
| 8 | H | H | H | H | H | H | 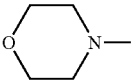 | Example 8 |
| 9 | $OCF_3$ | H | H | H | H | H | 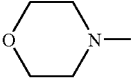 | Example 9 |
| 10 | $CF_3$ | H | H | H | H | H | 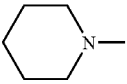 | Example 10 |
| 11 | H | H | H | H | H | H | 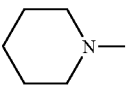 | Example 11 |
| 12 | $OCF_3$ | H | H | H | H | H | 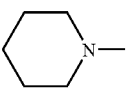 | Example 12 |
| 13 | H | H | H | H | H | H | 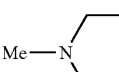 | Example 13 |
| 14 | H | H | H | H | H | H | 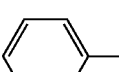 | Example 14 |
| 15 | H | H | H | H | H | H |  | Example 15 |

TABLE 1-continued

| Compound No. | $R^{1a}$ | $R^{2a}$ | $R^{3a}$ | $R^{4a}$ | $R^{5a}$ | $Y^1$ | $Y^2$ | Example |
|---|---|---|---|---|---|---|---|---|
| 16 | OCF₃ | H | H | H | H | H | morpholine-CH₂CH₂-NH-* | Example 16 |
| 17 | H | H | H | H | H | H | morpholine-CH₂CH₂-N(Me)-* | Example 17 |
| 18 | OCF₃ | H | H | H | H | H | morpholine-CH₂CH₂-N(Me)-* | Example 18 |
| 19 | CF₃ | H | H | H | H | H | morpholine-CH₂CH₂-N(Me)-* | Example 19 |
| 20 | CF₃ | H | H | H | H | H | 4-(hydroxymethyl)piperidin-1-yl-* | Example 20 |
| 21 | H | H | H | H | H | H | 4-(hydroxymethyl)piperidin-1-yl-* | Example 21 |
| 22 | OCF₃ | H | H | H | H | H | 4-(hydroxymethyl)piperidin-1-yl-* | Example 22 |
| 23 | CF₃ | H | H | H | H | H | 3-(hydroxymethyl)piperidin-1-yl-* | Example 23 |
| 24 | H | H | H | H | H | H | 3-(hydroxymethyl)piperidin-1-yl-* | Example 24 |
| 25 | OCF₃ | H | H | H | H | H | 3-(hydroxymethyl)piperidin-1-yl-* | Example 25 |
| 26 | CF₃ | H | H | H | H | H | 2-(hydroxymethyl)piperidin-1-yl-* | Example 26 |
| 27 | H | H | H | H | H | H | 2-(hydroxymethyl)piperidin-1-yl-* | Example 27 |

TABLE 1-continued

| Compound No. | $R^{1a}$ | $R^{2a}$ | $R^{3a}$ | $R^{4a}$ | $R^{5a}$ | $Y^1$ | $Y^2$ | Example |
|---|---|---|---|---|---|---|---|---|
| 28 | OCF$_3$ | H | H | H | H | H | 2-(hydroxymethyl)piperidin-1-yl | Example 28 |
| 29 | CF$_3$ | H | H | H | H | H | 4-hydroxypiperidin-1-yl | Example 29 |
| 30 | H | H | H | H | H | H | 4-hydroxypiperidin-1-yl | Example 30 |
| 31 | OCF$_3$ | H | H | H | H | H | 4-hydroxypiperidin-1-yl | Example 31 |
| 32 | CF$_3$ | H | H | H | H | H | 3-hydroxypiperidin-1-yl | Example 32 |
| 33 | H | H | H | H | H | H | 3-hydroxypiperidin-1-yl | Example 33 |
| 34 | OCF$_3$ | H | H | H | H | H | 3-hydroxypiperidin-1-yl | Example 34 |
| 35 | CF$_3$ | H | H | H | H | H | 3-hydroxypyrrolidin-1-yl | Example 35 |
| 36 | H | H | H | H | H | H | 3-hydroxypyrrolidin-1-yl | Example 36 |
| 37 | OCF$_3$ | H | H | H | H | H | 3-hydroxypyrrolidin-1-yl | Example 37 |
| 38 | CF$_3$ | H | H | H | H | H | NH$_2$ | Example 38 |
| 39 | H | H | H | H | H | H | NH$_2$ | Example 39 |
| 40 | OCF$_3$ | H | H | H | H | H | NH$_2$ | Example 40 |
| 41A | CF$_3$ | H | H | H | H | H | (2-hydroxyethyl)amino | Example 41 |
| 41B | CF$_3$ | H | H | H | H | H | bis(2-hydroxyethyl)amino | Example 41 |

TABLE 1-continued
| Compound No. | $R^{1a}$ | $R^{2a}$ | $R^{3a}$ | $R^{4a}$ | $R^{5a}$ | $Y^1$ | $Y^2$ | Example |
|---|---|---|---|---|---|---|---|---|
| 42A | H | H | H | H | H | H | <br>CF3COOH | Example 42 |
| 42B | H | H | H | H | H | H | 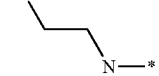 | Example 42 |
| 43A | OCF$_3$ | H | H | H | H | H |  | Example 43 |
| 43B | OCF$_3$ | H | H | H | H | H |  | Example 43 |
| 44A | H | H | H | H | H | H | 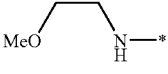 | Example 44 |
| 44B | H | H | H | H | H | H | 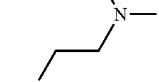 | Example 44 |
| 45 | H | H | H | H | H | H | 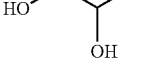 | Example 45 |
| 46 | H | H | H | H | H | H | 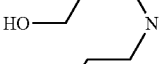 | Example 46 |
| 47 | CF$_3$ | H | H | H | H | H | 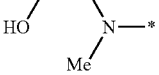 | Example 47 |
| 48 | H | H | H | H | H | H | 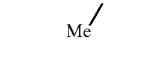 | Example 48 |
| 49 | OCF$_3$ | H | H | H | H | H | 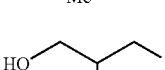 | Example 49 |
| 50 | H | H | H | H | H | H |  | Example 50 |

TABLE 1-continued

| Compound No. | $R^{1a}$ | $R^{2a}$ | $R^{3a}$ | $R^{4a}$ | $R^{5a}$ | $Y^1$ | $Y^2$ | Example |
|---|---|---|---|---|---|---|---|---|
| 51 | H | H | H | H | H | H | HO-CH(OH)-CH(OH)-CH2-N(Me)-* (with stereochemistry; 2,3,4-trihydroxybutyl; terminal N-Me) | Example 51 |
| 52 | OCF$_3$ | H | H | H | H | H | t-BuO-C(=O)-NH-CH2CH2-N(Me)-* | Example 52 |
| 53 | OCF$_3$ | H | H | H | H | H | H$_2$N-CH2CH2-N(Me)-*  2CF3COOH | Example 53 |
| 54 | H | H | H | H | H | H | H$_2$N-CH2CH2-N(H)-*  2CF3COOH | Example 54 |
| 55 | H | H | H | H | H | H | Me$_2$N-CH2CH2-N(Me)-* | Example 55 |
| 56 | H | H | H | H | H | H | H$_2$N-CH2CH2-N(Me)-*  CF3COOH | Example 56 |
| 57 | H | H | H | H | H | H | Cl-CH2-C(=O)-NH-* | Example 57 |
| 58 | H | H | H | H | H | H | MeO-CH2-C(=O)-NH-* | Example 58 |
| 59 | H | H | H | H | H | H | PhO-CH2-C(=O)-NH-* | Example 59 |
| 60 | H | H | H | H | H | H | BnO-CH2-C(=O)-NH-* | Example 60 |
| 61 | CF$_3$ | H | H | H | H | H | EtO-C(=O)-NH-* | Example 61 |
| 62 | H | H | H | H | H | H | EtO-C(=O)-NH-* | Example 62 |

TABLE 1-continued

| Compound No. | R¹ᵃ | R²ᵃ | R³ᵃ | R⁴ᵃ | R⁵ᵃ | Y¹ | Y² | Example |
|---|---|---|---|---|---|---|---|---|
| 63 | H | H | H | H | H | H | t-BuO-C(=O)-NH-CH₂-C(=O)-NH-* | Example 63 |
| 64 | H | H | H | H | H | H | H₂N-CH₂-C(=O)-NH-* · CF₃COOH | Example 64 |
| 65 | H | H | H | H | H | H | morpholin-4-yl-CH₂-C(=O)-NH-* | Example 65 |
| 66 | H | H | H | H | H | H | Me₂N-CH₂-C(=O)-NH-* | Example 66 |
| 67 | H | H | H | H | H | H | (4-methylpiperazin-1-yl)-CH₂-C(=O)-NH-* | Example 67 |
| 68 | H | H | H | H | H | morpholin-4-yl-* | H | Example 68 Step C |

Compound names corresponding to the aforementioned compound Nos. are described below.

(1): 7-chloro-3-(2-trifluoromethylphenyl)-2H-isoquinolin-1-one,
(2): 7-chloro-3-phenyl-2H-isoquinolin-1-one,
(3): 7-chloro-3-(2-trifluoromethoxyphenyl)-2H-isoquinolin-1-one,
(4): 7-pyrrolidin-1-yl-3-(2-trifluoromethylphenyl)-2H-isoquinolin-1-one,
(5): 3-phenyl-7-pyrrolidin-1-yl-2H-isoquinolin-1-one,
(6): 7-pyrrolidin-1-yl-3-(2-trifluoromethoxyphenyl)-2H-isoquinolin-1-one,
(7): 7-morpholin-4-yl-3-(2-trifluoromethylphenyl)-2H-isoquinolin-1-one,
(8): 7-morpholin-4-yl-3-phenyl-2H-isoquinolin-1-one,
(9): 7-morpholin-4-yl-3-(2-trifluoromethoxyphenyl)-2H-isoquinolin-1-one,
(10): 7-piperidin-1-yl-3-(2-trifluoromethylphenyl)-2H-isoquinolin-1-one,
(11): 3-phenyl-7-piperidin-1-yl-2H-isoquinolin-1-one,
(12): 7-piperidin-1-yl-3-(2-trifluoromethoxyphenyl)-2H-isoquinolin-1-one,
(13): 7-(4-methylpiperazin-1-yl)-3-phenyl-2H-isoquinolin-1-one,
(14): 7-(benzylmethylamino)-3-phenyl-2H-isoquinolin-1-one,
(15): 7-(2-morpholin-4-ylethylamino)-3-phenyl-2H-isoquinolin-1-one,
(16): 7-(2-morpholin-4-ylethylamino)-3-(2-trifluoromethoxyphenyl)-2H-isoquinolin-1-one,
(17): 7-[methyl(2-morpholin-4-ylethyl)amino]-3-phenyl-2H-isoquinolin-1-one,
(18): 7-[methyl(2-morpholin-4-ylethyl)amino]-3-(2-trifluoromethoxyphenyl)-2H-isoquinolin-1-one,
(19): 7-[methyl(2-morpholin-4-ylethyl)amino]-3-(2-trifluoromethylphenyl)-2H-isoquinolin-1-one,
(20): 7-(4-hydroxymethylpiperidin-1-yl)-3-(2-trifluoromethylphenyl)-2H-isoquinolin-1-one,
(21): 7-(4-hydroxymethylpiperidin-1-yl)-3-phenyl-2H-isoquinolin-1-one,
(22): 7-(4-hydroxymethylpiperidin-1-yl)-3-(2-trifluoromethoxyphenyl)-2H-isoquinolin-1-one,
(23): 7-(3-hydroxymethylpiperidin-1-yl)-3-(2-trifluoromethylphenyl)-2H-isoquinolin-1-one,
(24): 7-(3-hydroxymethylpiperidin-1-yl)-3-phenyl-2H-isoquinolin-1-one,
(25): 7-(3-hydroxymethylpiperidin-1-yl)-3-(2-trifluoromethoxyphenyl)-2H-isoquinolin-1-one,
(26): 7-(2-hydroxymethylpiperidin-1-yl)-3-(2-trifluoromethylphenyl)-2H-isoquinolin-1-one,
(27): 7-(2-hydroxymethylpiperidin-1-yl)-3-phenyl-2H-isoquinolin-1-one,
(28): 7-(2-hydroxymethylpiperidin-1-yl)-3-(2-trifluoromethoxyphenyl)-2H-isoquinolin-1-one,
(29): 7-(4-hydroxypiperidin-1-yl)-3-(2-trifluoromethylphenyl)-2H-isoquinolin-1-one,
(30): 7-(4-hydroxypiperidin-1-yl)-3-phenyl-2H-isoquinolin-1-one,
(31): 7-(4-hydroxypiperidin-1-yl)-3-(2-trifluoromethoxyphenyl)-2H-isoquinolin-1-one, (32): 7-(3-hydroxypiperidin-1-yl)-3-(2-trifluoromethylphenyl)-2H-isoquinolin-1-one,
(33): 7-(3-hydroxypiperidin-1-yl)-3-phenyl-2H-isoquinolin-1-one,
(34): 7-(3-hydroxypiperidin-1-yl)-3-(2-trifluoromethoxyphenyl)-2H-isoquinolin-1-one,
(35): 7-(3-hydroxypyrrolidin-1-yl)-3-(2-trifluoromethylphenyl)-2H-isoquinolin-1-one,
(36): 7-(3-hydroxypyrrolidin-1-yl)-3-phenyl-2H-isoquinolin-1-one,
(37): 7-(3-hydroxypyrrolidin-1-yl)-3-(2-trifluoromethoxyphenyl)-2H-isoquinolin-1-one,
(38): 7-amino-3-(2-trifluoromethylphenyl)-2H-isoquinolin-1-one,
(39): 7-amino-3-phenyl-2H-isoquinolin-1-one,
(40): 7-amino-3-(2-trifluoromethoxyphenyl)-2H-isoquinolin-1-one,
(41A): 7-(2-hydroxyethylamino)-3-(2-trifluoromethylphenyl)-2H-isoquinolin-1-one,
(41B): 7-[bis(2-hydroxyethyl)amino]-3-(2-trifluoromethylphenyl)-2H-isoquinolin-1-one,
(42A): 7-(2-hydroxyethyl)amino-3-phenyl-2H-isoquinolin-1-one monotrifluoroacetate,
(42B): 7-[bis(2-hydroxyethyl)amino]-3-phenyl-2H-isoquinolin-1-one,
(43A): 7-(2-hydroxyethylamino)-3-(2-trifluoromethoxyphenyl)-2H-isoquinolin-1-one,
(43B): 7-[bis(2-hydroxyethyl)amino]-3-(2-trifluoromethoxyphenyl)-2H-isoquinolin-1-one,
(44A): 7-(2-methoxyethylamino)-3-phenyl-2H-isoquinolin-1-one,
(44B): 7-[bis(2-methoxyethyl)amino]-3-phenyl-2H-isoquinolin-1-one,
(45): 7-(2,3-dihydroxypropylamino)-3-phenyl-2H-isoquinolin-1-one,
(46): 7-[(2,3-dihydroxypropyl)(2-hydroxyethyl)amino]-3-phenyl-2H-isoquinolin-1-one,
(47): 7-[(2-hydroxyethyl)methylamino]-3-(2-trifluoromethylphenyl)-2H-isoquinolin-1-one,
(48): 7-[(2-hydroxyethyl)methylamino]-3-phenyl-2H-isoquinolin-1-one,
(49): 7-[(2-hydroxyethyl)methylamino]-3-(2-trifluoromethoxyphenyl)-2H-isoquinolin-1-one,
(50): 7-[(2,3-dihydroxypropyl)methylamino]-3-phenyl-2H-isoquinolin-1-one,
(51): 7-[methyl((2S,3R)-2,3,4-trihydroxybutyl)amino]-3-phenyl-2H-isoquinolin-1-one,
(52): t-butyl(2-{methyl[1-oxo-3-(2-trifluoromethoxyphenyl)-1,2-dihydroisoquinolin-7-yl]amino}ethyl)carbamate,
(53): 7-[(2-aminoethyl)methylamino]-3-(2-trifluoromethoxyphenyl)-2H-isoquinolin-1-one ditrifluoroacetate,
(54): 7-(2-aminoethylamino)-3-phenyl-2H-isoquinolin-1-one ditrifluoroacetate,
(55): 7-[(2-dimethylaminoethyl)methylamino]-3-phenyl-2H-isoquinolin-1-one,
(56): 7-[(2-aminoethyl)methylamino]-3-phenyl-2H-isoquinolin-1-one monotrifluoroacetate,
(57): 2-chloro-N-(1-oxo-3-phenyl-1,2-dihydroisoquinolin-7-yl)acetamide,
(58): 2-methoxy-N-(1-oxo-3-phenyl-1,2-dihydroisoquinolin-7-yl)acetamide,
(59): N-(1-oxo-3-phenyl-1,2-dihydroisoquinolin-7-yl)-2-phenoxyacetamide,
(60): 2-benzyloxy-N-(1-oxo-3-phenyl-1,2-dihydroisoquinolin-7-yl)acetamide,
(61): ethyl[1-oxo-3-(2-trifluoromethylphenyl)-1,2-dihydroisoquinolin-7-yl]carbamate,
(62): ethyl(1-oxo-3-phenyl-1,2-dihydroisoquinolin-7-yl)carbamate,
(63): t-butyl[(1-oxo-3-phenyl-1,2-dihydroisoquinolin-7-ylcarbamoyl)methyl]carbamate,
(64): 2-amino-N-(1-oxo-3-phenyl-1,2-dihydroisoquinolin-7-yl)acetamide monotrifluoroacetate,
(65): 2-morpholin-4-yl-N-(1-oxo-3-phenyl-1,2-dihydroisoquinolin-7-yl)acetamide,
(66): 2-dimethylamino-N-(1-oxo-3-phenyl-1,2-dihydroisoquinolin-7-yl)acetamide,
(67): 2-(4-methylpiperazin-1-yl)-N-(1-oxo-3-phenyl-1,2-dihydroisoquinolin-7-yl)acetamide, and
(68): 6-morpholin-4-yl-3-phenyl-2H-isoquinolin-1-one.

Specific examples of the present invention further include the compound represented by the following formula and the compounds shown in Table 2:

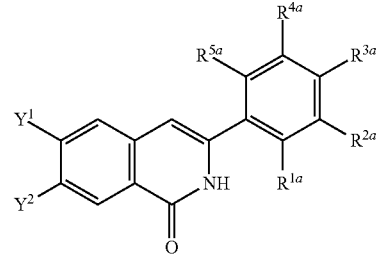

[Formula 5]

However, such examples are not intended to limit the present invention.

These compounds can be synthesized by reaction process 2. It is to be noted that compound names corresponding to the numbers shown in the table are also described. In addition, in the following table, the symbol "Me" represents a methyl group, and "*" represents a binding portion.

TABLE 2

| Compound No. | $R^{1a}$ | $R^{2a}$ | $R^{3a}$ | $R^{4a}$ | $R^{5a}$ | $Y^1$ | $Y^2$ | Example |
|---|---|---|---|---|---|---|---|---|
| 69 | $CF_3$ | H | H | H | H | 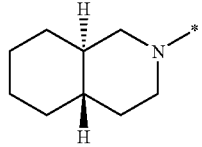 | | Example 69 |

TABLE 2-continued

| Compound No. | R^{1a} | R^{2a} | R^{3a} | R^{4a} | R^{5a} | Y^1 | Y^2 | Example |
|---|---|---|---|---|---|---|---|---|
| 70 | CF_3 | H | H | H | H | H | (2,6-dimethylmorpholin-4-yl, trans) | Example 70 |
| 71 | CF_3 | H | H | H | H | H | (S)-2-(hydroxymethyl)pyrrolidin-1-yl | Example 71 |
| 72 | CF_3 | H | H | H | H | H | (R)-2-(hydroxymethyl)pyrrolidin-1-yl | Example 72 |
| 73 | CF_3 | H | H | H | H | H | azetidin-1-yl | Example 73 |
| 74 | CF_3 | H | H | H | H | H | 4a-hydroxyoctahydroisoquinolin-2(1H)-yl | Example 74 |
| 75 | CF_3 | H | H | H | H | H | 4-(methoxycarbonyl)piperidin-1-yl | Example 75 |
| 76 | * (fused benzo) | * | H | H | H | | 4-hydroxypiperidin-1-yl | Example 76 |
| 77 | CF_3 | H | H | H | H | H | 1,4-dioxa-8-azaspiro[4.5]decan-8-yl | Example 77 |
| 78 | CF_3 | H | H | H | H | H | 2-(hydroxymethyl)morpholin-4-yl | Example 78 |
| 79 | CF_3 | H | H | H | H | H | 4-hydroxy-4-(hydroxymethyl)piperidin-1-yl | Example 79 |

Compound names corresponding to the aforementioned compound Nos. are described below.

(69): (4aS,8aR)-3'-(2-trifluoromethylphenyl)-3,4,4a,5,6,7,8,8a-octahydro-1H, 2'H-[2,7']biisoquinolinyl-1'-one,
(70): 7-((2S,6R)-2,6-dimethylmorpholin-4-yl)-3-(2-trifluoromethylphenyl)-2H-isoquinolin-1-one,
(71): 7-((S)-2-hydroxymethylpyrrolidin-1-yl)-3-(2-trifluoromethylphenyl)-2H-isoquinolin-1-one,
(72): 7-((R)-2-hydroxymethylpyrrolidin-1-yl)-3-(2-trifluoromethylphenyl)-2H-isoquinolin-1-one,
(73): 7-azetidin-1-yl-3-(2-trifluoromethylphenyl)-2H-isoquinolin-1-one,
(74): 4a-hydroxy-3'-(2-trifluoromethylphenyl)-3,4,4a,5,6,7,8,8a-octahydro-1H, 2'H-[2,7']biisoquinolinyl-1'-one,
(75): methyl 1-[1-oxo-3-(2-trifluoromethylphenyl)-1,2-dihydroisoquinolin-7-yl]piperidine-4-carboxylate,
(76): 7-(4-hydroxypiperidin-1-yl)-3-naphthalen-1-yl-2H-isoquinolin-1-one,
(77): 7-(1,4-dioxa-8-azaspiro[4.5]deca-8-yl)-3-(2-trifluoromethylphenyl)-2H-isoquinolin-1-one,
(78): 7-(2-hydroxymethylmorpholin-4-yl)-3-(2-trifluoromethylphenyl)-2H-isoquinolin-1-one, and
(79): 7-(4-hydroxy-4-hydroxymethylpiperidin-1-yl)-3-(2-trifluoromethylphenyl)-2H-isoquinolin-1-one.

Moreover, specific examples of the present invention further include the compound represented by the following formula and the compounds shown in Table 3:

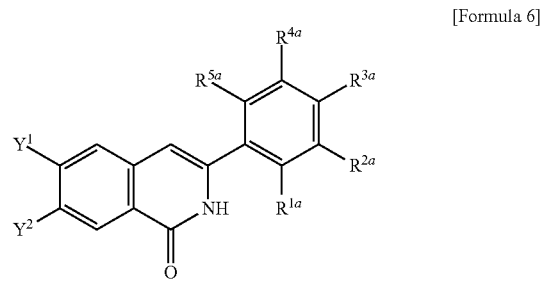

[Formula 6]

However, such examples are not intended to limit the present invention.

These compounds can be synthesized by reaction process 1. It is to be noted that compound names corresponding to the numbers shown in the table are also described. In addition, in the following table, the symbol "Me" represents a methyl group, "Et" represents an ethyl group, and "*" represents a binding portion.

TABLE 3

| Compound No. | $R^{1a}$ | $R^{2a}$ | $R^{3a}$ | $R^{4a}$ | $R^{5a}$ | $Y^1$ | $Y^2$ | Example |
|---|---|---|---|---|---|---|---|---|
| 80 | H | H | OMe | H | H | H | morpholin-N—* | Example 80 |
| 81 | OMe | H | H | H | H | H | morpholin-N—* | Example 81 |
| 82 | Et | H | H | H | H | H | morpholin-N—* | Example 82 |
| 83 | SMe | H | H | H | H | H | morpholin-N—* | Example 83 |
| 84 | Br | H | H | H | H | H | morpholin-N—* | Example 84 |
| 85 | piperidin-N—* | H | H | H | H | H | morpholin-N—* | Example 85 |
| 86 | morpholin-N—* | H | H | H | H | H | morpholin-N—* | Example 86 |
| 87 | Cl | H | H | H | Me | H | morpholin-N—* | Example 87 |
| 88 | H | OMe | H | OMe | H | H | morpholin-N—* | Example 88 |

TABLE 3-continued

| Compound No. | $R^{1a}$ | $R^{2a}$ | $R^{3a}$ | $R^{4a}$ | $R^{5a}$ | $Y^1$ | $Y^2$ | Example |
|---|---|---|---|---|---|---|---|---|
| 89 | H | OMe | OMe | OMe | H | H | (morpholin-4-yl, O∿N—*) | Example 89 |

Compound names corresponding to the aforementioned compound Nos. are described below.

(80): 3-(4-methoxyphenyl)-7-morpholin-4-yl-2H-isoquinolin-1-one,
(81): 3-(2-methoxyphenyl)-7-morpholin-4-yl-2H-isoquinolin-1-one,
(82): 3-(2-ethylphenyl)-7-morpholin-4-yl-2H-isoquinolin-1-one,
(83): 3-(2-methylsulfanylphenyl)-7-morpholin-4-yl-2H-isoquinolin-1-one,
(84): 3-(2-bromophenyl)-7-morpholin-4-yl-2H-isoquinolin-1-one,
(85): 7-morpholin-4-yl-3-(2-piperidin-1-ylphenyl)-2H-isoquinolin-1-one,
(86): 7-morpholin-4-yl-3-(2-morpholin-4-ylphenyl)-2H-isoquinolin-1-one,
(87): 3-(2-chloro-6-methylphenyl)-7-morpholin-4-yl-2H-isoquinolin-1-one,
(88): 3-(3,5-dimethoxyphenyl)-7-morpholin-4-yl-2H-isoquinolin-1-one, and
(89): 7-morpholin-4-yl-3-(3,4,5-trimethoxyphenyl)-2H-isoquinolin-1-one.

Furthermore, specific examples of the present invention further include the compounds represented by the following formulas and the compounds shown in Table 4:

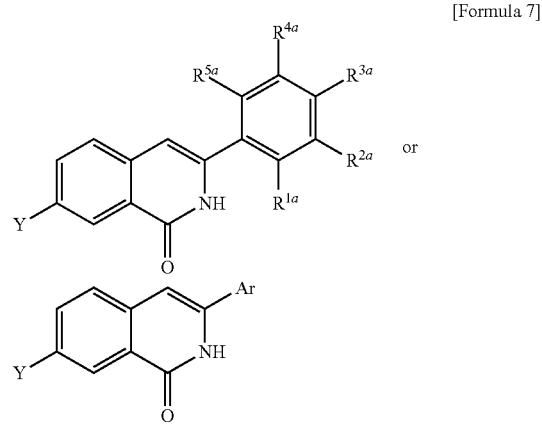

[Formula 7]

However, such examples are not intended to limit the present invention.

These compounds can be synthesized by reaction processes 1-7. It is to be noted that compound names corresponding to the numbers shown in the table are also described. In addition, in the following table, the symbol "Me" represents a methyl group, and "*" represents a binding portion.

TABLE 4

| Compound No. | $R^{1a}$ | $R^{2a}$ | $R^{3a}$ | $R^{4a}$ | $R^{5a}$ | Y | Ar | Example |
|---|---|---|---|---|---|---|---|---|
| 90 | Me | H | Ome | H | H | (3-hydroxypiperidin-1-yl) | — | Example 90 |
| 91 | (morpholin-4-yl) | H | H | H | H | (3-hydroxypiperidin-1-yl) | — | Example 91 |
| 92 | Me | H | H | H | H | (3-hydroxypiperidin-1-yl) | — | Example 92 |

TABLE 4-continued
| Compound No. | R$^{1a}$ | R$^{2a}$ | R$^{3a}$ | R$^{4a}$ | R$^{5a}$ | Y | Ar | Example |
|---|---|---|---|---|---|---|---|---|
| 93 | — | — | — | — | — | 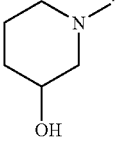 | 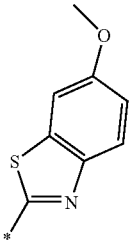 | Example 93 |
| 94 | 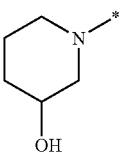 | H | H | H | H | 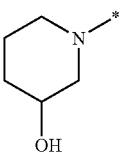 | — | Example 94 |
| 95 | 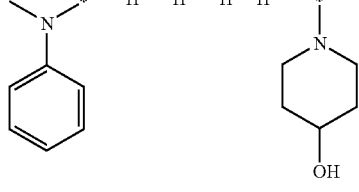 | H | H | H | H | 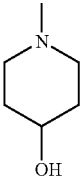 | — | Example 95 |
| 96 | CF$_3$ | H | F | H | H | 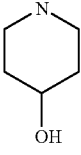 | — | Example 96 |
| 97 | 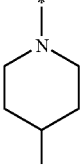 | H | H | H | H | 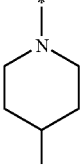 | — | Example 97 |
| 98 |  | H | H | H | H | 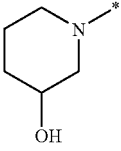 | — | Example 98 |
| 99 | Et | H | H | H | H | 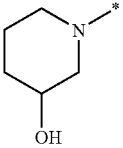 | — | Example 99 |
| 100 | 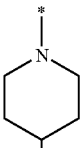 | H | H | H | H | 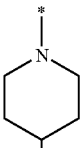 | — | Example 100 |

TABLE 4-continued

| Compound No. | R^{1a} | R^{2a} | R^{3a} | R^{4a} | R^{5a} | Y | Ar | Example |
|---|---|---|---|---|---|---|---|---|
| 101 | piperazine-N-Boc | H | H | H | H | 3-hydroxypiperidin-1-yl | — | Example 101 |
| 102 | piperazin-1-yl | H | H | H | H | 3-hydroxypiperidin-1-yl | — | Example 102 |
| 103 | 4-methylpiperazin-1-yl | H | H | H | H | 3-hydroxypiperidin-1-yl | — | Example 103 |
| 104 | CF$_3$ | H | H | H | H | thiomorpholin-4-yl | — | Example 104 |
| 105 | CF$_3$ | H | H | H | H | thiomorpholin-4-yl 1-oxide | — | Example 105 |
| 106 | CF$_3$ | H | H | H | H | (3R)-3-hydroxypiperidin-1-yl | — | Example 106 |
| 107 | CF$_3$ | H | H | H | H | (3S)-3-hydroxypiperidin-1-yl | — | Example 107 |
| 108 | Me | H | H | H | H | morpholin-4-yl | — | Example 108 |

TABLE 4-continued
| Compound No. | $R^{1a}$ | $R^{2a}$ | $R^{3a}$ | $R^{4a}$ | $R^{5a}$ | Y | Ar | Example |
|---|---|---|---|---|---|---|---|---|
| 109 | — | — | — | — | — | 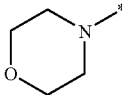 | 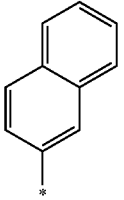 | Example 109 |
| 110 |  | H | H | H | H | 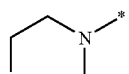 | — | Example 110 |
| 111 |  | H | H | H | H | 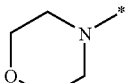 | — | Example 111 |
| 112 | $CF_3$ | H | H | H | H | 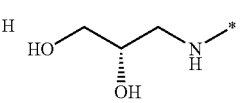 | — | Example 112 |
| 113 | $CF_3$ | H | H | H | H | 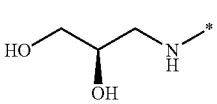 | — | Example 113 |
| 114 | $CF_3$ | H | H | H | H | 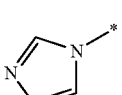 | — | Example 114 |
| 115 | $CF_3$ | H | H | H | H | 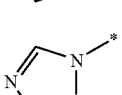 | — | Example 115 |
| 116 | $CF_3$ | H | H | H | H | 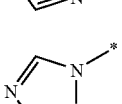 | — | Example 116 |
| 117 | $CF_3$ | H | H | H | H | 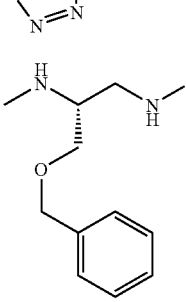 | — | Example 117 |
| 118 | $CF_3$ | H | H | H | H | 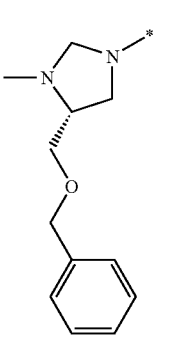 | — | Example 118 |

TABLE 4-continued
| Compound No. | $R^{1a}$ | $R^{2a}$ | $R^{3a}$ | $R^{4a}$ | $R^{5a}$ | Y | Ar | Example |
|---|---|---|---|---|---|---|---|---|
| 119 | $CF_3$ | H | H | H | H |  | — | Example 119 |
| 120 | $CF_3$ | H | H | H | H | 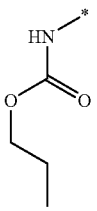 | — | Example 120 |
| 121 | $CF_3$ | H | H | H | H | 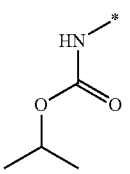 | — | Example 121 |
| 122 | $CF_3$ | H | H | H | H | 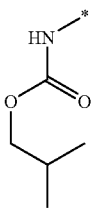 | — | Example 122 |
| 123 | $CF_3$ | H | H | H | H | 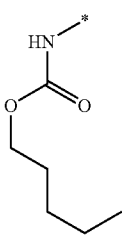 | — | Example 123 |
| 124 | $CF_3$ | H | H | H | H | 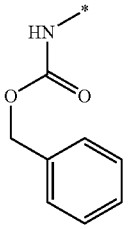 | — | Example 124 |
| 125 | $CF_3$ | H | H | H | H | 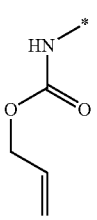 | — | Example 125 |

TABLE 4-continued

| Compound No. | $R^{1a}$ | $R^{2a}$ | $R^{3a}$ | $R^{4a}$ | $R^{5a}$ | Y | Ar | Example |
|---|---|---|---|---|---|---|---|---|
| 126 | CF$_3$ | H | H | H | H | carbamate with but-2-yn-1-yl group | — | Example 126 |
| 127 | CF$_3$ | H | H | H | H | carbamate with 2-(2-methoxyethoxy)ethyl group | — | Example 127 |
| 128 | CF$_3$ | H | H | H | H | carbamate with 3-methoxy-2,2-dimethylpropyl group | — | Example 128 |
| 129 | CF$_3$ | H | H | H | H | carbamate with 2-methoxyethyl group | — | Example 129 |
| 130 | CF$_3$ | H | H | H | H | carbamate with 2-(benzyloxy)ethyl group | — | Example 130 |
| 131 | CF$_3$ | H | H | H | H | carbamate with 2-hydroxyethyl group | — | Example 131 |

TABLE 4-continued

| Compound No. | R$^{1a}$ | R$^{2a}$ | R$^{3a}$ | R$^{4a}$ | R$^{5a}$ | Y | Ar | Example |
|---|---|---|---|---|---|---|---|---|
| 132 | CF$_3$ | H | H | H | H | (dibenzyloxy glycerol carbamate structure) | — | Example 132 |
| 133 | CF$_3$ | H | H | H | H | (dibenzyloxy glycerol carbamate structure, isomer) | — | Example 133 |
| 134 | CF$_3$ | H | H | H | H | (cyclohexylmethyl carbamate structure) | — | Example 134 |
| 135 | CF$_3$ | H | H | H | H | (cyclohexyl carbamate structure) | — | Example 135 |
| 136 | CF$_3$ | H | H | H | H | (furan-3-ylmethyl carbamate structure) | — | Example 136 |

TABLE 4-continued

| Compound No. | R$^{1a}$ | R$^{2a}$ | R$^{3a}$ | R$^{4a}$ | R$^{5a}$ | Y | Ar | Example |
|---|---|---|---|---|---|---|---|---|
| 137 | CF$_3$ | H | H | H | H | (ethyl thiocarbamate group) | — | Example 137 |
| 138 | CF$_3$ | H | H | H | H | (2,3-dihydroxypropyl carbamate group) | — | Example 138 |
| 139 | CF$_3$ | H | H | H | H | (1,3-dihydroxyprop-2-yl carbamate group) | — | Example 139 |
| 140 | morpholin-4-yl | H | H | H | H | (ethyl carbamate group) | — | Example 140 |
| 141 | CF$_3$ | H | F | H | H | (ethyl carbamate group) | — | Example 141 |
| 142 | OCF$_3$ | H | H | H | H | (ethyl carbamate group) | — | Example 142 |
| 143 | CF$_3$ | H | H | H | H | (N-methyl ethyl carbamate group) | — | Example 143 |
| 144 | CF$_3$ | H | H | H | H | (N-methyl 2-hydroxyethyl carbamate group) | — | Example 144 |
| 145 | Me | H | OH | H | H | (3-hydroxypiperidin-1-yl) | — | Example 145 |

TABLE 4-continued

| Compound No. | $R^{1a}$ | $R^{2a}$ | $R^{3a}$ | $R^{4a}$ | $R^{5a}$ | Y | Ar | Example |
|---|---|---|---|---|---|---|---|---|
| 146 | Cl | H | H | H | H | morpholin-4-yl | — | Example 146 |
| 147 | H | H | H | H | H | HN(*)-C(=O)-CH2-OH | — | Example 147 |
| 148 | H | H | H | H | H | *-NH-CH2-CH(OH)-CH(OH)-CH2-OH | — | Example 148 |
| 149 | CF3 | H | H | H | H | (CH3)2N-NH-* | — | Example 149 |
| 150 | CF3 | H | H | H | H | (CH3)2N-N(CH3)-* | — | Example 150 |
| 151 | CF3 | H | H | H | H | Ph2C=N-NH-* | — | Example 151 |
| 152 | CF3 | H | H | H | H | CH3NH-C(=O)-NH-* | — | Example 152 |
| 153 | CF3 | H | H | H | H | HC(=O)-N(CH3)-* | — | Example 153 |
| 154 | CF3 | H | H | H | H | Ph-C(=O)-NH-* | — | Example 154 |
| 155 | CF3 | H | H | H | H | (thiophen-2-yl)-CH2-C(=O)-NH-* | — | Example 155 |
| 156 | H | H | H | H | H | CH3-C(=O)-NH-* | — | Example 156 |

TABLE 4-continued

| Compound No. | R$^{1a}$ | R$^{2a}$ | R$^{3a}$ | R$^{4a}$ | R$^{5a}$ | Y | Ar | Example |
|---|---|---|---|---|---|---|---|---|
| 162 | — | — | — | — | — | 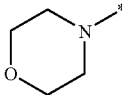 | 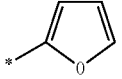 | Example 162 |
| 163 | — | — | — | — | — | 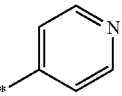 | 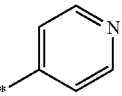 | Example 163 |
| 164 | CF3 | H | H | H | H | 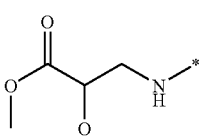 | — | Example 87 |

Compound names corresponding to the aforementioned compound Nos. are described below.

(90): 7-(3-hydroxypiperidin-1-yl)-3-(4-methoxy-2-methylphenyl)-2H-isoquinolin-1-one,
(91): 7-(3-hydroxypiperidin-1-yl)-3-(2-morpholin-4-ylphenyl)-2H-isoquinolin-1-one,
(92): 7-(3-hydroxypiperidin-1-yl)-3-o-tolyl-2H-isoquinolin-1-one,
(93): 7-(3-hydroxypiperidin-1-yl)-3-(6-methoxybenzothiazol-2-yl)-2H-isoquinolin-1-one,
(94): 7-(3-hydroxypiperidin-1-yl)-3-(2-morpholin-4-ylmethylphenyl)-2H-isoquinolin-1-one,
(95): 7-(4-hydroxypiperidin-1-yl)-3-[2-(methylphenylamino)phenyl]-2H-isoquinolin-1-one,
(96): 3-(4-fluoro-2-trifluoromethylphenyl)-7-(4-hydroxypiperidin-1-yl)-2H-isoquinolin-1-one,
(97): 7-(4-hydroxypiperidin-1-yl)-3-(2-morpholin-4-ylphenyl)-2H-isoquinolin-1-one,
(98): 3-biphenyl-2-yl-7-(3-hydroxypiperidin-1-yl)-2H-isoquinolin-1-one,
(99): 3-(2-ethylphenyl)-7-(3-hydroxypiperidin-1-yl)-2H-isoquinolin-1-one,
(100): 7-(4-hydroxypiperidin-1-yl)-3-[2-(2-methoxyethoxy)phenyl]-2H-isoquinolin-1-one,
(101): t-butyl 4-{2-[7-(3-hydroxypiperidin-1-yl)-1-oxo-1,2-dihydroisoquinolin-3-yl]phenyl}piperazine-1-carboxylate,
(102): 7-(3-hydroxypiperidin-1-yl)-3-(2-piperazin-1-ylphenyl)-2H-isoquinolin-1-one,
(103): 7-(3-hydroxypiperidin-1-yl)-3-[2-(4-methylpiperazin-1-yl)phenyl]-2H-isoquinolin-1-one,
(104): 7-thiomorpholin-4-yl-3-(2-trifluoromethylphenyl)-2H-isoquinolin-1-one,
(105): 7-(1-oxothiomorpholin-4-yl)-3-(2-trifluoromethylphenyl)-2H-isoquinolin-1-one,
(106): 7-((R)-3-hydroxypiperidin-1-yl)-3-(2-trifluoromethylphenyl)-2H-isoquinolin-1-one,
(107): 7-((S)-3-hydroxypiperidin-1-yl)-3-(2-trifluoromethylphenyl)-2H-isoquinolin-1-one,
(108): 7-morpholin-4-yl-3-o-tolyl-2H-isoquinolin-1-one,
(109): 7-morpholin-4-yl-3-naphthalen-2-yl-2H-isoquinolin-1-one,
(110): 3-(2-dimethylaminophenyl)-7-morpholin-4-yl-2H-isoquinolin-1-one,
(111): 7-morpholin-4-yl-3-(2-pyrrolidin-1-ylphenyl)-2H-isoquinolin-1-one,
(112): 7-((S)-2,3-dihydroxypropylamino)-3-(2-trifluoromethylphenyl)-2H-isoquinolin-1-one,
(113): 7-((R)-2,3-dihydroxypropylamino)-3-(2-trifluoromethylphenyl)-2H-isoquinolin-1-one,
(114): 7-imidazol-1-yl-3-(2-trifluoromethylphenyl)-2H-isoquinolin-1-one,
(115): 7-[1,2,4]triazol-1-yl-3-(2-trifluoromethylphenyl)-2H-isoquinolin-1-one,
(116): 7-tetrazol-1-yl-3-(2-trifluoromethylphenyl)-2H-isoquinolin-1-one,
(117): 7-((R)-3-benzyloxy-2-methylaminopropylamino)-3-(2-trifluoromethylphenyl)-2H-isoquinolin-1-one,
(118): 7-((R)-4-benzyloxymethyl-3-methylimidazolidin-1-yl)-3-(2-trifluoromethylphenyl)-2H-isoquinolin-1-one,
(119): 7-methylamino-3-(2-trifluoromethylphenyl)-2H-isoquinolin-1-one,
(120): propyl[1-oxo-3-(2-trifluoromethylphenyl)-1,2-dihydroisoquinolin-7-yl]carbamate,
(121): isopropyl[1-oxo-3-(2-trifluoromethylphenyl)-1,2-dihydroisoquinolin-7-yl]carbamate,
(122): isobutyl[1-oxo-3-(2-trifluoromethylphenyl)-1,2-dihydroisoquinolin-7-yl]carbamate,
(123): pentyl[1-oxo-3-(2-trifluoromethylphenyl)-1,2-dihydroisoquinolin-7-yl]carbamate,
(124): benzyl[1-oxo-3-(2-trifluoromethylphenyl)-1,2-dihydroisoquinolin-7-yl]carbamate,
(125): allyl[1-oxo-3-(2-trifluoromethylphenyl)-1,2-dihydroisoquinolin-7-yl]carbamate,
(126): but-2-ynyl[1-oxo-3-(2-trifluoromethylphenyl)-1,2-dihydroisoquinolin-7-yl]carbamate,
(127): 2-(2-methoxyethoxy)ethyl[1-oxo-3-(2-trifluoromethylphenyl)-1,2-dihydroisoquinolin-7-yl]carbamate,
(128): 3-methoxy-2,2-dimethylpropyl[1-oxo-3-(2-trifluoromethylphenyl)-1,2-dihydroisoquinolin-7-yl]carbamate,
(129): 2-methoxyethyl[1-oxo-3-(2-trifluoromethylphenyl)-1,2-dihydroisoquinolin-7-yl]carbamate,
(130): 2-benzyloxyethyl[1-oxo-3-(2-trifluoromethylphenyl)-1,2-dihydroisoquinolin-7-yl]carbamate,
(131): 2-hydroxyethyl[1-oxo-3-(2-trifluoromethylphenyl)-1,2-dihydroisoquinolin-7-yl]carbamate,
(132): (R)-2,3-bisbenzyloxypropyl[1-oxo-3-(2-trifluoromethylphenyl)-1,2-dihydroisoquinolin-7-yl]carbamate, (133): 2-benzyloxy-1-benzyloxymethylethyl[1-oxo-3-(2-tri-fluoromethylphenyl)-1,2-dihydroisoquinolin-7-yl]carbamate, (134): cyclohexylmethyl[1-oxo-3-(2-trifluoromethylphenyl)-1,2-dihydroisoquinolin-7-yl]carbamate, (135): cyclohexyl[1-oxo-3-(2-trifluoromethylphenyl)-1,2-dihydroisoquinolin-7-yl]carbamate, (136): furan-3-ylmethyl[1-oxo-3-(2-trifluoromethylphenyl)-1,2-dihydroisoquinolin-7-yl]carbamate, (137): S-ethyl[1-oxo-3-(2-trifluoromethylphenyl)-1,2-dihydroisoquinolin-7-yl]thiocarbamate, (138): (R)-2,3-dihydroxypropyl[1-oxo-3-(2-trifluoromethylphenyl)-1,2-dihydroisoquinolin-7-yl]carbamate, (139): 2-hydroxy-1-hydroxymethylethyl[1-oxo-3-(2-trifluoromethylphenyl)-1,2-dihydroisoquinolin-7-yl]carbamate, (140): ethyl[3-(2-morpholin-4-ylphenyl)-1-oxo-1,2-dihydroisoquinolin-7-yl]carbamate, (141): ethyl[3-(4-fluoro-2-trifluoromethylphenyl)-1-oxo-1,2-dihydroisoquinolin-7-yl]carbamate, (142): ethyl[1-oxo-3-(2-trifluoromethoxyphenyl)-1,2-dihydroisoquinolin-7-yl]carbamate, (143): ethyl methyl[1-oxo-3-(2-trifluoromethylphenyl)-1,2-dihydroisoquinolin-7-yl]carbamate, (144): 2-hydroxyethyl methyl[1-oxo-3-(2-trifluoromethylphenyl)-1,2-dihydroisoquinolin-7-yl]carbamate, (145): 3-(4-hydroxy-2-methylphenyl)-7-(3-hydroxypiperidin-1-yl)-2H-isoquinolin-1-one, (146): 3-(2-chlorophenyl)-7-morpholin-4-yl-2H-isoquinolin-1-one, (147): 2-hydroxy-N-(1-oxo-3-phenyl-1,2-dihydroisoquinolin-7-yl)acetamide, (148): 3-phenyl-7-((2S,3R)-2,3,4-trihydroxybutylamino)-2H-isoquinolin-1-one, (149): 7-(2,2-dimethylhydrazino)-3-(2-trifluoromethylphenyl)-2H-isoquinolin-1-one, (150): 3-(2-trifluoromethylphenyl)-7-(1,2,2-trimethylhydrazino)-2H-isoquinolin-1-one, (151): 7-(N-benzhydrylidenehydrazino)-3-(2-trifluoromethylphenyl)-2H-isoquinolin-1-one, (152): 1-methyl-3-[1-oxo-3-(2-trifluoromethylphenyl)-1,2-dihydroisoquinolin-7-yl]urea, (153): N-methyl-N-[1-oxo-3-(2-trifluoromethylphenyl)-1,2-dihydroisoquinolin-7-yl]formamide, (154): N-[1-oxo-3-(2-trifluoromethylphenyl)-1,2-dihydroisoquinolin-7-yl]benzamide, (155): N-[1-oxo-3-(2-trifluoromethylphenyl)-1,2-dihydroisoquinolin-7-yl]-2-thiophen-2-ylacetamide, (156): N-(1-oxo-3-phenyl-1,2-dihydroisoquinolin-7-yl)acetamide, (162): 3-furan-2-yl-7-morpholin-4-yl-2H-isoquinoline-1-one, (163): 7-morpholin-4-yl-3-pyridin-4-ylisoquinolin-1-one ditrifluoroacetate, and (164): methyl 2-hydroxy-3-[1-oxo-3-(2-trifluoromethylphenyl)-1,2-dihydroisoquinolin-7-ylamino]propionate.

Still further, specific examples of the compound of the present invention include the compound represented by the following formula and the compounds shown in Table 5:

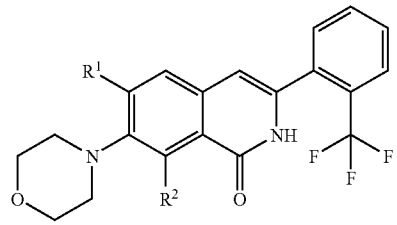

[Formula 8]

However, such examples are not intended to limit the present invention.

TABLE 5

| Compound No. | R¹ | R² | Example |
| --- | --- | --- | --- |
| 157 | Cl | H | Example 157 |
| 158 | H | Cl | Example 158 |
| 159 | Cl | Cl | Example 159 |
| 160 | F | H | Example 160 |
| 161 | H | F | Example 161 |

Compound names corresponding to the aforementioned compound Nos. are described below.

(157): 6-chloro-7-morpholin-4-yl-3-(2-trifluoromethylphenyl)-2H-isoquinolin-1-one, (158): 8-chloro-7-morpholin-4-yl-3-(2-trifluoromethylphenyl)-2H-isoquinolin-1-one, (159): 6,8-dichloro-7-morpholin-4-yl-3-(2-trifluoromethylphenyl)-2H-isoquinolin-1-one, (160): 6-fluoro-7-morpholin-4-yl-3-(2-trifluoromethylphenyl)-2H-isoquinolin-1-one, and (161): 8-fluoro-7-morpholin-4-yl-3-(2-trifluoromethylphenyl)-2H-isoquinolin-1-one.

Next, a method for producing the compound of the present invention will be described. Further, when the defined groups undergo an undesirable chemical conversion under the conditions for carrying out the method in the preparation method as shown below, for example, by using means to protect and deprotect the functional groups, the preparation can be performed. Herein, as the selection of a protective group and the operation of deprotection, for example, the method as described in Greene and Wuts, "Protective Groups in Organic Synthesis" (Second Edition, John Wiley & Sons, 1991)" can be mentioned, and this may be suitably used in accordance with reaction conditions. Further, if necessary or required, the order of the reaction step for introducing a substituent and the like may be changed. As the method for preparing the compound represented by formula (1), various methods can be thought and the compound can be synthesized by using the conventional organic synthesis means and, for example, the compound can be prepared by the following method as a representative method.

Representative Production Methods

Production Method 1

The compound represented by formula (1) of the present invention can be produced by the following method, for example. However, the method for producing the compound of the present invention is not limited thereto. The compounds of the present invention are all novel compounds, which have not been described in any publications. The compounds can be produced by known chemical techniques. As a raw material compound used in production, a commercially available compound can be used. Otherwise, such a compound can also be produced by common methods, as necessary. In the following reaction processes 1 to 4 and the relevant descriptions, X and Y represent $Y^2$ and $Y^3$, and $Y^1$, $Y^2$, $Y^3$ and $Y^4$ have the same definitions as those described in the above formula (1). Moreover, codes used in the following reaction formulas have common means, which can be understood by persons skilled in the art in the present technical field. Furthermore, L represents a chlorine atom or a bromine atom, G represents hydrogen or a $C_{1-4}$ alkyl group such as a methyl group, and T represents a $C_{1-6}$ alkyl group.

1. General Synthesis Methods of Compound (1a) Represented by Formula (1) (Wherein $Y^1$ and $Y^4$ Represent Hydrogen Atoms)
Reaction Process 1

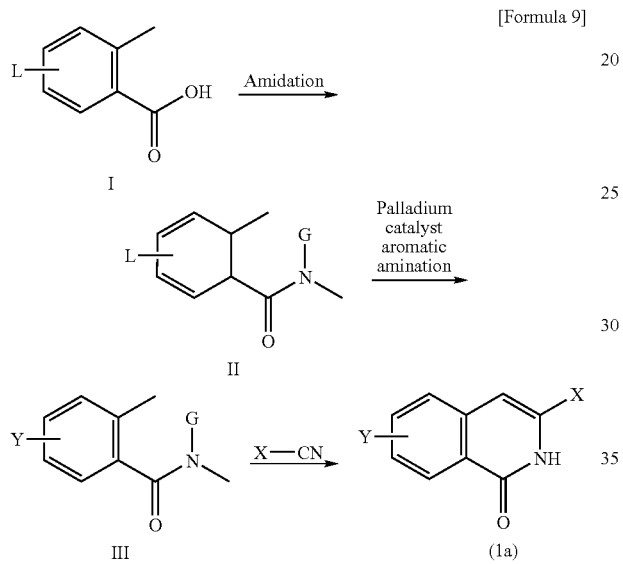

The 2-methylbenzamide derivative II can be easily obtained by applying a common amidation method to the known 2-methylbenzoic acid derivative I. The compound represented by formula III can be produced by isolating and purifying the obtained 2-methylbenzamide derivative II, and then by applying to the resultant derivative a known method (aromatic amination reaction: Wolfe, J. P., J. Org. Chem., 65, 1158-1174 (2000), Harris, M. C., Org. Lett., 4, 2885-2888 (2002), Huang, X., Org. Lett., 3, 3417-3419 (2001)). That is to say, the compound represented by formula III can be produced by allowing the 2-methylbenzamide derivative II to react with a commercially available reagent or a suitable amine prepared by a known method at a suitable temperature (between a room temperature and the boiling point of a solvent) in the presence of a suitable solvent (toluene, THF, 1,4-dioxane, xylene, dimethoxyethane, etc.), a suitable palladium catalyst (for example, $Pd(OAc)_2$, $Pd_2dba_3$, $PdCl_2[P(o-tol)_3]_2$, $Pd(O_2CCF_3)_2$, etc.), a ligand (for example, $P(o-tol)_3$, BINAP, DPPF, $P(t-Bu)_3$, 2-dicyclohexylphosphino-2'-(N,N-dimethylamino)biphenyl, 2-(di-t-butylphosphino)biphenyl, 2-(dicyclohexylphosphino)biphenyl, 2',6'-dimethoxy-2-(dicyclohexylphosphino)biphenyl, 2',4',6'-triisopropyl-2-(dicyclohexylphosphino)biphenyl-1,3-diallyldihydroimidazolium salt, etc.), and a base (for example, t-BuONa, LiHMDS, $Cs_2CO_3$, $K_3PO_4$, etc.). From the obtained compound represented by the formula III, the compound represented by formula (1a) can be produced by applying known methods (U.S. Pat. No. 4,942,163; Won-Jea Cho, et al., Arch. Pharm. Res., 20, 264-268 (1997); Bioorg. Med. Chem. Lett. 8, 41-46 (1998); Arch. Pharm. Res., 24, 276-280 (2001); Bioorg. Med. Chem. 10, 2953-2961 (2002)). That is, the compound represented by formula (1a) can be obtained by subjecting the compound represented by formula III to lithiation with a suitable base (for example, LDA, t-BuLi, s-BuLi, or BuLi) in a suitable solvent (for example, THF or $Et_2O$) at a suitable temperature (for example, between −78° C. and the boiling point of the solvent), and then allowing the resultant to react with a commercially available reagent, or with an aromatic or hetero aromatic nitrile derivative, which has been prepared by a known method, at a suitable temperature (for example, between −78° C. and the boiling point of the solvent).

2. General Synthesis Method of Compound (1b) Represented by Formula (1) (Wherein $Y^1$ and $Y^4$ Represent Hydrogen Atoms)
Reaction Process 2

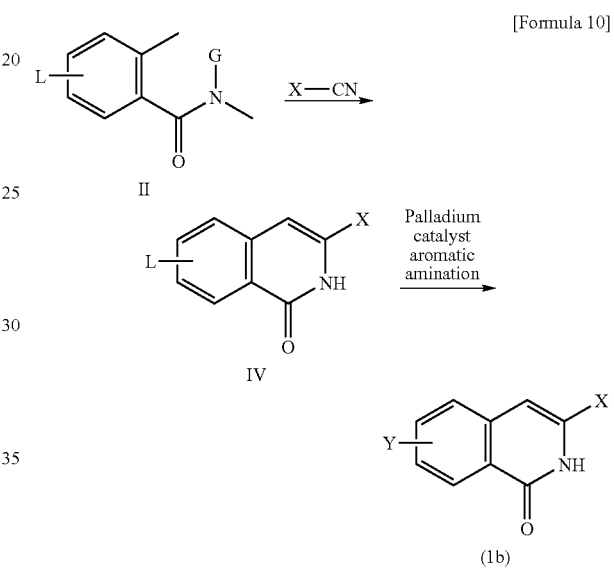

The known methods (U.S. Pat. No. 4,942,163; Won-Jea Cho, et al., Arch. Pharm. Res., 20, 264-268 (1997); Bioorg. Med. Chem. Lett. 8, 41-46 (1998); Arch. Pharm. Res., 24, 276-280 (2001); Bioorg. Med. Chem. 10, 2953-2961 (2002)) are applied to the 2-methylbenzamide derivative II obtained in reaction process 1, so as to obtain the compound represented by formula (IV). In addition, the known methods (aromatic amination reaction: Wolfe, J. P., J. Org. Chem., 65, 1158-1174 (2000); Harris, M. C., Org. Lett., 4, 2885-2888 (2002); Huang, X., Org. Lett., 3, 3417-3419 (2001)) are applied to the compound represented by formula (IV), as in reaction process 1, so as to obtain the compound represented by formula (1b).

3. General Synthesis Method of Compound (1d) Represented by Formula (1) (Wherein $Y^1$ and $Y^4$ Represent Hydrogen Atoms)
Reaction Process 3

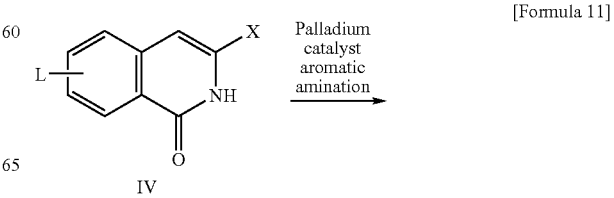

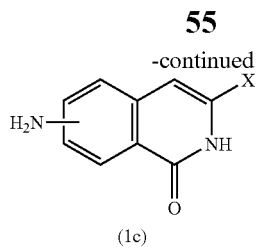

(1c)

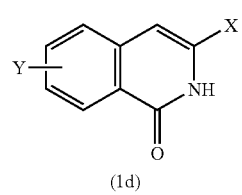

(1d)

The compound represented by formula (1c) can be produced from the compound represented by formula (IV) used in reaction process 2 by known methods (aromatic amination reaction: Wolfe, J. P., J. Org. Chem., 65, 1158-1174 (2000); Harris, M. C., Org. Lett., 4, 2885-2888 (2002); Huang, X., Org. Lett., 3, 3417-3419 (2001)), as in reaction process 2. The compound represented by formula (1d) can be produced from the obtained compound represented by formula (1c) by a known method (for example, a reductive amination reaction).

4. General Synthesis Method of Compound (1e) Represented by Formula (1) (Wherein $Y^1$ and $Y^4$ Represent Hydrogen Atoms)

Reaction Process 4

[Formula 12]

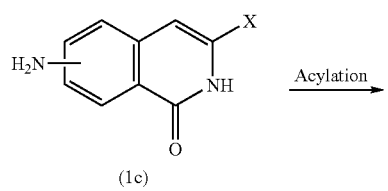

The compound represented by formula (1e) can be produced by subjecting the compound represented by formula (1c) used in reaction process 3 to a common acylation reaction. That is to say, the above compound can be produced by allowing the compound represented by formula (1c) to react with a suitable solvent (toluene, tetrahydrofuran, 1,4-dioxane, xylene dimethoxyethane, diethyl ether, methylene chloride, pyridine, N,N-dimethylformamide, dimethyl sulfoxide, etc.) and a suitable base (for example, triethylamine, pyridine, etc.) in the presence of an acid anhydride or acid halide at a suitable temperature (between −78° C. and the boiling point of the solvent).

5. General Synthesis Method of Compound (1f) Represented by Formula (1) (Wherein $Y^1$ and $Y^4$ Represent Hydrogen Atoms)

Reaction Process 5

[Formula 13]

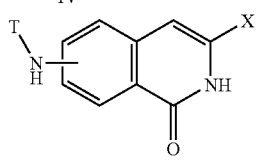

IV

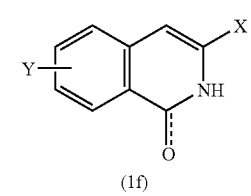

V

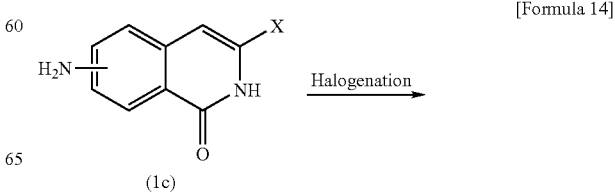

(1f)

The compound represented by formula (V) can be produced by subjecting the compound represented by formula (IV) to a known method (aromatic amination: Fukuyama, T., Org. Lett., 15, 4987-4990 (2003)). Thus, the compound represented by formula (V) can be produced by allowing the compound represented by formula (IV) to react with a commercially available reagent or a suitable amino compound prepared by a known method in the presence of a suitable solvent (N,N-dimethylformamide, dimethyl sulfoxide, etc.) and a suitable copper catalyst (metal copper (powders), copper (I) chloride, copper (I) oxide, copper (II) oxide, copper (II) chloride, copper (II) sulfate, copper (II) acetate, copper (II) acetoacetate, copper (I) iodide, copper (I) trifluoromethanesulfonate, etc.), and a base (cesium acetate, potassium phosphate, potassium carbonate, cesium carbonate, sodium t-butoxide, potassium hexamethyldisilazane, sodium hexamethyldisilazane, phosphazene, etc.), at a suitable temperature (between a room temperature and the boiling point of the solvent). The compound represented by formula (1f) can be produced from the obtained compound represented by formula (V) by the same method as those in reaction processes 3-4.

6. General Synthesis Method of Compound (1g) Represented by Formula (1) (Wherein $Y^1$ and $Y^4$ Represent Hydrogen Atoms)

Reaction Process 6

[Formula 14]

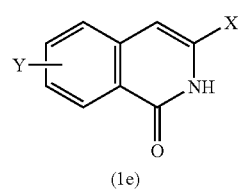

(1c)

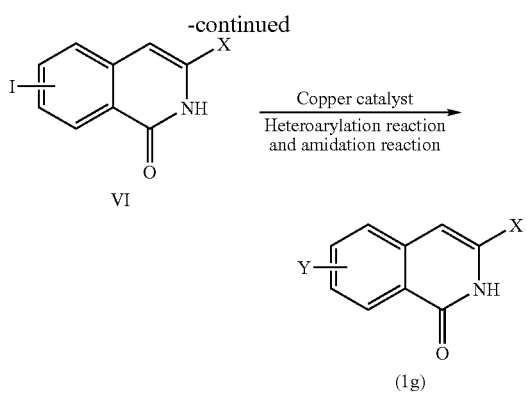

The compound represented by formula (VI) can be easily obtained by subjecting the compound represented by formula (1c) used in reaction process 3 to a halogenation reaction such as Sandmeyer reaction. The compound represented by formula (1g) can be produced by subjecting the compound represented by formula (VI) to a known method (copper catalyst heteroarylation reaction and amidation reaction: Buchwald, S. L., J. Am. Chem. Soc., 123, 7727-7729 (2001), Buchwald, S. L., J. Am. Chem. Soc., 124, 7421-7428 (2002)). Thus, the compound represented by formula (1g) can be produced by allowing the compound represented by formula (VI) to react with a commercially available reagent or a suitable heteroaromatic compound or amide compound prepared by a known method in the presence of a suitable solvent (dioxane, tetrahydrofuran, diethyl ether, toluene, etc.), a suitable copper catalyst (metal copper (powders), copper (I) chloride, copper (I) oxide, copper (II) oxide, copper (II) chloride, copper (II) sulfate, copper (II) acetate, copper (II) acetoacetate, copper (I) iodide, copper (I) trifluoromethanesulfonate, etc.), a ligand (1,2-cyclohexanediamine, N,N'-dimethylethylenediamine, N,N'-dimethyl-1,2-cyclohexanediamine, 1,10-phenanthroline, etc.), and a base (potassium phosphate, potassium carbonate, cesium carbonate, sodium t-butoxide, potassium hexamethyldisilazane, sodium hexamethyldisilazane, phosphazene, etc.), at a suitable temperature (between a room temperature and the boiling point of the solvent).

7. General Synthesis Method of Compound (1j) Represented by Formula (1) (Wherein $Y^1$ and $Y^4$ Independently Represent a Hydrogen Atom or a Halogen Atom)

Reaction Process 7

[Formula 15]

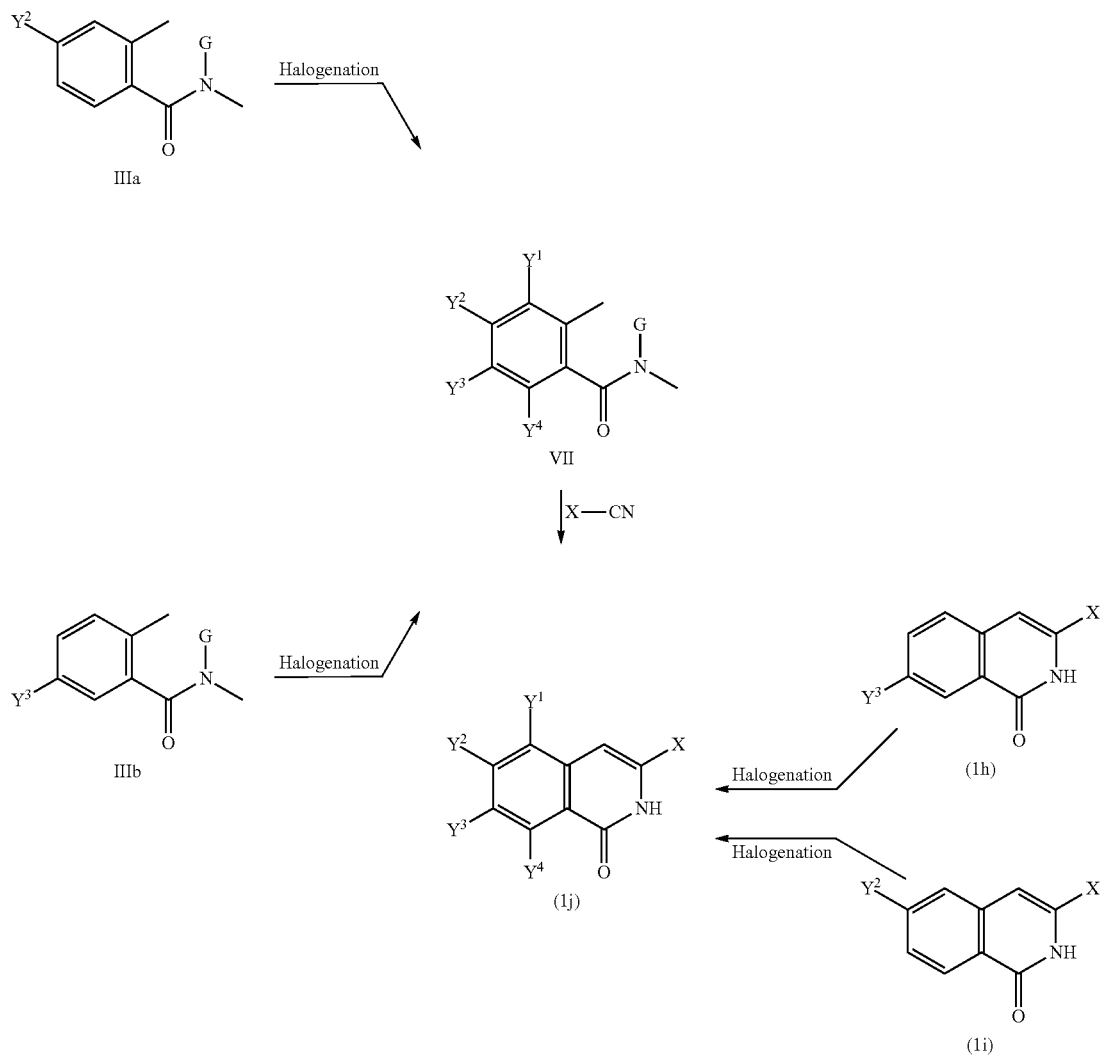

The compound represented by formula (VII) can be produced by subjecting the 2-methylbenzamide derivative III obtained in reaction process 1 to a known method (halogenation; J. Org. Chem., 63(10), 3379-3385 (1998), Heterocycles, 29(4), 649-651 (1989)). Thus, the compound represented by formula (VII) can be produced by allowing the 2-methylbenzamide derivative III to react with a halogenation reagent (N,N'-difluoro-2,2'-bipyridium bis(tetrafluoroborate), N-chlorosuccinimide, etc.) in a suitable solvent (acetonitrile, methylene chloride, etc.) at a suitable temperature (between −78° C. and the boiling point of the solvent). The compound represented by formula (1j) can be produced by subjecting the obtained compound represented by formula (VII) to the known methods used in reaction process 1 (U.S. Pat. No. 4,942,163; Won-Jea Cho, et al., Arch. Pharm. Res., 20, 264-268 (1997); Bioorg. Med. Chem. Lett. 8, 41-46 (1998); Arch Pharm. Res., 24, 276-280 (2001); Bioorg. Med. Chem. 10, 2953-2961 (2002)). In addition, it is considered that the above compound can also be produced by subjecting the compound represented by formula (1h) or (1i) synthesized in reaction processes 1 to 4 to a known method (halogenation: J. Org. Chem., 63(10), 3379-3385 (1998), Heterocycles, 29(4), 649-651 (1989)).

Synthesis of Raw Material Compounds

Several raw material compounds for the compound of the present invention are novel compounds. Such novel compounds can be easily synthesized in the same manner as for known raw material compounds, or by applying methods known to persons skilled in the art.

Examples of a method for producing the compound represented by formula (1) of the present invention have been given above. Isolation and purification of the compounds of interest shown in the aforementioned reaction processes can be carried out by applying common chemical operations such as extraction, concentration, distillation, crystallization, filtration, recrystallization, or various types of chromatography.

The compound of the present invention and a pharmaceutically acceptable salt thereof include all stereoisomers of the compound represented by formula (1) (for example, an enantiomer and a diastereomer (including cis- and trans-geometric isomers)), racemate of the aforementioned isomers, and other mixtures.

In addition, the compound of the present invention and a pharmaceutically acceptable salt thereof can be present in several tautomeric forms, such as enol and imine forms, keto and enamine forms, and mixtures thereof. Such tautomeric isomers are present in a solution in the form of a mixture of tautomeric sets. In a solid form, either one tautomeric isomer is generally dominant. There are cases where only either one tautomeric isomer is described, but the present invention includes all tautomeric isomers of the compound of the present invention.

When the compound of the present invention is obtained as a free form, it can be converted into a salt, which the above compound may form, a hydrate thereof, or a solvate thereof, according to a common method.

In addition, when the compound of the present invention is obtained in the form of such a salt, hydrate, or solvate of the above compound, they can be converted to a free form of the compound according to a common method.

The compound of the present invention or a pharmaceutically acceptable salt thereof has excellent antitumor action. It is excellent in terms of stability in vivo and solubility in water, and is useful as a preventive or therapeutic agent (particularly as a therapeutic agent) used for proliferative diseases. Moreover, the compound of the present invention or a pharmaceutically acceptable salt is useful as a preventive or therapeutic agent (particularly as a therapeutic agent) used for proliferative diseases including various types of cancers such as breast cancer, colon cancer, ovarian cancer, lung cancer, pancreatic cancer, liver cancer, uterine cancer, brain tumor, prostatic cancer, acute leukemia, and stomach cancer.

The aforementioned methods include a step of administering to patients, who need such treatment or who suffer from the aforementioned diseases or symptoms, a pharmaceutical composition comprising the compound disclosed in the present invention or a pharmaceutically acceptable salt thereof, at a pharmaceutically effective dosage.

When the pharmaceutical composition of the present invention is used as a therapeutic or preventive agent for proliferative diseases such as cancer, examples of an administration method may include oral, intrarectal, parenteral (intravenous, intramuscular, or subcutaneous), intracisternal, intravaginal, intraperitoneal, intravesical, and local (administration of drop, powders, ointment, gel or cream) administrations, and inhalation (intraoral or nasal spray). Examples of such an administration form may include a tablet, a capsule, a granule, a powder, a pill, an aqueous or nonaqueous oral solution or suspension, and a parenteral solution, which is filled in a container suitable for dividing the solution into individual dosages. In addition, such an administration form can also be adapted to various administration methods including controlled released preparations such as those used in subcutaneous transplantation.

The aforementioned pharmaceutical can be produced according to known methods using additives such as an excipient, a lubricant (coating agent), a binder, a disintegrator, a stabilizer, a flavoring agent, or a diluent.

Examples of an excipient may include starches such as starch, potato starch, or corn starch, lactose, crystalline cellulose, and calcium hydrogen phosphate.

Examples of a coating agent may include ethyl cellulose, hydroxypropylcellulose, hydroxypropylmethylcellulose, shellac, talc, carnauba wax, and paraffin.

Examples of a binder may include polyvinylpyrrolidone, macrogol, and the same compounds as those described in the above excipient.

Examples of a disintegrator may include the same compounds as those described in the above excipient, and chemically modified starches and celluloses, such as croscarmellose sodium, carboxymethyl starch sodium, or crosslinked polyvinylpyrrolidone.

Examples of a stabilizer may include: p-hydroxybenzoic esters such as methylparaben or propylparaben; alcohols such as chlorobutanol, benzyl alcohol, or phenylethyl alcohol; benzalkonium chloride; phenols such as phenol or cresol; thimerosal; dehydroacetic acid; and sorbic acid.

Examples of a flavoring agent may include commonly used sweeteners, acidulants, and aromatics.

Examples of a solvent used in production of a liquid agent may include ethanol, phenol, chlorocresol, purified water, and distilled water.

Examples of a surfactant or emulsifier may include polysorbate 80, polyoxyl 40 stearate, and lauromacrogol.

When the pharmaceutical composition of the present invention is used as a therapeutic or preventive agent for proliferative diseases, the amount used of the compound of the present invention or a pharmaceutically acceptable salt thereof is different depending on symptom, age, body weight, relative physical conditions, the use of other agents, an administration method, etc. For example, for a patient (a hematherm, and particularly a human), in the case of administering an active ingredient (the compound represented by formula (1) of the present invention) as an oral agent, an effective amount is generally preferably 0.01 and 1,000 mg, and more preferably between 0.1 and 300 mg per kg of body weight per day. The dose per day for an adult patient with a normal body weight is preferably between 1 and 5,000 mg. In the case of a parenteral agent, such an effective amount is preferably between 0.01 and 1,000 mg, and more preferably between 1 and 5,000 mg per kg of body weight per day. It is desired that such an amount of pharmaceutical composition be administered depending on symptoms.

EXAMPLES

The present invention will be more specifically described in the following examples. However, these examples are not intended to limit the scope of the present invention. It is to be noted that NMR analysis was carried out using JNM-EX270 (270 MHz), JNMGSX400 (400 MHz) or JNM-A500 (500 MHz), which are manufactured by JEOL. NMR data was indicated with ppm (parts per million). The deuterium lock signal from a sample solvent was referred. Mass spectrum data was obtained using JMS-DX303 or JMS-SX/SX102A manufactured by JEOL. In addition, mass spectrum data including high performance liquid chromatography was obtained, using a micromass (ZMD manufactured by Micromass) equipped with a 996-600E gradient high performance liquid chromatography manufactured by Waters, or using a micromass (ZQ manufactured by Micromass) equipped with a 2525 gradient high performance liquid chromatography manufactured by Waters. Any of the following conditions were applied for such high performance liquid chromatography.

High Performance Liquid Chromatography Condition 1
Column: Combi ODS (ODS, 5 μm, 4.6 mm I.D.×50 mm, manufactured by Wako Pure Chemical Industries, Ltd.), COSMOSIL (ODS, 5 μm, 4.6 mm I.D.×50 mm, manufactured by Nacalai Tesque, Inc.), or Inertsil C18 (ODS, 5 μm, 4.6 mm I.D.×50 mm, manufactured by GL Sciences, Inc)
Mobile phase: Water (A) that contains 0.05% trifluoroacetic acid and acetonitrile (B) that contains 0.05% trifluoroacetic acid
Elution method: A stepwise solvent gradient elution comprising eluting from 10% B to 95% B (3.5 minutes), eluting from 95% B to 10% B (1 minute), and then retaining at 10% B (0.5 minute)
Flow rate: 4.0 ml/minute
High Performance Liquid Chromatography Condition 2
Column: Combi ODS (ODS, 5 μm, 4.6 mm I.D.×50 mm, manufactured by Wako Pure Chemical Industries, Ltd.), COSMOSIL (ODS, 5 μm, 4.6 mm I.D.×50 mm, manufactured by Nacalai Tesque, Inc.), or Inertsil C18 (ODS, 5 μm, 4.6 mm I.D.×50 mm, manufactured by GL Sciences, Inc)
Mobile phase: Water (A) that contains 0.05% trifluoroacetic acid and acetonitrile (B) that contains 0.05% trifluoroacetic acid
Elution method: A stepwise solvent gradient elution comprising eluting from 30% B to 35% B (0.2 minute), eluting from 35% B to 98% B (3.3 minutes), eluting from 98% B to 30% B (1 minute), and then retaining at 30% B (0.5 minute)
Flow rate: 4.0 ml/minute
High Performance Liquid Chromatography Condition 3
Column: Combi ODS (ODS, 5 μm, 4.6 mm I.D.×50 mm, manufactured by Wako Pure Chemical Industries, Ltd.)
Mobile phase: Water (A) that contains 0.05% trifluoroacetic acid and acetonitrile (B) that contains 0.05% trifluoroacetic acid
Elution method: A stepwise solvent gradient elution comprising eluting from 10% B to 95% B (2 minutes), retaining at 95% B (1.5 minutes), eluting from 95% B to 10% B (1 minute), and retaining at 10% B (0.5 minute)
Flow rate: 4.0 ml/minute An organic synthetic reaction was carried out using a commercially available reagent, which has not been further purified before use. The term "room temperature" is used herein to mean a temperature ranging from about 20° C. to 25° C. All antiposic reactions were carried out in a nitrogen atmosphere. Concentration under reduced pressure or solvent distillation was carried out using a rotary evaporator, unless otherwise specified.

For preparation of compounds, a functional group is protected by a protecting group as necessary, a protector of a target molecule is prepared, and the protecting group is then removed. Operations to select such a protecting group and to remove it were carried out according to the method described in Greene and Wuts, "Protective Group in Organic Synthesis," $2^{nd}$ edition, John Wiley & Sons, 1991, for example.

Example 1

7-Chloro-3-(2-trifluoromethylphenyl)-2H-isoquinolin-1-one

Step A

5-Chloro-2,N-dimethylbenzamide

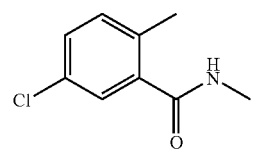

[Formula 16]

42.8 ml of thionyl chloride (586 mmol) was added to 25.0 g of 5-chloro-2-methylbenzoic acid (147 mmol). The mixture was stirred under heating to reflux for 1.5 hours. Thereafter, excessive thionyl chloride was distilled away under reduced pressure. The residue was dissolved in 140 ml of methylene chloride, and 34.2 ml (440 mmol) of a 40% methylamine aqueous solution was then added dropwise thereto under cooling on ice. Thereafter, the obtained mixture was stirred at 0° C. over a day and a night. Thereafter, the reaction solution was extracted with ethyl acetate, and the extract was then washed with a saturated saline solution. The resultant was then dried over anhydrous sodium sulfate, and the solvent was then distilled away under reduced pressure. The obtained residue was purified by silica gel column chromatography (ethyl acetate:hexane=1:3 to 3:2), so as to obtain 24.2 g (90%) of 5-chloro-2,N-dimethylbenzamide in the form of a colorless solid.

$^1$H-NMR (270 MHz, CDCl$_3$) δ (ppm): 2.40 (3H, s), 2.99 (3H, d, J=4.6 Hz), 5.77 (1H, brs), 7.15 (1H, d, J=8.3 Hz), 7.27 (1H, dd, J=2.3, 8.3 Hz), 7.33 (1H, d, J=2.3 Hz)

ESI (LC-MS positive mode) m/z 184 (M+H).

Step B

7-Chloro-3-(2-trifluoromethylphenyl)-2H-isoquinolin-1-one

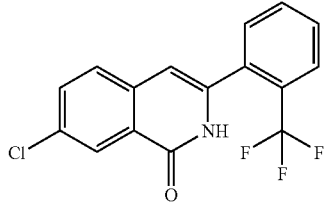

[Formula 17]

45.3 ml of a 1.8 M lithium diisopropylamide THF solution (81.6 mmol) was diluted with 68 ml of THF. Thereafter, 28 ml of a THF solution containing 5.0 g (27.2 mmol) of the 5-chloro-2,N-dimethylbenzamide prepared in Step A was added dropwise to the diluted solution at −78° C. Thereafter, 28 ml of a THF solution containing 4.65 g (27.2 mmol) of 2-trifluoromethylbenzonitrile was further added thereto, and the obtained mixture was then stirred at −78° C. for 2.5 hours. The temperature of the reaction solution was increased to a room temperature, and a saturated ammonium chloride aqueous solution was added thereto, followed by extraction with ethyl acetate. The extract was washed with a saturated saline solution, and was then dried over anhydrous sodium sulfate. Thereafter, a solid generated as a result of vacuum concentration was filtrated, so as to obtain 6.87 g (78%) of 7-chloro-3-(2-trifluoromethylphenyl)-2H-isoquinolin-1-one in the form of a colorless solid.

$^1$H-NMR (270 MHz, CDCl$_3$) δ (ppm): 6.49 (1H, s), 7.33-7.72 (5H, m), 7.81-7.84 (1H, d, J=7.26 Hz), 8.32-8.33 (1H, d, J=1.65 Hz), 9.18 (1H, brs)

ESI (LC-MS positive mode) m/z 324 (M+H).

The following compounds (Examples 2 and 3) were synthesized by a method similar to that in Step B of Example 1.

Example 2

7-Chloro-3-phenyl-2H-isoquinolin-1-one

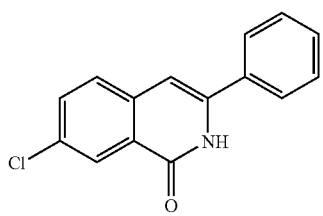

[Formula 18]

$^1$H-NMR (270 MHz, CDCl$_3$) δ (ppm): 6.74 (1H, s), 7.26-7.56 (4H, m), 7.61-7.66 (3H, m), 8.28 (1H, d, J=2.3 Hz), 9.02 (1H, brs)

ESI (LC-MS positive mode) m/z 256 (M+H).

Example 3

7-Chloro-3-(2-trifluoromethoxyphenyl)-2H-isoquinolin-1-one

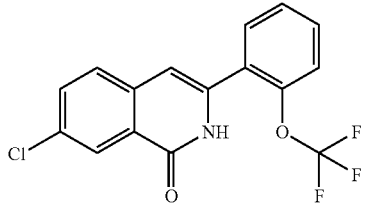

[Formula 19]

$^1$H-NMR (270 MHz, DMSO-d$_6$) δ (ppm): 6.72 (1H, s), 7.51-7.56 (2H, m), 7.59-7.70 (2H, m), 7.78 (1H, s), 7.79 (1H, s), 8.15 (1H, s), 11.81 (1H, s)

ESI (LC-MS positive mode) m/z 340 (M+H).

Example 4

7-Pyrrolidin-1-yl-3-(2-trifluoromethylphenyl)-2H-isoquinolin-1-one

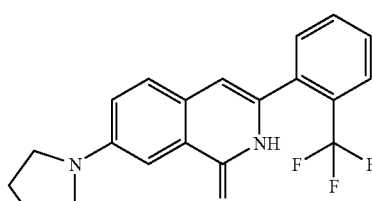

[Formula 20]

A mixture consisting of 500 mg (1.54 mmol) of the 7-chloro-3-(2-trifluoromethylphenyl)-2H-isoquinolin-1-one prepared in Step B of Example 1; 45.0 mg (0.15 mmol) of 2-(di-t-butylphosphino)biphenyl; 17.0 mg (0.075 mmol) of palladium acetate; and 713 mg (7.42 mmol) of sodium t-butoxide, was suspended in 15 ml of toluene. Thereafter, 0.533 ml (6.39 mmol) of pyrrolidine was added to the above suspension, and the obtained mixture was then stirred under heating to reflux for 2 hours. Thereafter, the reaction solution was stood to cool, and water was then added thereto, followed by extraction with ethyl acetate. The extract was dried over anhydrous sodium sulfate, and was then concentrated. The obtained residue was purified by silica gel column chromatography (ethyl acetate:hexane=1:5), so as to obtain 277.9 mg (50%) of 7-pyrrolidin-1-yl-3-(2-trifluoromethylphenyl)-2H-isoquinolin-1-one in the form of a yellow solid.

$^1$H-NMR (270 MHz, CDCl$_3$) δ (ppm): 2.04-2.09 (4H, m), 3.40-3.45 (4H, m), 6.44 (1H, s), 7.00-7.04 (1H, dd, J=2.6, 8.6 Hz), 7.42-7.67 (5.5H, m), 7.78-7.81 (1H, d, J=7.9 Hz), 8.29 (0.5H, brs)

EI-MS m/z 358 (M$^+$).

The following compounds (Examples 5 to 16) were synthesized by a method similar to that of Example 4, using the compound obtained in Example 1, 2, or 3, as a starting material.

Example 5

3-Phenyl-7-pyrrolidin-1-yl-2H-isoquinolin-1-one

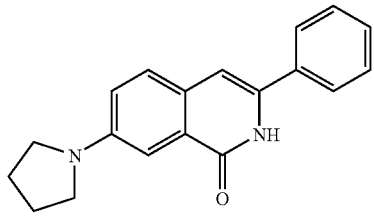

[Formula 21]

¹H-NMR (270 MHz, CDCl₃) δ (ppm): 2.02-2.12 (4H, m), 3.40-3.45 (4H, m), 6.73 (1H, s), 7.02 (1H, dd, J=2.6, 8.9 Hz), 7.37-7.51 (5H, m), 7.59-7.65 (2H, m), 8.83 (1H, brs)
ESI (LC-MS positive mode) m/z 291 (M+H).

Example 6

7-Pyrrolidin-1-yl-3-(2-trifluoromethoxyphenyl)-2H-isoquinolin-1-one

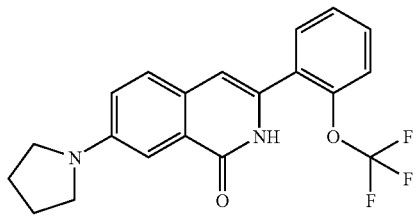

[Formula 22]

¹H-NMR (270 MHz, CDCl₃) δ (ppm): 2.00-2.11 (4H, m), 3.39-3.47 (4H, m), 6.64 (1H, s), 7.02 (1H, dd, J=2.6, 8.6 Hz), 7.37-7.50 (5H, m), 7.57-7.61 (1H, m), 8.60 (1H, brs)
ESI (LC-MS positive mode) m/z 375 (M+H).

Example 7

7-Morpholin-4-yl-3-(2-trifluoromethylphenyl)-2H-isoquinolin-1-one

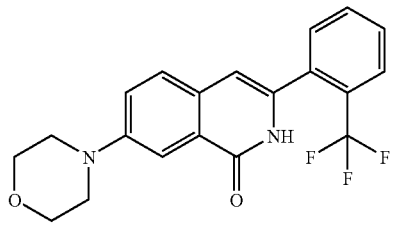

[Formula 23]

¹H-NMR (500 MHz, CDCl₃) δ (ppm): 3.30-3.32 (4H, m), 3.89-3.91 (4H, m), 6.46 (1H, s), 7.35-7.37 (1H, dd, J=2.3, 8.7 Hz), 7.49-7.51 (1H, d, J=8.7 Hz), 7.53-7.67 (3H, m), 7.79-7.81 (2H, m), 8.54 (1H, brs)
EI-MS m/z 374 (M⁺).

Example 8

7-Morpholin-4-yl-3-phenyl-2H-isoquinolin-1-one

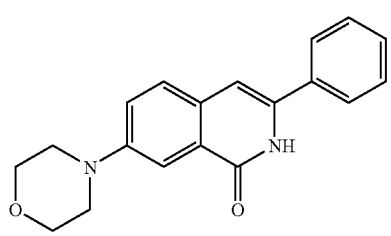

[Formula 24]

¹H-NMR (270 MHz, CDCl₃) δ (ppm): 3.31 (4H, t, J=4.8 Hz), 3.91 (4H, t, J=4.8 Hz), 6.73 (1H, s), 7.36 (1H, dd, J=2.6, 8.9 Hz), 7.41-7.64 (6H, m), 7.79 (1H, d, J=2.6 Hz), 8.84 (1H, brs)
ESI (LC-MS positive mode) m/z 307 (M+H).

Example 9

7-Morpholin-4-yl-3-(2-trifluoromethoxyphenyl)-2H-isoquinolin-1-one

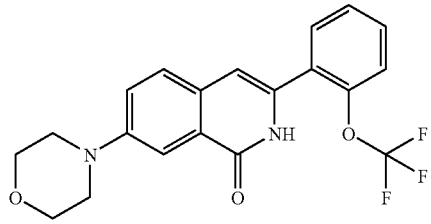

[Formula 25]

¹H-NMR (270 MHz, CDCl₃) δ (ppm): 3.32 (4H, m), 3.90 (4H, m), 6.65 (1H, brs), 7.35-7.65 (6H, m), 7.80 (1H, d, J=2.6 Hz), 8.60 (1H, brs)
ESI (LC-MS positive mode) m/z 391 (M+H).

Example 10

7-Piperidin-1-yl-3-(2-trifluoromethylphenyl)-2H-isoquinolin-1-one

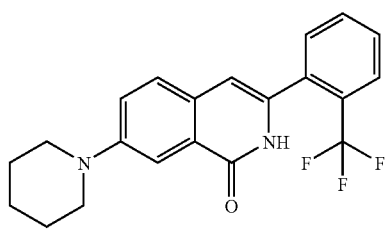

[Formula 26]

¹H-NMR (270 MHz, CDCl₃) δ (ppm): 1.59-1.74 (6H, m), 3.31-3.35 (4H, m), 6.44 (1H, s), 7.36-7.65 (5H, m), 7.80-7.81 (2H, m), 8.37 (1H, brs)
EI-MS m/z 372 (M⁺).

Example 11

3-Phenyl-7-piperidin-1-yl-2H-isoquinolin-1-one

[Formula 27]

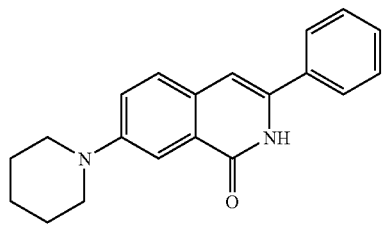

$^1$H-NMR (270 MHz, CDCl$_3$) δ (ppm): 1.55-1.80 (6H, m), 3.33 (4H, t, J=5.4 Hz), 6.71 (1H, s), 7.37 (1H, dd, J=2.7, 8.9 Hz), 7.40-7.55 (4H, m), 7.59-7.64 (2H, m), 7.79 (1H, d, J=2.7 Hz), 8.65 (1H, brs)
ESI (LC-MS positive mode) m/z 305 (M+H).

Example 12

7-Piperidin-1-yl-3-(2-trifluoromethoxyphenyl)-2H-isoquinolin-1-one

[Formula 28]

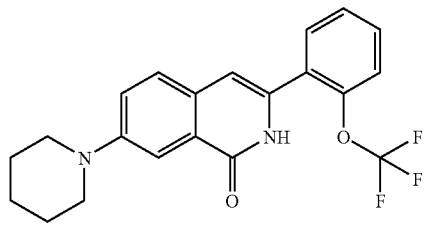

$^1$H-NMR (400 MHz, CDCl$_3$) δ (ppm): 1.62-1.66 (2H, m), 1.71-1.77 (4H, m), 3.33 (4H, t, J=5.4 Hz), 6.62 (1H, s), 7.36-7.58 (5H, m), 7.59 (1H, dd, J=2.0, 7.2 Hz), 7.80 (1H, d, J=2.4 Hz), 8.73 (1H, brs)
ESI (LC-MS positive mode) m/z 389 (M+H).

Example 13

7-(4-Methylpiperazin-1-yl)-3-phenyl-2H-isoquinolin-1-one

[Formula 29]

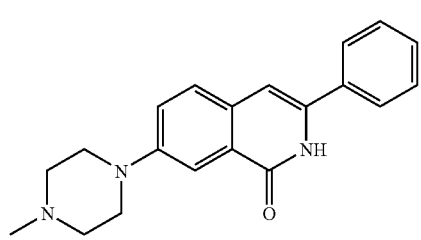

$^1$H-NMR (270 MHz, CDCl$_3$) δ (ppm): 2.38 (3H, s), 2.62 (4H, t, J=4.8 Hz), 3.38 (4H, t, J=4.8 Hz), 6.73 (1H, s), 7.35-7.54 (5H, m), 7.62-7.65 (2H, m), 8.00 (1H, d, J=2.6 Hz), 9.09 (1H, brs)
ESI (LC-MS positive mode) m/z 320 (M+H).

Example 14

7-(Benzylmethylamino)-3-phenyl-2H-isoquinolin-1-one

[Formula 30]

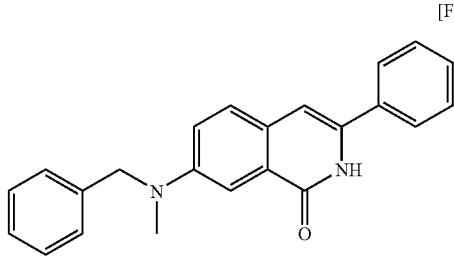

$^1$H-NMR (270 MHz, CDCl$_3$) δ (ppm): 3.15 (3H, s), 4.67 (2H, s), 6.73 (1H, s), 7.10-7.55 (10H, m), 7.57-7.70 (3H, m), 9.19 (1H, brs)
ESI (LC-MS positive mode) m/z 341 (M+H).

Example 15

7-(2-Morpholin-4-ylethylamino)-3-phenyl-2H-isoquinolin-1-one

[Formula 31]

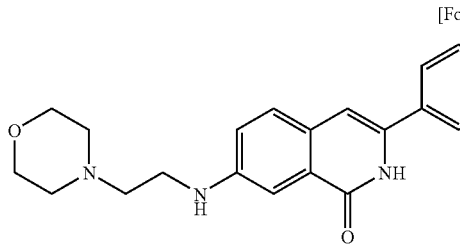

$^1$H-NMR (270 MHz, CDCl$_3$) δ (ppm): 2.50 (4H, t, J=4.6 Hz), 2.69 (2H, t, J=5.8 Hz), 3.31 (2H, m), 3.74 (4H, t, J=4.6 Hz), 4.71 (1H, brs), 6.71 (1H, s), 7.06 (1H, dd, J=2.3, 8.6 Hz), 7.38-7.51 (5H, m), 7.60-7.63 (2H, m), 8.94 (1H, brs)
ESI (LC-MS positive mode) m/z 350 (M+H).

Example 16

7-(2-Morpholin-4-ylethylamino)-3-(2-trifluoromethoxyphenyl)-2H-isoquinolin-1-one

[Formula 32]

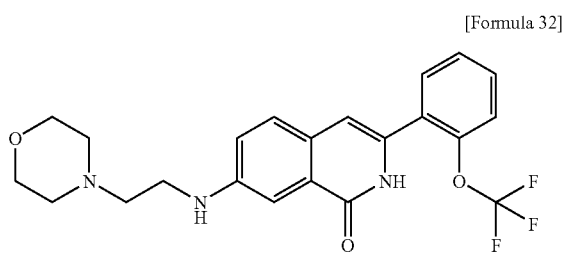

¹H-NMR (400 MHz, CDCl₃) δ (ppm): 2.50 (4H, brs), 2.69 (2H, t, J=6.0 Hz), 3.31 (2H, q, J=4.2 Hz), 3.74 (4H, t, J=4.6 Hz), 4.73 (1H, brs), 6.62 (1H, s), 7.06 (1H, dd, J=2.8, 8.4 Hz), 7.37-7.50 (5H, m), 7.58 (1H, dd, J=1.8, 7.4 Hz), 8.64 (1H, brs)
ESI (LC-MS positive mode) m/z 434 (M+H).

Example 17

7-[Methyl(2-morpholin-4-ylethyl)amino]-3-phenyl-2H-isoquinolin-1-one

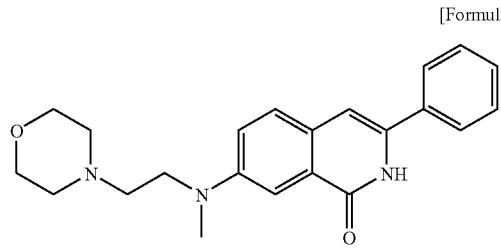

[Formula 33]

0.05 ml of acetic acid and 13.2 mg (0.168 mmol) of sodium cyanoborohydride were added to 0.5 ml of a methanol solution containing 14.7 mg (0.0241 mmol) of the 7-(2-morpholin-4-ylethylamino)-3-phenyl-2H-isoquinolin-1-one obtained in Example 15. The obtained mixture was stirred at a room temperature for 6 hours. Thereafter, a saturated sodium bicarbonate aqueous solution was added to the reaction solution, and the mixture was then extracted with ethyl acetate. The extract was dried over anhydrous sodium sulfate, and was then concentrated under reduced pressure. The obtained residue was purified by silica gel column chromatography (methylene chloride:methanol=20:1), so as to obtain 12.8 mg (84%) of 7-[methyl(2-morpholin-4-ylethyl)amino]-3-phenyl-2H-isoquinolin-1-one in the form of a yellow solid.
¹H-NMR (270 MHz, CDCl₃) δ (ppm): 2.52 (4H, t, J=4.6 Hz), 2.59 (2H, t, J=7.3 Hz), 3.10 (3H, s), 3.61 (2H, t, J=7.3 Hz), 3.72 (4H, t, J=4.6 Hz), 6.73 (1H, s), 7.19 (1H, dd, J=2.8, 8.7 Hz), 7.38-7.66 (7H, m), 9.10 (1H, brs)
ESI (LC-MS positive mode) m/z 364 (M+H).

Example 18

7-[Methyl(2-morpholin-4-ylethyl)amino]-3-(2-trifluoromethoxyphenyl)-2H-isoquinolin-1-one

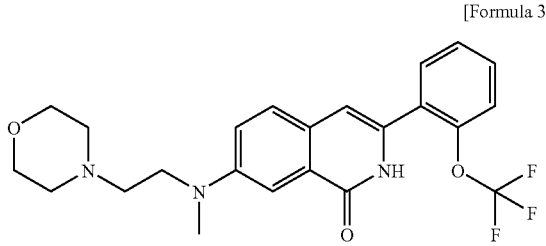

[Formula 34]

The above compound was synthesized via a reaction similar to that of Example 17, using the 7-[methyl(2-morpholin-4-ylethyl)amino]-3-(2-trifluoromethoxyphenyl)-2H-isoquinolin-1-one obtained in Example 16 as a starting material.

¹H-NMR (270 MHz, CDCl₃) δ (ppm): 2.52 (4H, t, J=4.4 Hz), 2.59 (2H, t, J=7.2 Hz), 3.10 (3H, s), 3.61 (2H, t, J=7.0 Hz), 3.72 (4H, t, J=4.6 Hz), 6.63 (1H, s), 7.18 (1H, dd, J=2.8, 8.8 Hz), 7.37-7.50 (4H, m), 7.57-7.60 (2H, m), 8.65 (1H, s)
ESI (LC-MS positive mode) m/z 448 (M+H).

Example 19

7-[Methyl-(2-morpholin-4-ylethyl)amino]-3-(2-trifluoromethylphenyl)-2H-isoquinolin-1-one

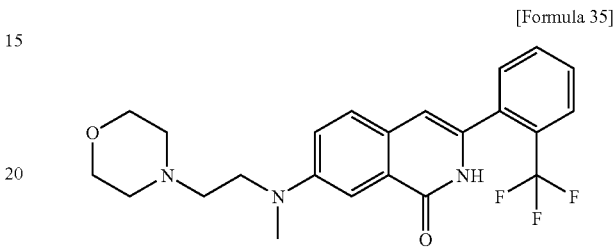

[Formula 35]

The above compound was synthesized by performing a reaction similar to that of Example 17, after performing a reaction similar to that of Example 4.
¹H-NMR (270 MHz, CDCl₃) δ (ppm): 2.51-2.61 (6H, m), 3.10 (3H, s), 3.59-3.64 (2H, m), 3.70-3.74 (4H, m), 6.44 (1H, s), 7.16-7.21 (1H, dd, J=3.0, 8.9 Hz), 7.44-7.47 (1H, d, J=8.91 Hz), 7.52-7.67 (4H, m), 7.78-7.81 (1H, m), 8.32 (1H, brs)
ESI (LC-MS positive mode) m/z 432 (M+H).

Example 20

7-(4-Hydroxymethylpiperidin-1-yl)-3-(2-trifluoromethylphenyl)-2H-isoquinolin-1-one

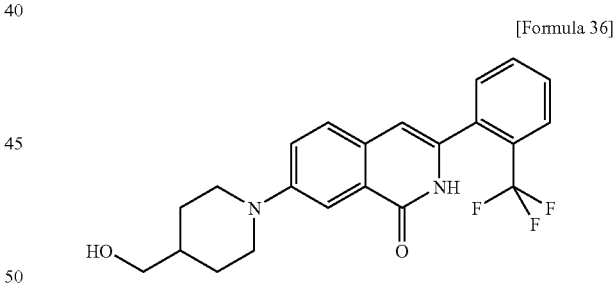

[Formula 36]

8.65 ml (8.65 mmol) of a 1 M lithium bis(trimethylsilyl)amide THF solution was added to a mixture consisting of 400 mg (1.24 mmol) of the 7-chloro-3-(2-trifluoromethylphenyl)-2H-isoquinolin-1-one obtained in Step B of Example 1; 427.2 mg (3.708 mmol) of 4-piperidinemethanol; 29.2 mg (0.074 mmol) of 2-dicyclohexylphosphino-2'-(N,N-dimethylamino)biphenyl; and 28.3 mg (0.0309 mmol) of tris(dibenzylideneacetone)dipalladium. The obtained mixture was stirred under heating to reflux over a day and a night. Thereafter, the reaction solution was cooled to a room temperature, and a saturated ammonium chloride aqueous solution was then added thereto, followed by extraction with methylene chloride. Thereafter, the extract was washed with a saturated saline solution, and was then dried over anhydrous sodium sulfate. The extract was concentrated, and the obtained residue was then purified by silica gel column chromatography (methylene chloride:methanol=25:1 to 20:1), so as to obtain 355.6 mg (71%) of 7-(4-hydroxymethylpiperidin-1-yl)-3-(2-trifluoromethylphenyl)-2H-isoquinolin-1-one in the form of a brown solid.

$^1$H-NMR (270 MHz, DMSO-$d_6$) δ (ppm): 1.27 (2H, dq, J=3.5, 12.1 Hz), 1.49-1.67 (1H, m), 1.72-1.83 (2H, m), 2.76 (2H, dt, J=2.0, 12.2 Hz), 3.25-3.35 (2H, m), 3.78-3.89 (2H, m), 4.51 (1H, t, J=5.3 Hz), 6.37 (1H, s), 7.43-7.60 (4H, m), 7.61-7.80 (2H, m), 7.85 (1H, d, J=7.6 Hz), 11.38 (1H, brs)

ESI (LC-MS positive mode) m/z 403 (M+H).

The following compounds (Examples 21 to 37) were synthesized by a method similar to that of Example 20, using the compound obtained in Example 1, 2, or 3, as a starting material.

Example 21

7-(4-Hydroxymethylpiperidin-1-yl)-3-phenyl-2H-isoquinolin-1-one

[Formula 37]

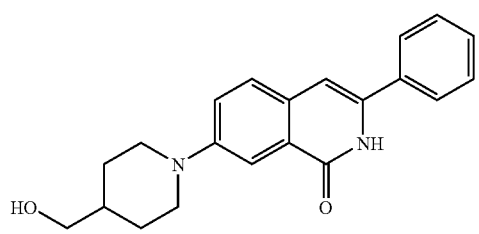

$^1$H-NMR (270 MHz, CDCl$_3$) δ (ppm): 1.43 (2H, dq, J=4.0, 12.2 Hz), 1.48-1.56 (1H, m), 1.63-1.81 (1H, m), 1.90 (2H, d, J=14.2 Hz), 2.86 (2H, dt, J=2.3, 12.2 Hz), 3.45-3.65 (2H, m), 3.86-3.96 (2H, m), 6.73 (1H, s), 7.38 (1H, dd, J=2.6, 8.9 Hz), 7.42-7.53 (4H, m), 7.63-7.69 (2H, m), 7.81 (1H, d, J=2.6 Hz), 9.08 (1H, brs)

ESI (LC-MS positive mode) m/z 335 (M+H).

Example 22

7-(4-Hydroxymethylpiperidin-1-yl)-3-(2-trifluoromethoxyphenyl)-2H-isoquinolin-1-one

[Formula 38]

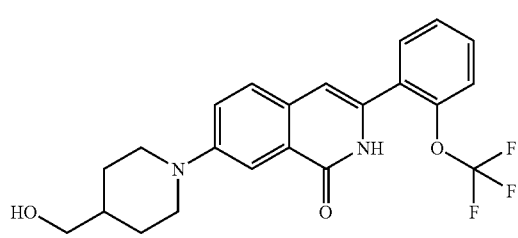

$^1$H-NMR (270 MHz, CDCl$_3$) δ (ppm): 1.25-1.48 (3H, m), 1.74 (1H, m), 1.89 (2H, d, J=13.2 Hz), 2.87 (2H, dt, J=2.4, 12.2 Hz), 3.57 (2H, t, J=5.4 Hz), 3.93 (2H, d, J=12.7 Hz), 6.33 (1H, s), 7.37-7.59 (6H, m), 7.82 (1H, d, J=2.4 Hz), 8.60 (1H, brs)

ESI (LC-MS positive mode) m/z 419 (M+H).

Example 23

7-(3-Hydroxymethylpiperidin-1-yl)-3-(2-trifluoromethylphenyl)-2H-isoquinolin-1-one

[Formula 39]

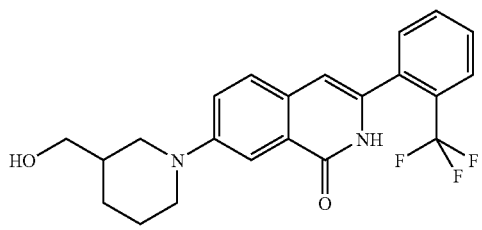

$^1$H-NMR (270 MHz, CDCl$_3$) δ (ppm): 1.16-1.33 (1H, m), 1.60-2.05 (5H, m), 2.73 (1H, dd, J=9.9, 12.2 Hz), 2.90 (1H, dt, J=3.0, 11.7 Hz), 3.55-3.81 (3H, m), 3.83-3.93 (1H, m), 6.45 (1H, s), 7.41 (1H, dd, J=2.3, 8.6 Hz), 7.43-7.70 (4H, m), 7.75-7.84 (2H, m), 8.58 (1H, brs)

ESI (LC-MS positive mode) m/z 403 (M+H).

Example 24

7-(3-Hydroxymethylpiperidin-1-yl)-3-phenyl-2H-isoquinolin-1-one

[Formula 40]

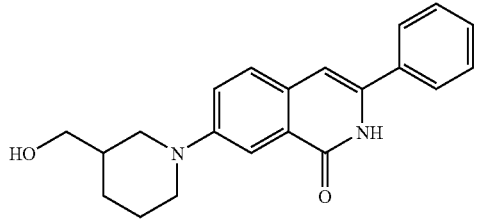

$^1$H-NMR (270 MHz, CDCl$_3$) δ (ppm): 1.23-1.32 (1H, m), 1.64-2.07 (5H, m), 2.72 (1H, dd, J=9.9, 12.2 Hz), 2.89 (1H, dt, J=3.0, 12.2 Hz), 3.53-3.79 (3H, m), 3.90 (1H, dd, J=3.5, 12.2 Hz), 6.72 (1H, s), 7.35-7.52 (5H, m), 7.59-7.65 (2H, m), 7.82 (1H, d, J=2.6 Hz), 9.23 (1H, brs)

ESI (LC-MS positive mode) m/z 335 (M+H).

Example 25

7-(3-Hydroxymethylpiperidin-1-yl)-3-(2-trifluoromethoxyphenyl)-2H-isoquinolin-1-one

[Formula 41]

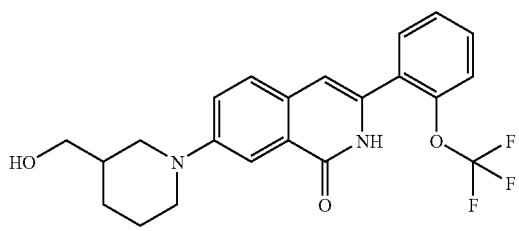

¹H-NMR (270 MHz, CDCl₃) δ (ppm): 1.20-1.28 (1H, m), 1.69-1.75 (1H, m), 1.82-1.88 (3H, m), 1.94-2.01 (1H, m), 2.73 (1H, dd, J=10.4, 12.4 Hz), 2.90 (1H, dt, J=2.8, 11.2 Hz), 3.58-3.70 (2H, m), 3.76 (1H, d, J=12.8 Hz), 3.90 (1H, dd, J=4.0, 12.0 Hz), 6.63 (1H, s), 7.37-7.50 (5H, m), 7.58 (1H, dd, J=1.6, 7.6 Hz), 7.82 (1H, d, J=2.4 Hz), 8.82 (1H, brs)

ESI (LC-MS positive mode) m/z 419 (M+H).

Example 26

7-(2-Hydroxymethylpiperidin-1-yl)-3-(2-trifluoromethylphenyl)-2H-isoquinolin-1-one

[Formula 42]

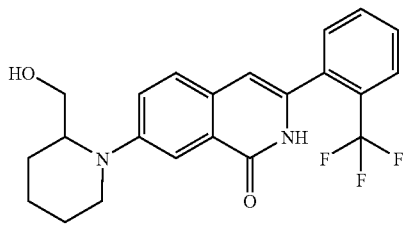

¹H-NMR (270 MHz, CDCl₃) δ (ppm): 1.64-1.80 (6H, m), 2.04-2.07 (1H, m), 3.12-3.20 (1H, m), 3.63-3.68 (2H, m), 3.86-3.93 (1H, m), 4.12-4.15 (1H, m), 6.45 (1H, s), 7.39-7.43 (1H, dd, J=2.31, 8.91 Hz), 7.45-7.48 (1H, d, J=8.58 Hz), 7.52-7.67 (3H, m), 7.78-7.81 (1H, m), 7.85-7.86 (1H, d, J=2.31 Hz), 8.54 (1H, brs)

EI (positive mode) m/z 402 (M⁺).

Example 27

7-(2-Hydroxymethylpiperidin-1-yl)-3-phenyl-2H-isoquinolin-1-one

[Formula 43]

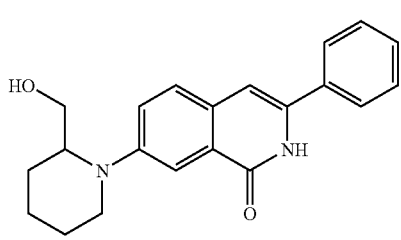

¹H-NMR (270 MHz, CDCl₃) δ (ppm): 1.60-1.88 (6H, m), 2.35 (1H, brs), 3.10-3.22 (1H, m), 3.60-3.73 (2H, m), 3.89 (1H, dd, J=6.9, 10.9 Hz), 4.06-4.18 (1H, m), 6.71 (1H, s), 7.35-7.52 (5H, m), 7.60-7.65 (2H, m), 7.85 (1H, d, J=2.6 Hz), 9.33 (1H, brs)

ESI (LC-MS positive mode) m/z 335 (M+H).

Example 28

7-(2-Hydroxymethylpiperidin-1-yl)-3-(2-trifluoromethoxyphenyl)-2H-isoquinolin-1-one

[Formula 44]

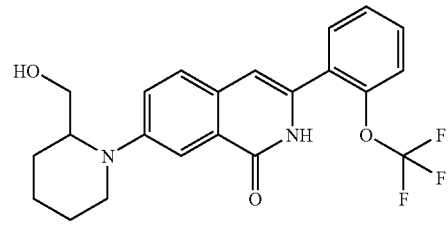

¹H-NMR (270 MHz, CDCl₃) δ (ppm): 1.61-1.80 (6H, m), 1.94-1.95 (1H, m), 3.12-3.20 (1, m), 3.65-3.73 (2H, m), 3.87-3.93 (1H, m), 4.13-4.16 (1H, m), 6.62 (1H, s), 7.37-7.51 (5H, m), 7.57-7.60 (1H, m), 7.85-7.86 (1H, d, J=2.31 Hz), 8.71 (1H, brs)

EI (positive mode) m/z 418 (M⁺).

Example 29

7-(4-Hydroxypiperidin-1-yl)-3-(2-trifluoromethylphenyl)-2H-isoquinolin-1-one

[Formula 45]

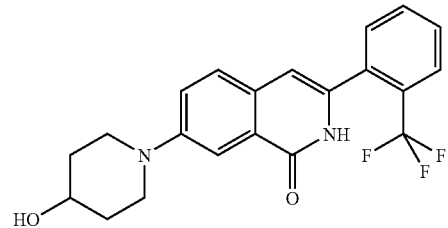

¹H-NMR (270 MHz, CDCl₃) δ (ppm): 1.63-1.80 (3H, m), 1.98-2.11 (2H, m), 3.08 (2H, ddd, J=3.0, 9.9, 12.9 Hz), 3.67-3.80 (2H, m), 3.85-3.98 (1H, m), 6.45 (1H, s), 7.38 (1H, dd, J=2.6, 8.9 Hz), 7.43-7.68 (4H, m), 7.77-7.83 (2H, m), 8.55 (1H, brs)

ESI (LC-MS positive mode) m/z 389 (M+H).

Example 30

7-(4-Hydroxypiperidin-1-yl)-3-phenyl-2H-isoquinolin-1-one

[Formula 46]

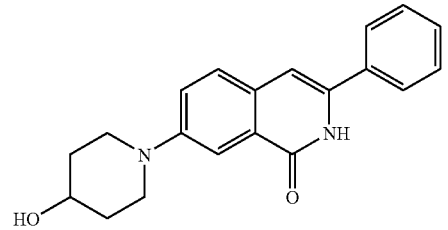

¹H-NMR (270 MHz, CDCl₃) δ (ppm): 1.58-1.80 (3H, m), 1.98-2.11 (2H, m), 3.03-3.15 (2H, m), 3.68-3.79 (2H, m), 3.85-3.98 (1H, m), 6.72 (1H, s), 7.38 (1H, dd, J=2.6, 8.9 Hz), 7.43-7.53 (4H, m), 7.60-7.65 (2H, m), 7.81 (1H, d, J=2.6 Hz), 8.83 (1H, brs)

ESI (LC-MS positive mode) m/z 321 (M+H).

Example 31

7-(4-Hydroxypiperidin-1-yl)-3-(2-trifluoromethoxyphenyl)-2H-isoquinolin-1-one

[Formula 47]

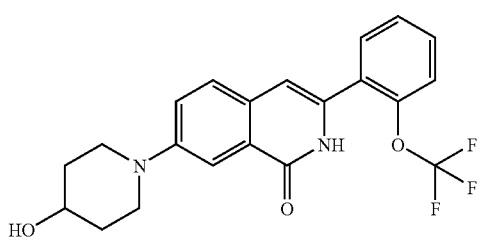

¹H-NMR (270 MHz, CDCl₃) δ (ppm): 1.51 (1H, d, J=4.4 Hz), 1.72 (2H, m), 2.05 (2H, m), 3.10 (2H, m), 3.70 (2H, m), 3.80-3.90 (1H, m), 6.60 (1H, brs), 7.40-7.60 (6H, m), 7.80 (1H, d, J=2.4 Hz), 8.60 (1H, brs)

ESI (LC-MS positive mode) m/z 405 (M+H).

Example 32

7-(3-Hydroxypiperidin-1-yl)-3-(2-trifluoromethylphenyl)-2H-isoquinolin-1-one

[Formula 48]

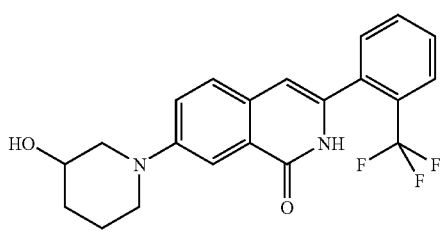

¹H-NMR (270 MHz, CDCl₃) δ (ppm): 1.60-1.80 (2H, m), 1.82-2.02 (2H, m), 2.13-2.21 (1H, m), 3.22 (1H, dd, J=6.1, 12.7 Hz), 3.18-3.37 (2H, m), 3.52 (1H, dd, J=3.0, 12.2 Hz), 3.92-4.03 (1H, m), 6.45 (1H, s), 7.39 (1H, dd, J=2.6, 8.6 Hz), 7.42-7.70 (4H, m), 7.81 (1H, dd, J=1.6, 9.2 Hz), 7.84 (1H, d, J=2.6 Hz), 8.48 (1H, brs)

ESI (LC-MS positive mode) m/z 389 (M+H).

Example 33

7-(3-Hydroxypiperidin-1-yl)-3-phenyl-2H-isoquinolin-1-one

[Formula 49]

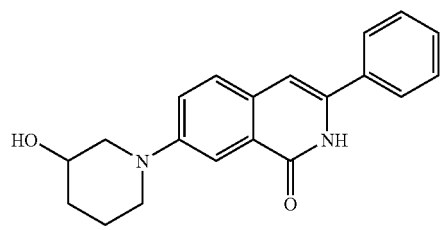

¹H-NMR (270 MHz, CDCl₃) δ (ppm): 1.50-1.80 (2H, m), 1.82-2.05 (2H, m), 2.09-2.18 (1H, m), 3.20 (1H, dd, J=6.8, 12.0 Hz), 3.18-3.35 (2H, m), 3.51 (1H, dd, J=3.1, 12.0 Hz), 3.92-4.02 (1H, m), 6.72 (1H, s), 7.38 (1H, dd, J=2.6, 8.9 Hz), 7.41-7.53 (4H, m), 7.58-7.64 (2H, m), 7.83 (1H, d, J=2.6 Hz), 8.85 (1H, brs)

ESI (LC-MS positive mode) m/z 321 (M+H).

Example 34

7-(3-Hydroxypiperidin-1-yl)-3-(2-trifluoromethoxyphenyl)-2H-isoquinolin-1-one

[Formula 50]

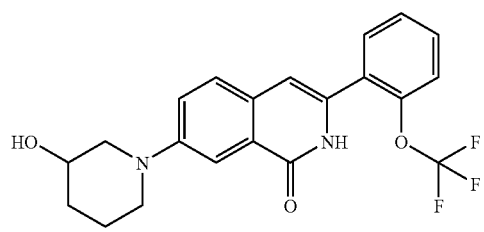

¹H-NMR (270 MHz, CDCl₃) δ (ppm): 1.65-1.75 (2H, m), 1.76-1.94 (2H, m), 2.06 (1H, d, J=7.3 Hz), 3.18-3.34 (3H, m), 3.52 (1H, dd, J=2.9, 12.2 Hz), 3.98 (1H, m), 6.60 (1H, s), 7.30-7.60 (6H, m), 7.84 (1H, d, J=2.4 Hz), 8.60 (1H, brs)

ESI (LC-MS positive mode) m/z 405 (M+H).

Example 35

7-(3-Hydroxypyrrolidin-1-yl)-3-(2-trifluoromethylphenyl)-2H-isoquinolin-1-one

[Formula 51]

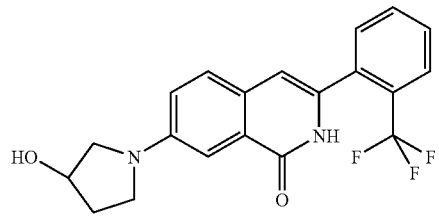

¹H-NMR (270 MHz, DMSO-d₆) δ (ppm): 1.97-2.13 (2H, m), 3.16-3.20 (1H, m), 3.38-3.55 (3H, m), 4.4-4.5 (1H, m), 5.02-5.03 (1H, d, J=3.0 Hz), 6.35 (1H, s), 7.04-7.07 (1H, m), 7.1-7.2 (1H, m), 7.50-7.53 (1H, d, J=8.58 Hz), 7.58-7.61 (1H, d, J=7.26 Hz), 7.64-7.78 (2H, m), 7.83-7.86 (1H, d, J=7.92 Hz), 11.3 (1H, brs)
EI-MS m/z 374 (M⁺).

Example 36

7-(3-Hydroxypyrrolidin-1-yl)-3-phenyl-2H-isoquinolin-1-one

[Formula 52]

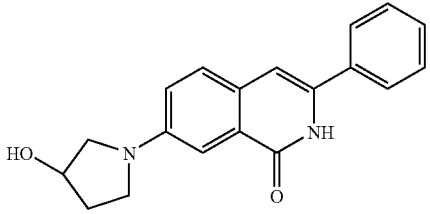

¹H-NMR (270 MHz, DMSO-d₆) δ (ppm): 1.88-2.00 (1H, m), 2.00-2.18 (1H, m), 3.15-3.20 (1H, m), 3.30-3.50 (2H, m), 3.52 (1H, dd, J=4.8, 10.4 Hz), 4.40-4.50 (1H, m), 5.03 (1H, d, J=3.6 Hz), 6.84 (1H, s), 7.06 (1H, dd, J=2.6, 8.9 Hz), 7.15 (1H, d, J=2.6 Hz), 7.32-7.50 (3H, m), 7.57 (1H, d, J=8.6 Hz), 7.72-7.80 (2H, m), 11.24 (1H, m)
ESI (LC-MS positive mode) m/z 307 (M+H).

Example 37

7-(3-Hydroxypyrrolidin-1-yl)-3-(2-trifluoromethoxyphenyl)-2H-isoquinolin-1-one

[Formula 53]

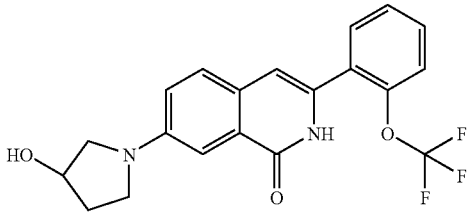

¹H-NMR (270 MHz, DMSO-d₆) δ (ppm): 1.97 (1H, brs), 2.06-2.12 (1H, m), 3.18 (1H, d, J=9.6 Hz), 3.37-3.45 (2H, m), 3.50-3.54 (1H, m), 4.45 (1H, brs), 5.02 (1H, d, J=3.2 Hz), 6.54 (1H, s), 7.06 (1H, dd, J=2.4, 8.8 Hz), 7.15 (1H, s), 7.46-7.65 (5H, m), 11.30 (1H, s)
ESI (LC-MS positive mode) m/z 391 (M+H).

Example 38

7-Amino-3-(2-trifluoromethylphenyl)-2H-isoquinolin-1-one

[Formula 54]

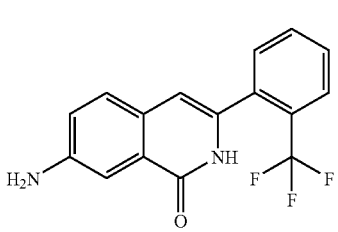

21 ml (21 mmol) of a 1 M lithium bis(trimethylsilyl)amide THF solution was added to a mixture consisting of 2.50 g (7.72 mmol) of the 7-chloro-3-(2-trifluoromethylphenyl)-2H-isoquinolin-1-one prepared in Step B of Example 1; 64.9 mg (0.185 mmol) of 2-(dicyclohexylphosphino)biphenyl; and 70.7 mg (0.0772 mmol) of tris(dibenzylideneacetone)dipalladium. The obtained mixture was stirred under heating to reflux over a day and a night. Thereafter, the reaction solution was cooled to a room temperature, and 63 ml of 1 N hydrochloric acid was then added thereto, followed by stirring for 5 minutes. Thereafter, the reaction solution was neutralized in 8 ml of a 5 N sodium hydroxide aqueous solution and then extracted with methylene chloride. The extract was washed with a saturated saline solution, and was then dried over anhydrous sodium sulfate, followed by concentration. The obtained residue was then purified by silica gel column chromatography (ethyl acetate:hexane=3:1 to 6:1), so as to obtain 2.14 g (91%) of 7-amino-3-(2-trifluoromethylphenyl)-2H-isoquinolin-1-one in the form of a brown solid.
¹H-NMR (270 MHz, CDCl₃) δ (ppm): 4.00 (2H, brs), 6.43 (1H, s), 7.07 (1H, dd, J=2.5, 8.3 Hz), 7.40 (1H, d, J=8.3 Hz), 7.50-7.69 (4H, m), 7.76-7.83 (1H, m), 8.63 (1H, brs)
ESI (LC-MS positive mode) m/z 305 (M+H).

The following compounds (Examples 39 and 40) were synthesized by a method similar to that of Example 38, using the compound obtained in Example 2 or 3 as a starting material.

Example 39

7-Amino-3-phenyl-2H-isoquinolin-1-one

[Formula 55]

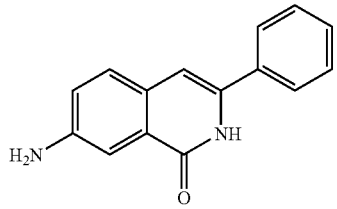

¹H-NMR (270 MHz, DMSO-d₆) δ (ppm): 5.57 (2H, brs), 6.75 (1H, s), 7.01 (1H, dd, J=2.7, 8.1 Hz), 7.28-7.49 (5H, m), 7.73 (2H, d, J=8.9 Hz), 11.10 (1H, brs)
EI (positive mode) m/z 236 (M⁺).

Example 40

7-Amino-3-(2-trifluoromethoxyphenyl)-2H-isoquinolin-1-one

[Formula 56]

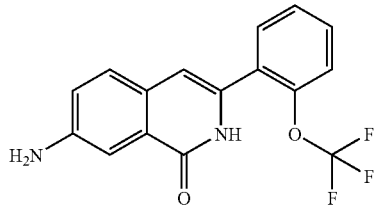

¹H-NMR (270 MHz, CDCl₃) δ (ppm): 4.03 (2H, brs), 6.62 (1H, s), 7.07 (1H, dd, J=2.5, 8.4 Hz), 7.35-7.52 (4H, m), 7.58 (1H, dd, J=2.0, 7.3 Hz), 7.66 (1H, d, J=2.3 Hz), 8.80 (1H, brs)
ESI (LC-MS positive mode) m/z 321 (M+H).

Example 41

7-(2-Hydroxyethylamino)-3-(2-trifluoromethylphenyl)-2H-isoquinolin-1-one and 7-[bis(2-hydroxyethyl)amino]-3-(2-trifluoromethylphenyl)-2H-isoquinolin-1-one

[Formula 57]

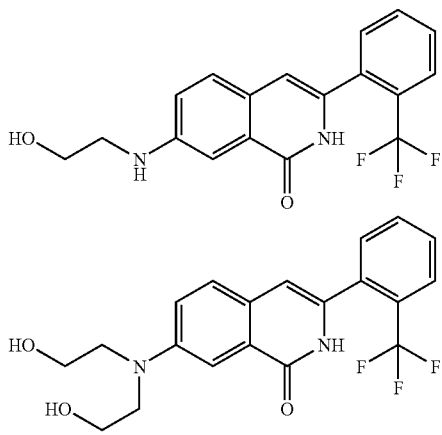

350 mg (1.15 mmol) of the 7-amino-3-(2-trifluoromethylphenyl)-2H-isoquinolin-1-one obtained in Example 38 was dissolved in 11.5 ml of methanol, and thereafter, 1.15 ml of acetic acid and 552.5 mg (4.60 mmol) of glycolaldehyde dimer were added thereto. Thereafter, 722 mg (11.5 mmol) of sodium cyanoborohydride was added to the mixture under cooling on ice. The temperature of the mixture was increased to a room temperature, and the mixture was then stirred for 8 hours. Thereafter, a saturated sodium bicarbonate aqueous solution was added to the reaction solution, and the mixture was then extracted with ethyl acetate. The extract was dried over anhydrous sodium sulfate and was then concentrated. The obtained residue was purified by silica gel column chromatography (methylene chloride:methanol=20:1 to 12:1), so as to obtain 61.8 mg (15%) of 7-(2-hydroxyethylamino)-3-(2-trifluoromethylphenyl)-2H-isoquinolin-1-one in the form of a yellow amorphous substance, as well as 369.3 mg (82%) of 7-[bis(2-hydroxyethyl)amino]-3-(2-trifluoromethylphenyl)-2H-isoquinolin-1-one in the form of a yellow foaming substance.

7-(2-hydroxyethylamino)-3-(2-trifluoromethylphenyl)-2H-isoquinolin-1-one $^1$H-NMR (270 MHz, CDCl$_3$) δ (ppm): 1.79 (1H, brs), 3.46 (2H, t, J=5.6 Hz), 3.86-3.95 (2H, m), 4.42 (1H, brs), 6.44 (1H, s), 7.07 (1H, dd, J=2.6, 8.6 Hz), 7.41 (1H, d, J=8.6 Hz), 7.49-7.69 (4H, m), 7.78-7.82 (1H, m), 8.36 (1H, brs)
ESI (LC-MS positive mode) m/z 349 (M+H).

7-[bis(2-hydroxyethyl)amino]-3-(2-trifluoromethylphenyl)-2H-isoquinolin-1-one $^1$H-NMR (270 MHz, CDCl$_3$) δ (ppm): 3.59 (2H, brs), 3.71 (4H, t, J=4.9 Hz), 3.94 (4H, t, J=4.9 Hz), 6.43 (1H, s), 7.19 (1H, dd, J=3.0, 8.9 Hz), 7.43 (1H, d, J=8.9 Hz), 7.49-7.68 (4H, m), 7.63 (1H, d, J=7.6 Hz), 8.56 (1H, brs)
ESI (LC-MS positive mode) m/z 393 (M+H).

The following compounds (Examples 42 to 45) were synthesized by a method similar to that of Example 41, using the compound obtained in Example 38, 39, or 40, as a starting material.

Example 42

7-(2-Hydroxyethyl)amino-3-phenyl-2H-isoquinolin-1-one monotrifluoroacetate and 7-[bis(2-hydroxyethyl)amino]-3-phenyl-2H-isoquinolin-1-one

[Formula 58]

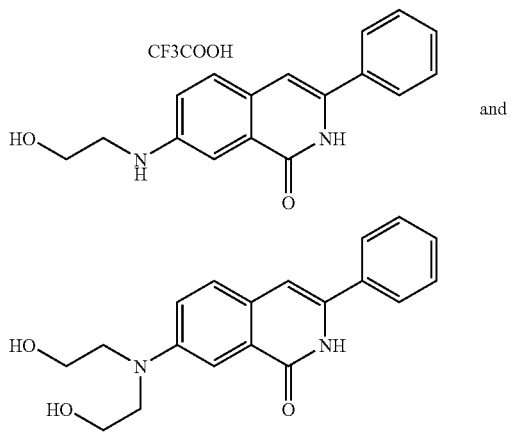

7-(2-hydroxyethyl)amino-3-phenyl-2H-isoquinolin-1-one monotrifluoroacetate was obtained by performing the same purification as that in Example 41 and further performing purification using preparative HPLC (ODS-80TS 55×300 mm; an acetonitrile:water solvent was used as an eluent).

7-(2-Hydroxyethyl)amino-3-phenyl-2H-isoquinolin-1-one monotrifluoroacetate $^1$H-NMR (270 MHz, DMSO-d$_6$) δ (ppm): 3.21 (2H, t, J=5.9 Hz), 3.59 (1H, t, J=5.0 Hz), 3.61 (2H, t, J=5.9 Hz), 3.85 (2H, brs), 6.79 (1H, s), 7.12 (1H, dd, J=2.4, 8.4 Hz), 7.22-7.24 (1H, m), 7.35-7.56 (4H, m), 7.72-7.76 (2H, m), 11.20 (1H, brs)
ESI (LC-MS positive mode) m/z 281 (M+H−TFA).

7-[Bis(2-hydroxyethyl)amino]-3-phenyl-2H-isoquinolin-1-one $^1$H-NMR (270 MHz, DMSO-d$_6$) δ (ppm): 3.45-3.63 (8H, m), 4.84 (2H, m), 6.81 (1H, s), 7.18-7.25 (1H, m), 7.33-7.57 (5H, m), 7.70-7.79 (2H, m), 11.22 (1H, brs)
ESI (LC-MS positive mode) m/z 325 (M+H).

Example 43

7-(2-Hydroxyethylamino)-3-(2-trifluoromethoxyphenyl)-2H-isoquinolin-1-one and 7-[bis(2-hydroxyethyl)amino]-3-(2-trifluoromethoxyphenyl)-2H-isoquinolin-1-one

[Formula 59]

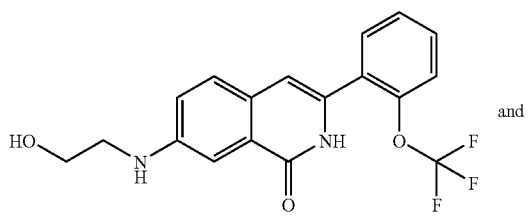

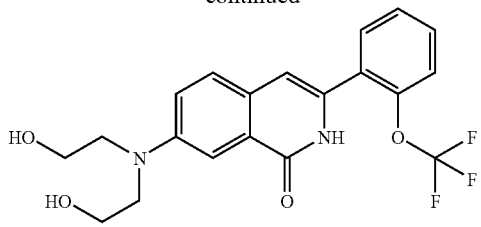

7-(2-hydroxyethylamino)-3-(2-trifluoromethoxyphenyl)-2H-isoquinolin-1-one $^1$H-NMR (270 MHz, CDCl$_3$) δ (ppm): 1.70 (1H, brs), 3.46 (2H, t, J=5.1 Hz), 3.88-3.95 (2H, m), 4.40 (1H, brs), 6.62 (1H, s), 7.06 (1H, dd, J=2.6, 8.6 Hz), 7.35-7.50 (4H, m), 7.54 (1H, d, J=2.6 Hz), 7.58 (1H, dd, J=1.7, 7.3 Hz), 8.59 (1H, brs)
ESI (LC-MS positive mode) m/z 365 (M+H).

7-[Bis(2-hydroxyethyl)amino]-3-(2-trifluoromethoxyphenyl)-2H-isoquinolin-1-one $^1$H-NMR (270 MHz, CDCl$_3$) δ (ppm): 3.50-3.65 (8H, m), 4.84 (2H, t, J=5.1 Hz), 6.53 (1H, s), 7.23 (1H, dd, J=2.6, 8.9 Hz), 7.37 (1H, d, J=2.6 Hz), 7.43-7.64 (5H, m), 11.28 (1H, s)
ESI (LC-MS positive mode) m/z 409 (M+H).

Example 44

7-(2-Methoxyethylamino)-3-phenyl-2H-isoquinolin-1-one and 7-[bis-(2-methoxyethyl)amino]-3-phenyl-2H-isoquinolin-1-one

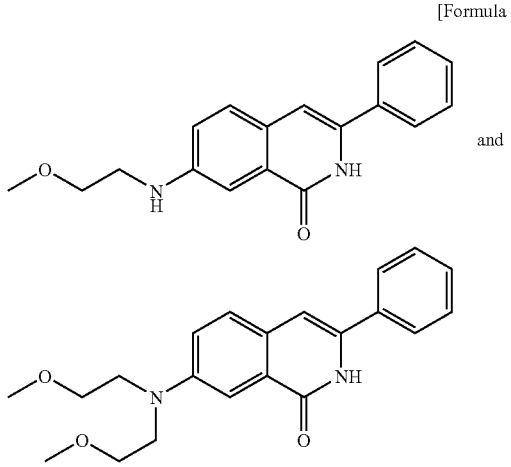

[Formula 60]

and 7-(2-Methoxyethylamino)-3-phenyl-2H-isoquinolin-1-one $^1$H-NMR (270 MHz, CDCl$_3$) δ (ppm): 3.40-3.50 (5.5H, m), 3.65-3.69 (2H, t, J=4.95 Hz), 4.39 (0.5H, brs), 6.71 (1H, s), 7.02-7.06 (1H, m), 7.32-7.51 (5.5H, m), 7.59-7.62 (2H, m), 8.86 (0.5H, brs)
EI-MS m/z 294 (M$^+$).

7-[Bis-(2-methoxyethyl)amino]-3-phenyl-2H-isoquinolin-1-one $^1$H-NMR (270 MHz, CDCl$_3$) δ (ppm): 3.37 (6H, s), 3.43-3.73 (8H, m), 6.71 (1H, s), 7.20-7.24 (1H, dd, J=2.64, 8.91 Hz), 7.38-7.52 (4H, m), 7.56-7.57 (1H, d, J=2.64 Hz), 7.60-7.63 (2H, m), 8.83 (1H, brs)
ESI (LC-MS positive mode) m/z 353 (M+H).

Example 45

7-(2,3-Dihydroxypropylamino)-3-phenyl-2H-isoquinolin-1-one

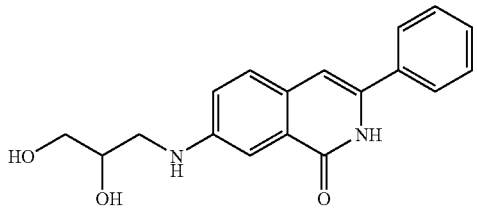

[Formula 61]

$^1$H-NMR (270 MHz, CD$_3$OD) δ (ppm): 3.17-3.24 (1H, dd, J=6.93, 13.2 Hz), 3.37-3.44 (1H, dd, J=4.95, 13.2 Hz), 3.56-3.69 (2H, m), 3.87-3.93 (1H, m), 6.84 (1H, s), 7.15-7.20 (1H, dd, J=2.31, 8.58 Hz), 7.38-7.52 (5H, m), 7.67-7.70 (2H, m)
FAB-MS m/z 311 (M+H).

Example 46

7-[(2,3-Dihydroxypropyl)(2-hydroxyethyl)amino]-3-phenyl-2H-isoquinolin-1-one

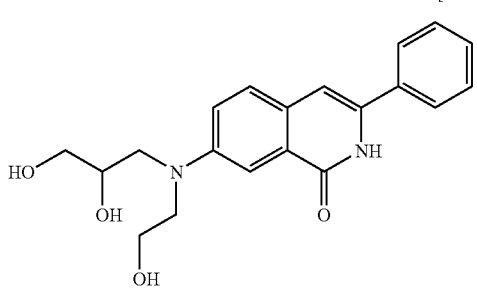

[Formula 62]

The 7-(2-hydroxyethyl)amino-3-phenyl-2H-isoquinolin-1-one monotrifluoroacetate obtained in Example 42 was used as a raw material, and a method similar to that of Example 41 was applied, so as to obtain 7-[(2,3-dihydroxypropyl)(2-hydroxyethyl)amino]-3-phenyl-2H-isoquinolin-1-one.

$^1$H-NMR (270 MHz, CD$_3$OD) δ (ppm): 3.39-3.47 (1H, dd, J=7.92, 15.2 Hz), 3.56-3.69 (3H, m), 3.71-3.88 (4H, m), 3.98-4.07 (1H, m), 6.85 (1H, s), 7.35-7.52 (5H, m), 7.57-7.60 (1H, d, J=8.91 Hz), 7.66-7.70 (2H, m)
FAB-MS m/z 355 (M+H).

Example 47

7-[(2-Hydroxyethyl)methylamino]-3-(2-trifluoromethylphenyl)-2H-isoquinolin-1-one

[Formula 63]

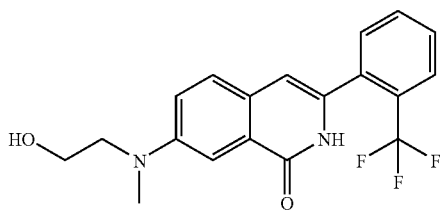

120 mg (1.0 mmol) of glycolaldehyde dimer and 2 ml of acetic acid were added to 10 ml of a methanol solution containing 473 mg (1.55 mmol) of the 7-amino-3-(2-trifluoromethylphenyl)-2H-isoquinolin-1-one obtained in Example 38. Thereafter, 754 mg (12.0 mmol) of sodium cyanoborohydride was further added thereto, and the obtained mixture was then stirred at a room temperature for 3 hours. Thereafter, 0.82 ml (10 mmol) of a 37% formalin aqueous solution was added to the reaction solution, and the obtained mixture was further stirred for 2.5 hours. Thereafter, the reaction solution was concentrated, and a saturated sodium bicarbonate aqueous solution and methylene chloride were then added to the concentrate. An organic layer was separated, and was then dried over anhydrous sodium sulfate. Thereafter, the solvent was distilled away under reduced pressure. The obtained residue was purified by silica gel chromatography (hexane:ethyl acetate methanol=15:30:1), so as to obtain 344 mg (61%) of 7-[(2-hydroxyethyl)methylamino]-3-(2-trifluoromethylphenyl)-2H-isoquinolin-1-one in the form of a yellow solid.

$^1$H-NMR (270 MHz, CDCl$_3$) δ (ppm): 2.12 (1H, brs), 3.12 (3H, s), 3.63 (2H, t, J=5.8 Hz), 3.88 (2H, t, J=5.8 Hz), 6.44 (1H, s), 7.24-7.26 (1H, m), 7.46 (1H, d, J=8.8 Hz), 7.52-7.65 (4H, m), 7.79 (1H, d, J=8.4 Hz), 8.55 (1H, brs)

ESI (LC-MS positive mode) m/z 363 (M+H).

The following compounds (Examples 48 to 52) were synthesized by a method similar to that of Example 47, using the compound obtained in Example 38, 39, or 40, as a starting material.

Example 48

7-[(2-Hydroxyethyl)methylamino]-3-phenyl-2H-isoquinolin-1-one

[Formula 64]

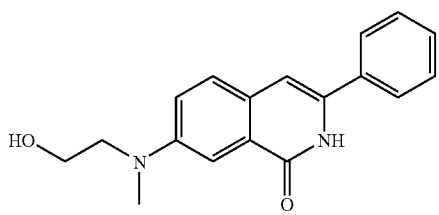

$^1$H-NMR (270 MHz, DMSO-d$_6$) δ (ppm): 3.04 (3H, s), 3.51-3.61 (4H, m), 4.77 (1H, brs), 6.83 (1H, s), 7.26 (1H, dd, J=1.98, 8.91 Hz), 7.34 (1H, d, J=1.98 Hz), 7.38-7.48 (3H, m), 7.56 (1H, d, J=8.91 Hz), 7.76 (2H, d, J=8.25 Hz), 11.2 (1H, brs)

ESI (LC-MS positive mode) m/z 295 (M+H).

Example 49

7-[(2-Hydroxyethyl)methylamino]-3-(2-trifluoromethoxyphenyl)-2H-isoquinolin-1-one

[Formula 65]

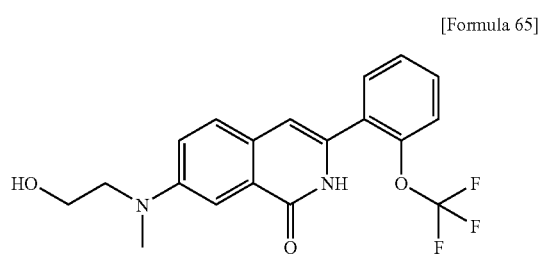

$^1$H-NMR (270 MHz, CDCl$_3$) δ (ppm): 2.29 (1H, brs), 3.12 (3H, s), 3.63 (2H, t, J=5.8 Hz), 3.89 (2H, t, J=5.8 Hz), 6.64 (1H, s), 7.24 (1H, dd, J=2.6, 8.9 Hz), 7.33-7.52 (4H, m), 7.59 (1H, dd, J=1.8, 7.1 Hz), 7.64 (1H, d, J=2.6 Hz), 9.00 (1H, brs)

ESI (LC-MS positive mode) m/z 379 (M+H).

Example 50

7-[(2,3-Dihydroxypropyl)-methylamino]-3-phenyl-2H-isoquinolin-1-one

[Formula 66]

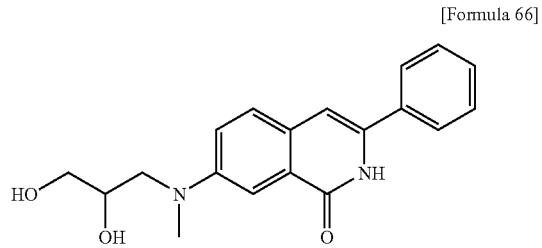

$^1$H-NMR (400 MHz, CD$_3$OD) δ (ppm): 3.14 (3H, s), 3.42 (1H, dd, J=7.32, 15.1 Hz), 3.55-3.69 (3H, m), 3.93-3.99 (1H, m), 6.85 (1H, s), 7.34-7.42 (2H, m), 7.45-7.49 (3H, m), 7.58 (1H, d, J=9.28 Hz), 7.66-7.69 (2H, m)

FAB-MS m/z 325 (M+H).

Example 51

7-[Methyl-((2S,3R)-2,3,4-trihydroxybutyl)amino]-3-phenyl-2H-isoquinolin-1-one

[Formula 67]

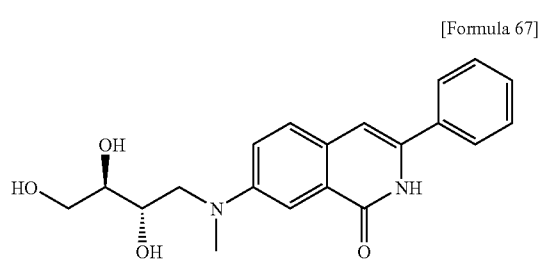

$^1$H-NMR (400 MHz, CD$_3$OD) δ (ppm): 3.17 (3H, s), 3.36-3.41 (1H, m), 3.54-3.58 (1H, m), 3.63-3.68 (1H, m), 3.78-3.82 (1H, m), 3.87-3.96 (2H, m), 6.86 (1H, s), 7.38-7.42 (2H, m), 7.46-7.50 (3H, m), 7.56-7.59 (1H, d, J=8.79 Hz), 7.68-7.70 (2H, m)

FAB-MS m/z 355 (M+H).

Example 52 t-Butyl(2-{methyl-[1-oxo-3-(2-trifluoromethoxyphenyl)-1,2-dihydroisoquinolin-7-yl]amino}ethyl)carbamate

[Formula 68]

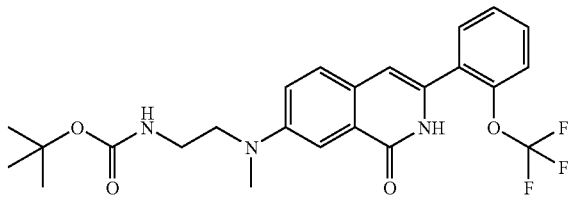

$^1$H-NMR (270 MHz, CDCl$_3$) δ (ppm): 1.45 (9H, s), 3.11 (3H, s), 3.23-3.41 (4H, m), 4.72 (1H, brs), 6.63 (1H, s), 7.18-7, 25 (1H, m), 7.34-7.50 (4H, m), 7.55-7.62 (2H, m), 8.64 (1H, brs)

ESI (LC-MS positive mode) m/z 478 (M+H).

Example 53

7-[(2-Aminoethyl)-methylamino]-3-(2-trifluoromethoxyphenyl)-2H-isoquinolin-1-one ditrifluoroacetate

[Formula 69]

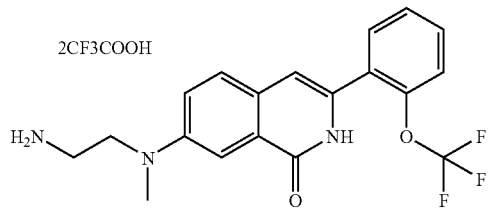

2 ml of trifluoroacetic acid was added to 4 ml of a methylene chloride solution containing 455.4 mg (0.954 mmol) of t-butyl(2-{methyl-[1-oxo-3-(2-trifluoromethoxyphenyl)-1,2-dihydroisoquinolin-7-yl]amino}ethyl)carbamate obtained in Example 52. The obtained mixture was stirred at a room temperature for 2.5 hours. Thereafter, the reaction solution was concentrated. The obtained residue was purified by preparative HPLC (ODS-80TS 55×300 mm; an acetonitrile:water solvent was used as an eluent), so as to obtain 299.4 mg (52%) of 7-[(2-aminoethyl)methylamino]-3-(2-trifluoromethoxyphenyl)-2H-isoquinolin-1-one ditrifluoroacetate in the form of a deep green viscous oily substance.

$^1$H-NMR (270 MHz, DMSO-d$_6$) δ (ppm): 2.95-3.10 (6H, m), 3.65 (2H, t, J=6.9 Hz), 6.57 (1H, s), 7.32 (1H, dd, J=3.0, 8.9 Hz), 7.40-7.68 (6H, m), 7.84 (3H, brs), 11.37 (1H, s)

ESI (LC-MS positive mode) m/z 378 (M+H−2TFA).

Example 54

7-(2-Aminoethylamino)-3-phenyl-2H-isoquinolin-1-one ditrifluoroacetate

[Formula 70]

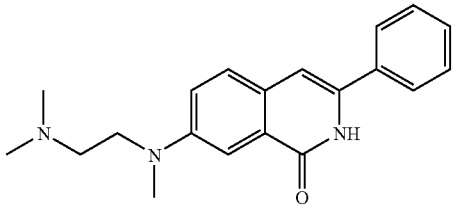

0.5 ml of acetic acid and 337 mg (2.12 mmol) of t-butyl N-(2-oxoethyl)carbamate were added to 5 ml of a methanol solution containing 100 mg (0.423 mmol) of the 7-amino-3-phenyl-2H-isoquinolin-1-one obtained in Example 39. Thereafter, 140 mg (2.12 mmol) of sodium cyanoborohydride was added thereto under cooling on ice, and the obtained mixture was then stirred at a room temperature for 1 hour. Thereafter, 140 mg (2.12 mmol) of sodium cyanoborohydride was further added to the reaction solution, followed by stirring over a day and a night. Thereafter, methanol was distilled away, and a saturated sodium bicarbonate aqueous solution was added thereto. The mixture was extracted with ethyl acetate. The extract was dried over anhydrous sodium sulfate, and the solvent was distilled away under reduced pressure, so as to obtain approximately 500 mg of a residue. The obtained residue was dissolved in a mixed solvent consisting of 1 ml of methylene chloride and 1 ml of methanol, and 7 ml of trifluoroacetic acid was then added thereto under cooling on ice. The mixture was stirred for 1 hour. Thereafter, the reaction solution was concentrated, and the obtained residue was then dissolved in methanol. The obtained solution was purified by preparative HPLC (ODS-80TS 55×300 mm; a 0.05% trifluoroacetic acid solution (water:acetonitrile=45:25) was used as an eluent), so as to obtain 73 mg (34%) of 7-(2-aminoethylamino)-3-phenyl-2H-isoquinolin-1-one ditrifluoroacetate in the form of a light yellow solid.

$^1$H-NMR (270 MHz, DMSO-d$_6$) δ (ppm): 3.02 (2H, t, J=6.2 Hz), 3.22-3.43 (6H, m), 6.23 (1H, t, J=5.5 Hz), 6.81 (1H, s), 7.10 (1H, dd, J=2.3, 8.8 Hz), 7.26-7.29 (1H, m), 7.36-7.54 (4H, m), 7.70-7.85 (3H, m)

ESI (LC-MS positive mode) m/z 280 (M+H−2TFA).

Example 55

7-[(2-Dimethylaminoethyl)methylamino]-3-phenyl-2H-isoquinolin-1-one

[Formula 71]

0.021 ml (0.12 mmol) of diisopropylethylamine, 0.5 ml of acetic acid, 1 ml of a 37% formalin aqueous solution, and 20 mg (2.96 mmol) of sodium cyanoborohydride were added to 5 ml of a methanol solution containing 30 mg (0.059 mmol) of the 7-(2-aminoethylamino)-3-phenyl-2H-isoquinolin-1-one ditrifluoroacetate obtained in Example 54. The obtained mixture was stirred at a room temperature over a day and a night. Thereafter, the solvent was distilled away, and a saturated sodium bicarbonate aqueous solution was added thereto, followed by extraction with ethyl acetate. The extract was dried over anhydrous magnesium sulfate, and then concentrated under reduced pressure. The obtained residue was purified by preparative HPLC (ODS-80TS 55×300 mm; a 0.05% trifluoroacetic acid solution (water:acetonitrile=45:25) was used as an eluent). The obtained compound was once dissolved in ethyl acetate. The solution was washed with a saturated sodium bicarbonate aqueous solution, and was then dried over anhydrous magnesium sulfate, followed by concentration, so as to obtain 11 mg (58%) of 7-[(2-dimethylaminoethyl)methylamino]-3-phenyl-2H-isoquinolin-1-one in the form of a solid.

$^1$H-NMR (270 MHz, CDCl$_3$) δ (ppm): 2.24 (6H, s), 2.46 (2H, t, J=7.3 Hz), 3.02 (3H, s), 3.51 (2H, t, J=7.3 Hz), 6.65 (1H, s), 7.11 (1H, dd, J=2.6, 8.5 Hz), 7.29-7.44 (4H, m), 7.50 (1H, d, J=2.4 Hz), 7.56-7.60 (2H, m), 9.34 (1H, brs)

ESI (LC-MS positive mode) m/z 322 (M+H).

Example 56

7-[(2-Aminoethyl)-methylamino]-3-phenyl-2H-isoquinolin-1-one monotrifluoroacetate

[Formula 72]

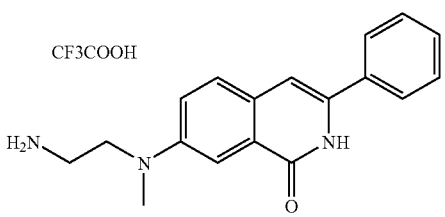

The above compound was synthesized by applying a method similar to that of Example 53 after applying a method similar to that of Example 52, using the 7-amino-3-phenyl-2H-isoquinolin-1-one obtained in Example 39 as a raw material.

$^1$H-NMR (270 MHz, DMSO-d$_6$) δ (ppm): 2.97-3.10 (5H, m), 3.64 (2H, t, J=6.8 Hz), 6.86 (1H, s), 7.32 (1H, dd, J=2.7, 8.9 Hz), 7.35-7.53 (4H, m), 7.62 (1H, d, J=8.9 Hz), 7.74-7.77 (2H, m), 11.32 (1H, brs)

ESI (LC-MS positive mode) m/z 294 (M+H−TFA).

Example 57

2-Chloro-N-(1-oxo-3-phenyl-1,2-dihydroisoquinolin-7-yl)acetamide

[Formula 73]

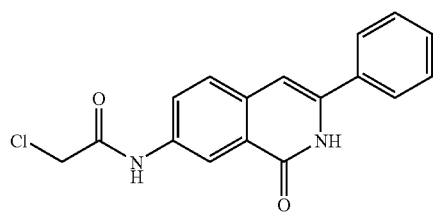

0.236 ml (1.69 mmol) of triethylamine and 0.101 ml (1.27 mmol) of chloroacetyl chloride were added in this order to 200 mg (0.85 mmol) of 7-amino-3-phenyl-2H-isoquinolin-1-one obtained in Example 39. The obtained mixture was stirred at a room temperature for 2 hours. Thereafter, 30 ml of 1 N hydrochloric acid was added to the reaction solution, and the mixture was then extracted with methylene chloride (30 ml×2). The extract was dried over anhydrous magnesium sulfate, and the solvent was then distilled away under reduced pressure. The precipitated solid was collected by filtration, and the filtrate was then washed with a suitable amount of ether, so as to obtain 229 mg (86%) of 2-chloro-N-(1-oxo-3-phenyl-1,2-dihydroisoquinolin-7-yl)acetamide in the form of a light brown solid.

$^1$H-NMR (270 MHz, DMSO-d$_6$) δ (ppm): 4.31 (2H, s), 6.90 (1H, s), 7.38-7.52 (3H, m), 7.70 (1H, d, J=8.6 Hz), 7.78 (2H, m), 7.87 (1H, d, J=2.4, 8.6 Hz), 8.55 (1H, d, J=2.4 Hz), 10.61 (1H, s), 11.49 (1H, s)

ESI (LC-MS positive mode) m/z 313 (M+H).

The following compounds (Examples 58 to 63) were synthesized by a method similar to that of Example 57, using the compound obtained in Example 38 or 39 as a raw material.

Example 58

2-Methoxy-N-(1-oxo-3-phenyl-1,2-dihydroisoquinolin-7-yl)acetamide

[Formula 74]

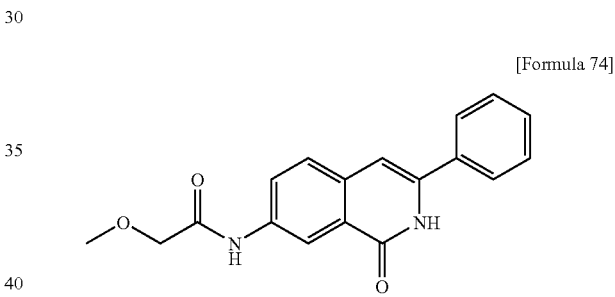

$^1$H-NMR (270 MHz, DMSO-d$_6$) δ (ppm): 3.41 (3H, s), 4.06 (2H, s), 6.89 (1H, s), 7.38-7.55 (3H, m), 7.67 (1H, d, J=8.6 Hz), 7.74-7.81 (2H, m), 7.90-7.98 (1H, m), 8.63 (1H, s), 10.08 (1H, s), 11.47 (1H, s)

EI (positive mode) m/z 308 (M$^+$).

Example 59

N-(1-Oxo-3-phenyl-1,2-dihydroisoquinolin-7-yl)-2-phenoxyacetamide

[Formula 75]

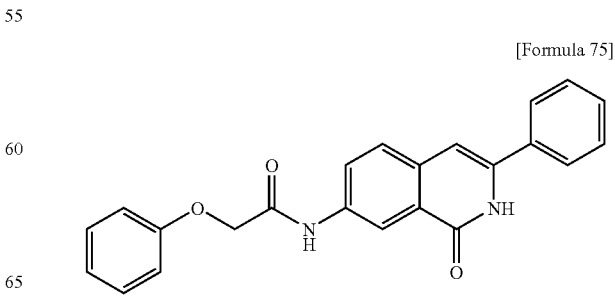

¹H-NMR (270 MHz, DMSO-d₆) δ (ppm): 4.76 (2H, s), 6.90 (1H, s), 6.92-7.09 (3H, m), 7.28-7.40 (2H, m), 7.41-7.53 (3H, m), 7.64-7.73 (1H, m), 7.74-7.82 (2H, m), 7.90-8.00 (1H, m), 8.59 (1H, s), 10.40 (1H, s), 11.49 (1H, s)
EI (positive mode) m/z 370 (M⁺).

Example 60

2-Benzyloxy-N-(1-oxo-3-phenyl-1,2-dihydroiso-quinolin-7-yl)acetamide

[Formula 76]

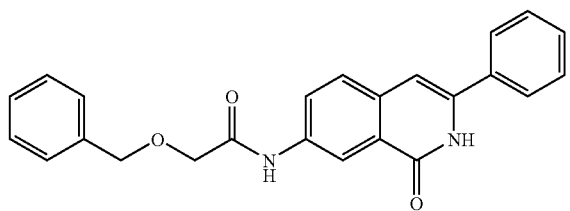

¹H-NMR (270 MHz, CDCl₃) δ (ppm): 4.15 (2H, s), 4.69 (2H, s), 6.76 (1H, s), 7.37-7.42 (5.5H, m), 7.46-7.55 (3H, m), 7.59-7.66 (3H, m), 8.17 (1H, d, J=1.98 Hz), 8.37 (1H, dd, J=2.31, 8.58 Hz), 8.60 (1H, brs), 8.98 (0.5H, brs)
EI-MS m/z 384 (M⁺).

Example 61

Ethyl[1-oxo-3-(2-trifluoromethylphenyl)-1,2-dihydroisoquinolin-7-yl]carbamate

[Formula 77]

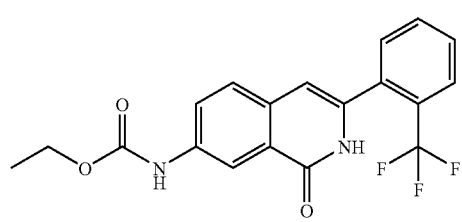

¹H-NMR (270 MHz, DMSO-d₆) δ (ppm): 1.28 (3H, t, J=6.8 Hz), 4.17 (2H, q, J=6.8 Hz), 6.41 (1H, s), 7.60-7.87 (6H, m), 8.38 (1H, s), 9.95 (1H, brs), 11.50 (1H, brs)
ESI (LC-MS positive mode) m/z 377 (M+H).

Example 62

Ethyl(1-oxo-3-phenyl-1,2-dihydroisoquinolin-7-yl)carbamate

[Formula 78]

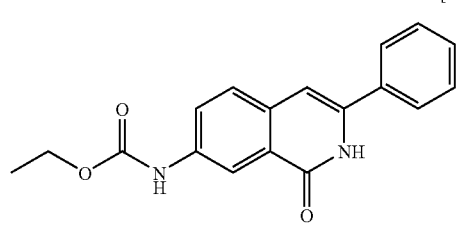

¹H-NMR (270 MHz, DMSO-d₆) δ (ppm): 1.28 (3H, t, J=7.0 Hz), 4.17 (2H, q, J=7.0 Hz), 6.86 (1H, s), 7.36-7.51 (3H, m), 7.65 (1H, d, J=8.9 Hz), 7.75-7.80 (3H, m), 8.38 (1H, s), 9.95 (1H, s), 11.43 (1H, s)
EI (positive mode) m/z 308 (M⁺).

Example 63 t-Butyl[(1-oxo-3-phenyl-1,2-dihydroisoquinolin-7-ylcarbamoyl)methyl]carbamate

[Formula 79]

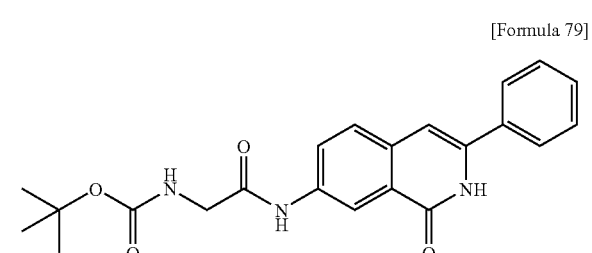

¹H-NMR (270 MHz, DMSO-d₆) δ (ppm): 1.41 (9H, s), 3.77 (2H, d, J=6.2 Hz), 6.88 (1H, s), 7.05-7.15 (1H, m), 7.41-7.50 (3H, m), 7.67 (1H, d, J=8.9 Hz), 7.72-7.80 (2H, m), 7.82-7.90 (1H, m), 8.54 (1H, s), 10.24 (1H, s), 11.45 (1H, m)
EI (positive mode) m/z 393 (M⁺).

Example 64

2-Amino-N-(1-oxo-3-phenyl-1,2-dihydroisoquinolin-7-yl)acetamide monotrifluoroacetate

[Formula 80]

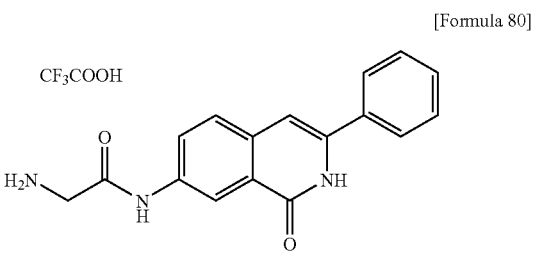

16 mg (0.041 mmol) of t-butyl[(1-oxo-3-phenyl-1,2-dihydroisoquinolin-7-ylcarbonyl)methyl]carbamate obtained in Example 63 was dissolved in a mixed solvent consisting of 1 ml of methylene chloride and 1 ml of methanol. Thereafter, 1 ml of trifluoroacetic acid was added thereto, and the obtained mixture was stirred under cooling on ice for 1 hour. Thereafter, diethyl ether-hexane was added to the reaction solution, and the generated solid was collected by filtration, so as to obtain 12 mg of 2-amino-N-(1-oxo-3-phenyl-1,2-dihydroisoquinolin-7-yl)acetamide monotrifluoroacetate in the form of a colorless solid.

¹H-NMR (270 MHz, DMSO-d₆) δ (ppm): 3.80 (2H, s), 6.90 (1H, s), 7.40-7.52 (3H, m), 7.67-7.81 (3H, m), 7.82-7.88 (1H, m), 8.14 (1H, brs), 8.53 (1H, s)
EI (positive mode) m/z 293 (M−TFA).

Example 65

2-Morpholin-4-yl-N-(1-oxo-3-phenyl-1,2-dihydroisoquinolin-7-yl)acetamide

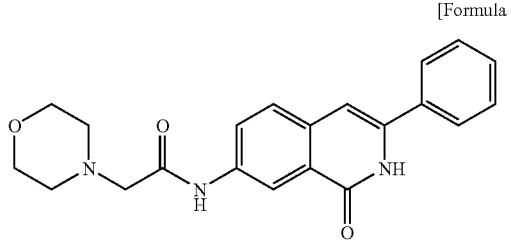

[Formula 81]

0.042 ml (0.47 mmol) of morpholine was added to a DMF solution containing 50 mg (0.16 mmol) of the 2-chloro-N-(1-oxo-3-phenyl-1,2-dihydroisoquinolin-7-yl)acetamide obtained in Example 57, and the obtained mixture was then stirred at 100° C. for 30 minutes. Thereafter, 30 ml of a 1 N sodium hydroxide aqueous solution was added to the reaction solution, and the mixture was then extracted with ethyl acetate (50 ml×2). The extract was washed with 30 ml of water, and was then dried over anhydrous magnesium sulfate. Thereafter, the solvent was distilled away under reduced pressure. The precipitated solid was collected by filtration, and the filtrate was then washed with a suitable amount of ether and hexane, so as to obtain 44 mg (76%) of 2-morpholin-4-yl-N-(1-oxo-3-phenyl-1,2-dihydroisoquinolin-7-yl)acetamide in the form of a colorless solid.

$^1$H-NMR (270 MHz, DMSO-d$_6$) δ (ppm): 2.51-2.56 (4H, m), 3.18 (2H, s), 3.66 (4H, t, J=4.7 Hz), 6.89 (1H, s), 7.38-7.52 (3H, m), 7.68 (1H, d, J=8.6 Hz), 7.72-7.80 (2H, m), 7.90-7.98 (1H, m), 8.57 (1H, d, J=2.4 Hz), 10.05 (1H, s), 11.46 (1H, s)

ESI (LC-MS positive mode) m/z 364 (M+H).

The following compounds (Examples 66 and 67) were synthesized by a method similar to that of Example 65.

Example 66

2-Dimethylamino-N-(1-oxo-3-phenyl-1,2-dihydroisoquinolin-7-yl)acetamide

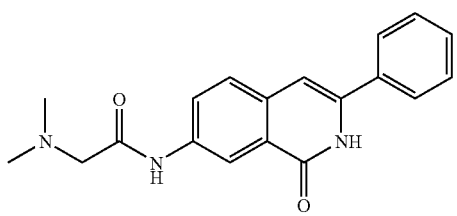

[Formula 82]

$^1$H-NMR (270 MHz, DMSO-d$_6$) δ (ppm): 2.30 (6H, s), 3.12 (2H, s), 6.88 (1H, s), 7.40-7.52 (3H, m), 7.66 (1H, d, J=8.6 Hz), 7.76-7.80 (2H, m), 7.92 (1H, dd, J=2.3, 8.6 Hz), 8.62 (1H, d, J=2.1 Hz), 10.04 (1H, s), 11.45 (1H, brs)

ESI (LC-MS positive mode) m/z 322 (M+H).

Example 67

2-(4-Methylpiperazin-1-yl)-N-(1-oxo-3-phenyl-1,2-dihydroisoquinolin-7-yl)acetamide

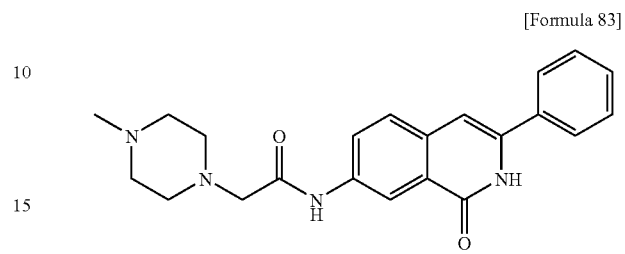

[Formula 83]

$^1$H-NMR (270 MHz, DMSO-d$_6$) δ (ppm): 2.18 (3H, s), 2.30-2.60 (8H, m), 3.16 (2H, s), 6.89 (1H, s), 7.38-7.52 (3H, m), 7.67 (1H, d, J=8.5 Hz), 7.78 (2H, dd, J=1.6, 7.8 Hz), 7.93 (1H, dd, J=2.1, 8.5 Hz), 8.56 (1H, d, J=2.1 Hz), 9.99 (1H, s), 11.46 (1H, brs)

ESI (LC-MS positive mode) m/z 377 (M+H).

Example 68

6-Morpholin-4-yl-3-phenyl-2H-isoquinolin-1-one

Step A

4-Chloro-2,N,N-trimethylbenzamide

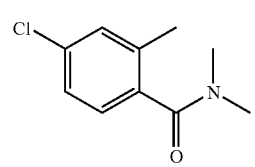

[Formula 84]

The above compound was synthesized by a method similar to that in Step A of Example 1, using 4-chloro-2-methylbenzoic acid as a raw material.

$^1$H-NMR (270 MHz, CDCl$_3$) δ (ppm): 2.27 (3H, s), 2.83 (3H, s), 3.13 (3H, s), 7.11 (1H, d, J=8.1 Hz), 7.17-7.23 (2H, m)

ESI (LC-MS positive mode) m/z 198 (M+H).

Step B

6-Chloro-3-phenyl-2H-isoquinolin-1-one

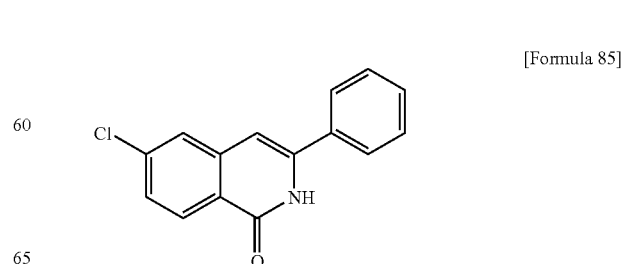

[Formula 85]

The above compound was synthesized by a method similar to that in Step B of Example 1, using the 4-chloro-2, N,N-trimethylbenzamide obtained in Step A as a raw material.

¹H-NMR (270 MHz, CDCl₃) δ (ppm): 6.69 (1H, s), 7.42 (1H, dd, J=1.9, 8.4 Hz), 7.44-7.59 (4H, m), 7.66-7.72 (2H, m), 8.32 (1H, d, J=8.4 Hz), 9.75 (1H, brs)

ESI (LC-MS positive mode) m/z 256 (M+H).

Step C

6-Morpholin-4-yl-3-phenyl-2H-isoquinolin-1-one

[Formula 86]

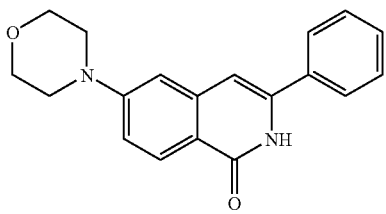

The above compound was synthesized by a method similar to that of Example 4, using the 6-chloro-3-phenyl-2H-isoquinolin-1-one obtained in Step B as a raw material.

¹H-NMR (270 MHz, CDCl₃) δ (ppm): 3.36 (4H, t, J=5.1 Hz), 3.90 (4H, t, J=5.1 Hz), 6.64 (1H, s), 6.87 (1H, d, J=2.6 Hz), 7.09 (1H, dd, J=2.6, 8.9 Hz), 7.42-7.55 (3H, m), 7.61-7.67 (2H, m), 8.27 (1H, d, J=8.9 Hz), 8.90 (1H, brs)

ESI (LC-MS positive mode) m/z 307 (M+H).

The following compounds (Examples 69 to 73) were synthesized by a method similar to that of Example 4, using the 7-chloro-3-(2-trifluoromethylphenyl)-2H-isoquinolin-1-one obtained in Step B of Example 1 as a starting material.

Example 69

(4aS,8aR)-3'-(2-Trifluoromethylphenyl)-3,4,4a,5,6,7,8,8a-octahydro-1H, 2'H-[2,7']biisoquinolinyl-1'-one

[Formula 87]

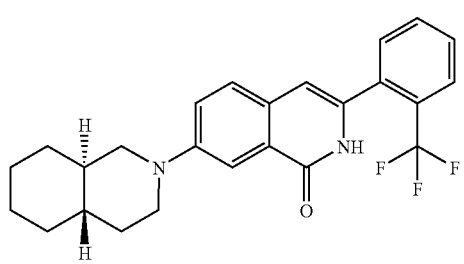

¹H-NMR (400 MHz, CDCl₃) δ (ppm): 1.02-1.05 (3H, m), 1.26-1.49 (4H, m), 1.68 (3H, m), 1.78 (2H, m), 2.47 (1H, t, J=11.8 Hz), 2.83 (1H, dt, J=2.8, 12.4 Hz), 3.72 (1H, d, J=12.4 Hz), 3.91 (1H, d, J=12.0 Hz), 6.44 (1H, s), 7.38 (1H, dd, J=2.8, 8.8 Hz), 7.45 (1H, d, J=8.8 Hz), 7.53 (1H, d, J=7.6 Hz), 7.58 (1H, t, J=7.6 Hz), 7.65 (1H, t, J=7.0 Hz), 7.79-7.81 (2H, m), 8.35 (1H, brs)

ESI (LC-MS positive mode) m/z 427 (M+H).

Example 70

7-((2S,6R)-2,6-Dimethylmorpholin-4-yl)-3-(2-trifluoromethylphenyl)-2H-isoquinolin-1-one

[Formula 88]

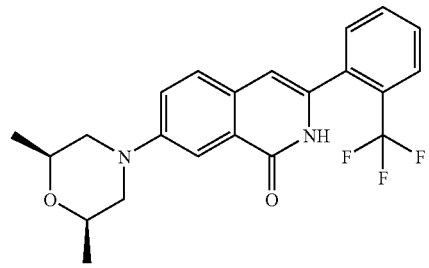

¹H-NMR (400 MHz, CDCl₃) δ (ppm): 1.30 (6H, d, J=6.4 Hz), 2.53 (2H, t, J=11.4 Hz), 3.64 (2H, d, J=10.8 Hz), 3.81-3.88 (2H, m), 6.46 (1H, s), 7.36 (1H, dd, J=2.8, 8.8 Hz), 7.49 (1H, d, J=8.8 Hz), 7.54 (1H, d, J=7.6 Hz), 7.59 (1H, t, J=7.6 Hz), 7.66 (1H, t, J=7.2 Hz), 7.78-7.82 (2H, m), 8.41 (1H, brs)

ESI (LC-MS positive mode) m/z 403 (M+H).

Example 71

7-((S)-2-Hydroxymethylpyrrolidin-1-yl)-3-(2-trifluoromethylphenyl)-2H-isoquinolin-1-one

[Formula 89]

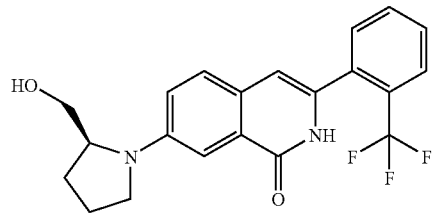

¹H-NMR (400 MHz, CDCl₃) δ (ppm): 2.04-2.15 (4H, m), 2.45. (1H, brs), 3.24-3.29 (1H, m), 3.62 (2H, t, J=6.6 Hz), 3.80 (1H, d, J=11.2 Hz), 4.01 (1H, brs), 6.45 (1H, s), 7.15 (1H, dd, J=3.2, 8.8 Hz), 7.46 (1H, d, J=8.8 Hz), 7.52-7.65 (4H, m), 7.79 (1H, d, J=7.6 Hz), 8.58 (1H, brs)

ESI (LC-MS positive mode) m/z 389 (M+H).

Example 72

7-((R)-2-Hydroxymethylpyrrolidin-1-yl)-3-(2-trifluoromethylphenyl)-2H-isoquinolin-1-one

[Formula 90]

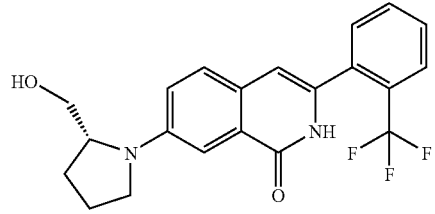

$^1$H-NMR (400 MHz, CDCl$_3$) δ (ppm): 2.06-2.15 (4H, m), 2.50 (1H, brs), 3.24-3.29 (1H, m), 3.62 (2H, t, J=8.8 Hz), 3.81 (1H, d, J=10.4 Hz), 4.00 (1H, brs), 6.45 (1H, s), 7.14 (1H, dd, J=2.6, 8.8 Hz), 7.45 (1H, d, J=8.8 Hz), 7.52-7.65 (4H, m), 7.79 (1H, d, J=7.6 Hz), 8.61 (1H, brs)

ESI (LC-MS positive mode) m/z 389 (M+H).

Example 73

7-Azetidin-1-yl-3-(2-trifluoromethylphenyl)-2H-isoquinolin-1-one

[Formula 91]

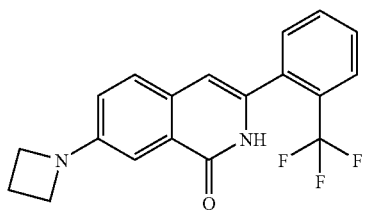

$^1$H-NMR (400 MHz, CDCl$_3$) δ (ppm): 2.43 (2H, quintet, J=7.2 Hz), 4.01 (4H, t, J=7.4 Hz), 6.44 (1H, s), 6.86 (1H, dd, J=2.4, 8.4 Hz), 7.34 (1H, d, J=2.4 Hz), 7.43 (1H, d, J=8.8 Hz), 7.54 (1H, t, J=6.4 Hz), 7.58 (1H, d, J=7.6 Hz), 7.64 (1H, t, J=7.0 Hz), 7.80 (1H, d, J=8.0 Hz), 8.34 (1H, brs)

ESI (LC-MS positive mode) m/z 345 (M+H).

Example 74

4a-Hydroxy-3'-(2-trifluoromethylphenyl)-3,4,4a,5,6,7,8,8a-octahydro-1H, 2'H-[2,7']biisoquinolinyl-1'-one

[Formula 92]

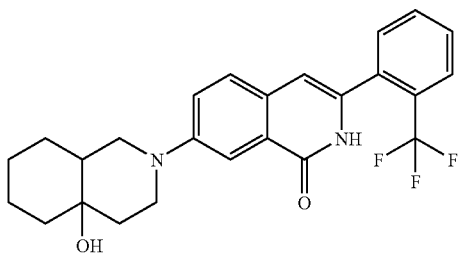

The above compound was synthesized by a method similar to that of Example 20, using the 7-chloro-3-(2-trifluoromethylphenyl)-2H-isoquinolin-1-one prepared in Step B of Example 1 as a starting material.

$^1$H-NMR (400 MHz, CDCl$_3$) δ (ppm): 1.30-1.85 (11H, m), 2.15-2.22 (1H, m), 3.38 (2H, t, J=11.2 Hz), 3.51 (2H, d, J=11.2 Hz), 6.44 (1H, s), 7.35 (1H, dd, J=2.8, 8.8 Hz), 7.45 (1H, d, J=8.8 Hz), 7.54 (1H, t, J=7.2 Hz), 7.60 (1H, d, J=8.0 Hz), 7.65 (1H, d, J=7.6 Hz), 7.78-7.82 (2H, m), 8.31 (1H, brs)

ESI (LC-MS positive mode) m/z 443 (M+H).

Example 75

Methyl 1-[1-oxo-3-(2-trifluoromethylphenyl)-1,2-dihydroisoquinolin-7-yl]piperidin-4-carboxylate

[Formula 93]

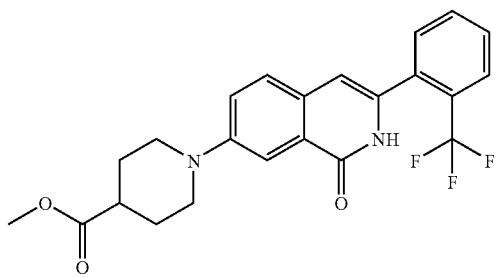

150 mg (0.463 mmol) of the 7-chloro-3-(2-trifluoromethylphenyl)-2H-isoquinolin-1-one prepared in Step B of Example 1; 22 mg (0.056 mmol) of 2-dicyclohexylphosphino-2'-(N,N-dimethylamino)biphenyl; 21.1 mg (0.023 mmol) of tris(dibenzylideneacetone)dipalladium; and 603 mg (1.85 mmol) of cesium carbonate were mixed. The obtained mixture was dried under reduced pressure for 2 hours. Thereafter, 188 µl (1.39 mmol) of methyl isonipecotate and 2.32 ml of dimethoxyethane were added to the resultant, and the obtained mixture was then stirred under heating to reflux for 17 hours. Thereafter, a saturated ammonium chloride aqueous solution was added to the reaction solution, and the mixture was then extracted with ethyl acetate. The extract was dried over anhydrous sodium sulfate, and the solvent was then distilled away under reduced pressure. The obtained residue was purified by silica gel column chromatography (hexane:ethyl acetate=1:1), so as to obtain 17.5 mg (8.8%) of methyl 1-[1-oxo-3-(2-trifluoromethylphenyl)-1,2-dihydroisoquinolin-7-yl]piperidin-4-carboxylate in the form of a light yellow solid.

$^1$H-NMR (400 MHz, CDCl$_3$) δ (ppm): 1.91-2.00 (2H, m), 2.01-2.10 (2H, m), 2.50-2.55 (1H, m), 2.90-3.00 (2H, m), 3.72 (3H, s), 3.82-3.85 (2H, m), 6.45 (1H, s), 7.35-7.45 (1H, m), 7.48 (1H, d, J=8.0 Hz), 7.54 (1H, d, J=7.2 Hz), 7.59 (1H, t, J=7.6 Hz), 7.65 (1H, t, J=7.6 Hz), 7.75-7.85 (2H, m), 8.34 (1H, brs)

ESI (LC-MS positive mode) m/z 431 (M+H).

Example 76

7-(4-Hydroxypiperidin-1-yl)-3-naphthalen-1-yl-2H-isoquinolin-1-one

Step A

7-Chloro-3-naphthalen-1-yl-2H-isoquinolin-1-one

[Formula 94]

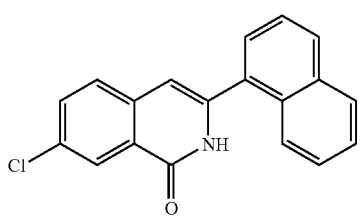

The above compound was synthesized by a method similar to that in Step B of Example 1, using the 5-chloro-2, N-dimethylbenzamide prepared in Step A of Example 1 as a starting material.

¹H-NMR (270 MHz, CDCl₃) δ (ppm): 6.67 (1H, s), 7.50-7.70 (7H, m), 7.91-8.05 (3H, m)8.40-8.45 (1H, m)

ESI (LC-MS positive mode) m/z 306 (M+H).

Step B 7-(4-Hydroxypiperidin-1-yl)-3-naphthalen-1-yl-2H-isoquinolin-1-one

[Formula 95]

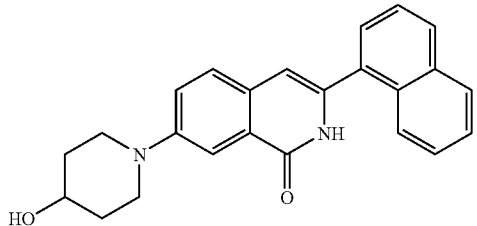

The above compound was synthesized by a method similar to that of Example 20, using the 7-chloro-3-naphthalen-1-yl-2H-isoquinolin-1-one prepared in Step B as a starting material.

¹H-NMR (400 MHz, CDCl₃) δ (ppm): 1.48-1.52 (1H, m), 1.70-1.80 (2H, m), 2.03-2.10 (2H, m), 3.05-3.15 (2H, m), 3.75-3.85 (2H, m), 3.90-4.00 (1H, m), 6.64 (1H, s), 7.41-7.70 (6H, m), 7.93-7.96 (3H, m), 8.06 (1H, d, J=7.8 Hz), 8.49 (1H, brs)

ESI (LC-MS positive mode) m/z 371 (M+H).

Example 77

7-(1,4-Dioxa-8-azaspiro[4.5]deca-8-yl)-3-(2-trifluoromethylphenyl)-2H-isoquinolin-1-one

[Formula 96]

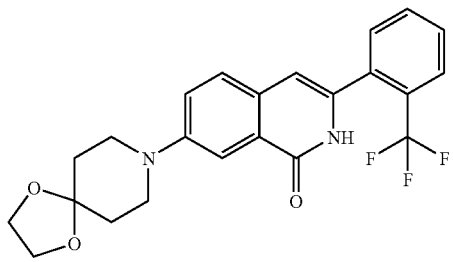

The above compound was synthesized by a method similar to that of Example 4, using the 7-chloro-3-(2-trifluoromethylphenyl)-2H-isoquinolin-1-one prepared in Step B of Example 1 as a starting material.

¹H-NMR (270 MHz, CDCl₃) δ (ppm): 1.86 (4H, t, J=5.6 Hz), 3.51 (4H, t, J=5.6 Hz), 4.01 (4H, s), 6.45 (1H, s), 7.38 (1H, dd, J=2.4, 8.7 Hz), 7.43-7.69 (4H, m), 7.76-7.84 (2H, m), 8.36 (1H, brs)

ESI (LC-MS positive mode) m/z 431 (M+H).

Example 78

7-(2-Hydroxymethylmorpholin-4-yl)-3-(2-trifluoromethylphenyl)-2H-isoquinolin-1-one

[Formula 97]

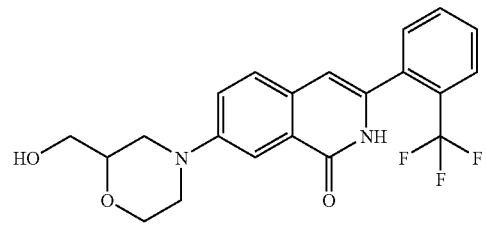

The above compound was synthesized by a method similar to that of Example 20, using the 7-chloro-3-(2-trifluoromethylphenyl)-2H-isoquinolin-1-one prepared in Step B of Example 1 as a starting material.

¹H-NMR (270 MHz, CDCl₃) δ (ppm): 2.25-2.38 (1H, m), 2.77 (1H, t, J=11.6 Hz), 2.93 (1H, dt, J=3.3, 11.9 Hz), 3.47-3.91 (6H, m), 4.07 (1H, dd, J=2.3, 11.6 Hz), 6.47 (1H, m), 7.37 (1H, dd, J=2.6, 8.9 Hz), 7.46-7.70 (4H, m), 7.77-7.83 (2H, m), 8.79 (1H, brs)

ESI (LC-MS positive mode) m/z 405 (M+H).

Example 79

7-(4-Hydroxy-4-hydroxymethylpiperidin-1-yl)-3-(2-trifluoromethylphenyl)-2H-isoquinolin-1-one Step A 7-(4-Oxopiperidin-1-yl)-3-(2-trifluoromethylphenyl)-2H-isoquinolin-1-one

[Formula 98]

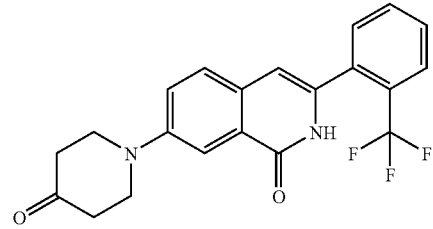

70 mg (0.163 mmol) of the 7-(1,4-dioxa-8-azaspiro[4.5]deca-8-yl)-3-(2-trifluoromethylphenyl)-2H-isoquinolin-1-one obtained in Example 77 was suspended in 3 ml of 1 N hydrochloric acid. The suspension was stirred under heating to reflux overnight. Thereafter, 2.9 ml of a 1 N sodium hydroxide aqueous solution and a saturated sodium bicarbonate solution were added to the reaction solution, and the obtained reaction solution was then extracted with ethyl acetate. The extract was dried over anhydrous sodium sulfate and was then concentrated. The obtained residue was purified by silica gel column chromatography (hexane:ethyl acetate=1:3 to 1:4), so as to obtain 55.9 mg (89%) of 7-(4-oxopiperidin-1-yl)-3-(2-trifluoromethylphenyl)-2H-isoquinolin-1-one in the form of a light yellow solid.

¹H-NMR (270 MHz, CDCl₃) δ (ppm): 2.59 (4H, t, J=6.2 Hz), 3.75 (4H, t, J=6.2 Hz), 6.48 (1H, s), 7.41 (1H, dd, J=2.5, 8.7 Hz), 7.47-7.70 (4H, m), 7.75-7.85 (2H, m), 9.12-9.60 (1H, brs)

ESI (LC-MS positive mode) m/z 387 (M+H).

Step B

7-(4-Hydroxy-4-hydroxymethylpiperidin-1-yl)-3-(2-trifluoromethylphenyl)-2H-isoquinolin-1-one

[Formula 99]

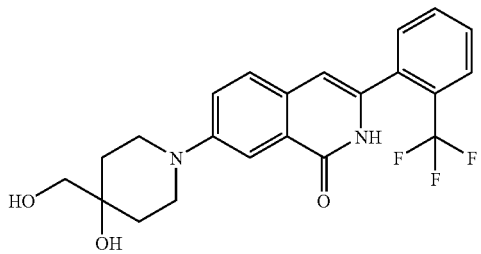

30 mg (0.0776 mmol) of the 7-(4-oxopiperidin-1-yl)-3-(2-trifluoromethylphenyl)-2H-isoquinolin-1-one obtained in Step A, 51.3 mg (0.233 mmol) of trimethylsulfoxonium iodide, and 26.1 mg (0.233 mmol) of sodium t-butoxide were dissolved in 1.16 ml of DMSO. The obtained solution was stirred at a room temperature overnight. Thereafter, water was added to the reaction solution, and the mixture was extracted with ethyl acetate. The extract was dried over anhydrous sodium sulfate, and was then concentrated. The obtained residue was purified by silica gel column chromatography (hexane:ethyl acetate=1:3), so as to obtain 16.6 mg of a light yellow solid.

The obtained solid was dissolved in 1 ml of 1,4-dioxane, and 1 ml of a 1 N sodium hydroxide aqueous solution was added thereto, followed by stirring under heating for 2 hours. Thereafter, 1 ml of 1 N hydrochloric acid and a saturated ammonium chloride aqueous solution were added to the reaction solution, and the obtained mixture was then extracted with ethyl acetate. The extract was dried over anhydrous sodium sulfate, and was then concentrated. The obtained residue was purified by silica gel column chromatography (methylene chloride:methanol=12:1 to 10:1), so as to obtain 12.2 mg (37%) of 7-(4-hydroxy-4-hydroxymethylpiperidin-1-yl)-3-(2-trifluoromethylphenyl)-2H-isoquinolin-1-one in the form of a colorless solid.

$^1$H-NMR (270 MHz, DMSO-d$_6$) δ (ppm): 1.40-1.51 (2H, m), 1.64-1.78 (2H, m), 3.07-3.24 (4H, m), 3.55-3.65 (2H, m), 4.25 (1H, s), 4.60 (1H, t, J=5.8 Hz), 6.37 (1H, s), 7.43-7.90 (7H, m), 11.37 (1H, brs)

ESI (LC-MS positive mode) m/z 419 (M+H).

Example 80

3-(4-Methoxyphenyl)-7-morpholin-4-yl-2H-isoquinolin-1-one

Step A

5-Chloro-2,N,N-trimethylbenzamide

[Formula 100]

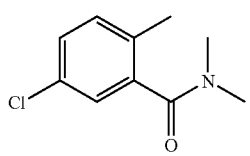

The above compound was synthesized by a method similar to that in Step A of Example 1, using 5-chloro-2-methylbenzoic acid as a starting material.

$^1$H-NMR (270 MHz, CDCl$_3$) δ (ppm): 2.25 (3H, s), 2.85 (3H, s), 3.12 (3H, s), 7.15 (1H, d, J=8.4 Hz) 7.16 (1H, d, J=2.3 Hz), 7.24 (1H, dd, J=2.3, 8.4 Hz)

ESI (LC-MS positive mode) m/z 198 (M+H).

Step B

2,N,N-Trimethyl-5-morpholin-4-ylbenzamide

[Formula 101]

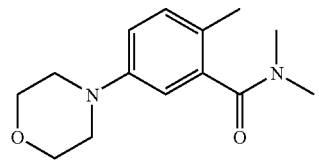

The above compound was synthesized by a method similar to that of Example 4, using the 5-chloro-2, N,N-trimethylbenzamide prepared in Step A as a starting material.

$^1$H-NMR (400 MHz, CDCl$_3$) δ (ppm): 2.19 (3H, s), 2.84 (3H, s), 3.09-3.13 (7H, m), 3.85 (4H, t, J=4.1 Hz), 6.72 (1H, d, J=2.6 Hz), 6.83 (1H, dd, J=2.3, 8.2 Hz), 7.10 (1H, d, J=8.2 Hz)

ESI (LC-MS positive mode) m/z 249 (M+H).

Step C

3-(4-Methoxyphenyl)-7-morpholin-4-yl-2H-isoquinolin-1-one

[Formula 102]

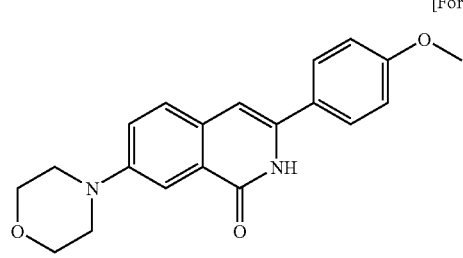

The above compound was synthesized by a method similar to that in Step B of Example 1, using the 2,N,N-trimethyl-5-morpholin-4-ylbenzamide prepared in Step B as a starting material.

$^1$H-NMR (400 MHz, CDCl$_3$) δ (ppm): 3.30 (4H, t, J=4.9 Hz), 3.87 (3H, s), 3.90 (4H, t, J=4.9 Hz), 6.64 (1H, s), 7.01 (2H, d, J=8.3 Hz), 7.34 (1H, dd, J=2.7, 9.0 Hz), 7.49-7.55 (3H, m), 7.78 (1H, d, J=2.4 Hz), 8.60 (1H, brs)

ESI (LC-MS positive mode) m/z 337 (M+H).

The following compounds (Examples 81 to 89) were synthesized by a method similar to that in Step B of Example 1, using the 2,N,N-trimethyl-5-morpholin-4-ylbenzamide prepared in Step B of Example 80 as a starting material.

Example 81

3-(2-Methoxyphenyl)-7-morpholin-4-yl-2H-isoquinolin-1-one

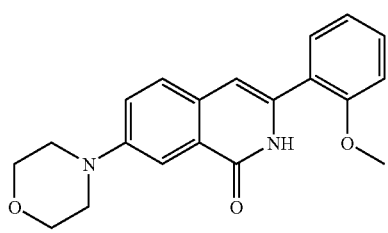

[Formula 103]

$^1$H-NMR (400 MHz, CDCl$_3$) δ (ppm): 3.31 (4H, t, J=4.9 Hz), 3.91 (4H, t, J=4.9 Hz), 3.93 (3H, s), 6.68 (1H, d, J=2.0 Hz), 7.00-7.09 (2H, m), 7.32-7.58 (4H, m), 7.80 (1H, d, J=2.9 Hz), 9.42 (1H, brs)
ESI (LC-MS positive mode) m/z 337 (M+H).

Example 82

3-(2-Ethylphenyl)-7-morpholin-4-yl-2H-isoquinolin-1-one

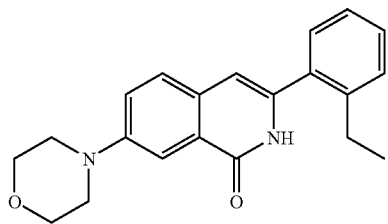

[Formula 104]

$^1$H-NMR (400 MHz, CDCl$_3$) δ (ppm): 1.19 (3H, t, J=7.8 Hz), 2.71 (2H, q, J=7.3 Hz), 3.31 (4H, t, J=4.9 Hz), 3.91 (4H, t, J=4.9 Hz), 6.42 (1H, s), 7.30-7.51 (6H, m), 7.81 (1H, d, J=2.4 Hz), 8.26 (1H, brs)
ESI (LC-MS positive mode) m/z 335 (M+H).

Example 83

3-(2-Methylsulfanylphenyl)-7-morpholin-4-yl-2H-isoquinolin-1-one

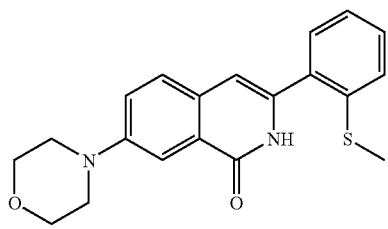

[Formula 105]

$^1$H-NMR (400 MHz, CDCl$_3$) δ (ppm): 2.46 (3H, s), 3.30 (4H, t, J=4.9 Hz), 3.90 (4H, t, J=4.9 Hz), 6.55 (1H, s), 7.23-7.42 (5H, m), 7.51 (1H, d, J=8.3 Hz), 7.81 (1H, d, J=2.4 Hz), 8.72 (1H, brs)
ESI (LC-MS positive mode) m/z 353 (M+H).

Example 84

3-(2-Bromophenyl)-7-morpholin-4-yl-2H-isoquinolin-1-one

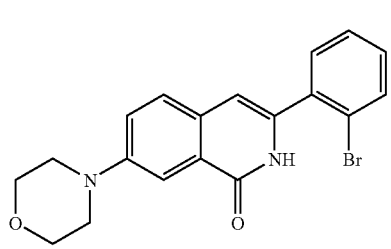

[Formula 106]

ESI (LC-MS positive mode) m/z 385 (M+H), 387 (M+H+2).

Example 85

7-Morpholin-4-yl-3-(2-piperidin-1-ylphenyl)-2H-isoquinolin-1-one

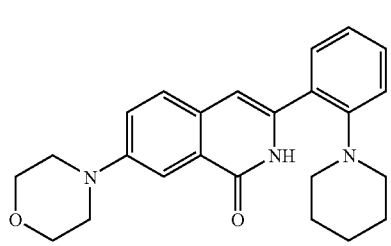

[Formula 107]

$^1$H-NMR (400 MHz, CDCl$_3$) δ (ppm): 1.50-1.60 (2H, m), 1.75-1.80 (4H, m), 2.90-2.94 (4H, m), 3.31 (4H, t, J=4.9 Hz), 3.91 (4H, t, J=4.9 Hz), 6.71 (1H, s), 7.12-7.23 (2H, m), 7.32-7.38 (2H, m), 7.54 (1H, d, J=8.3 Hz), 7.61 (1H, dd, J=1.5, 7.8 Hz), 7.83 (1H, d, J=2.4 Hz), 11.50 (1H, brs)
ESI (LC-MS positive mode) m/z 390 (M+H).

Example 86

7-Morpholin-4-yl-3-(2-morpholin-4-ylphenyl)-2H-isoquinolin-1-one

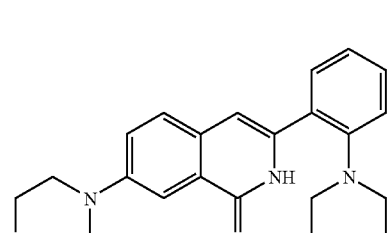

[Formula 108]

$^1$H-NMR (400 MHz, CDCl$_3$) δ (ppm): 2.97-3.01 (4H, m), 3.30-3.33 (4H, m), 3.87-3.92 (8H, m), 6.69 (1H, d, J=2.0 Hz), 7.14-7.20 (2H, m), 7.33-7.41 (2H, m), 7.52-7.60 (2H, m), 7.81 (1H, d, J=2.4 Hz), 10.9 (1H, brs)

ESI (LC-MS positive mode) m/z 392 (M+H).

Example 87

Methyl 2-hydroxy-3-[1-oxo-3-(2-trifluoromethylphenyl)-1,2-dihydroisoquinolin-7-ylamino]propionate

[Formula 109]

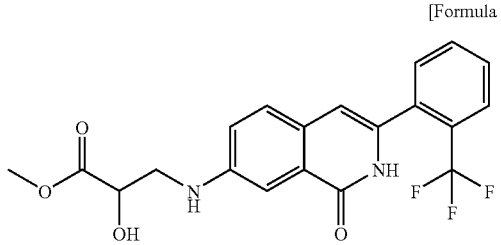

550 mg (1.81 mmol) of the 7-amino-3-(2-trifluoromethylphenyl)-2H-isoquinolin-1-one obtained in Example 38 was added to 3.6 ml of a methanol solution containing 185 mg (1.81 mmol) of a known epoxide described in publications. The obtained mixture was stirred at 70° C. for 14 hours. Thereafter, the reaction solution was concentrated. The obtained residue was purified by silica gel column chromatography (ethyl acetate:hexane=1:1 to 3:1), so as to obtain 356 mg (48%) of methyl 2-hydroxy-3-[1-oxo-3-(2-trifluoromethylphenyl)-1,2-dihydroisoquinolin-7-ylamino]propionate in the form of a light yellow foaming substance.

$^1$H-NMR (270 MHz, DMSO-$d_6$) δ (ppm): 3.28-3.39 (1H, m), 3.40-3.52 (1H, m), 3.66 (3H, s), 4.26-4.34 (1H, m), 5.78 (1H, d, J=5.7 Hz), 6.19 (1H, t, J=6.2 Hz), 7.14 (1H, dd, J=2.6, 8.5 Hz), 7.28 (1H, d, J=2.4 Hz), 7.41 (1H, d, J=8.6 Hz), 7.58 (1H, d, J=7.3 Hz), 7.63-7.79 (3H, m), 7.80-7.87 (1H, m), 11.27 (1H, s)

ESI (LC-MS positive mode) m/z 407 (M+H).

Example 88

3-(3,5-Dimethoxyphenyl)-7-morpholin-4-yl-2H-isoquinolin-1-one

[Formula 110]

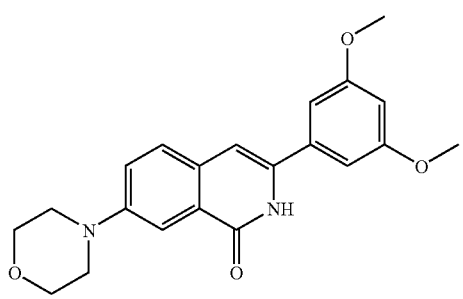

$^1$H-NMR (400 MHz, CDCl$_3$) δ (ppm): 3.31 (4H, t, J=4.9 Hz), 3.86 (6H, s), 3.91 (4H, t, J=4.9 Hz), 6.52 (1H, s), 6.70-6.75 (3H, m), 7.35 (1H, dd, J=2.4, 8.8 Hz), 7.53 (1H, d, J=8.8 Hz), 7.79 (1H, d, J=2.0 Hz), 8.76 (1H, brs)

ESI (LC-MS positive mode) m/z 367 (M+H).

Example 89

7-Morpholin-4-yl-3-(3,4,5-trimethoxyphenyl)-2H-isoquinolin-1-one

[Formula 111]

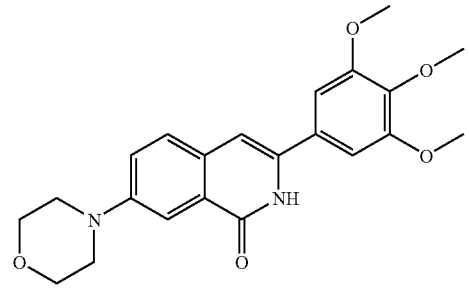

$^1$H-NMR (400 MHz, CDCl$_3$) δ (ppm): 3.32 (4H, t, J=4.8 Hz), 3.91 (3H, s), 3.91 (4H, t, J=4.8 Hz), 3.95 (6H, s), 6.66 (1H, s), 6.80 (2H, s), 7.36 (1H, dd, J=1.5, 8.3 Hz), 7.54 (1H, d, J=8.8 Hz), 7.78 (1H, d, J=2.4 Hz), 8.86 (1H, brs)

ESI (LC-MS positive mode) m/z 397 (M+H).

The following compounds (Examples 90 to 96) were synthesized by applying a method similar to that in Step B of Example 1 and then applying a method similar to that of Example 20, using the 5-chloro-2,N-dimethylbenzamide obtained in Step A of Example 1 as a starting material.

Example 90

7-(3-Hydroxypiperidin-1-yl)-3-(4-methoxy-2-methylphenyl)-2H-isoquinolin-1-one

[Formula 112]

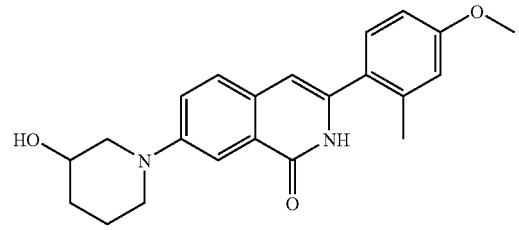

$^1$H-NMR (270 MHz, CDCl$_3$) δ (ppm): 1.58-2.00 (4H, m), 2.35 (3H, s), 248-2.63 (1H, m), 3.13-3.22 (2H, m), 3.27-3.34 (1H, m), 3.51 (1H, dd, J=12.0, 3.0 Hz), 3.83 (3H, s), 3.93-4.02 (1H, m), 6.37 (1H, s), 6.78-6.82 (2H, m), 7.27 (1H, d, J=8.0 Hz), 7.37 (1H, dd, J=8.5, 2.5 Hz), 7.45 (1H, d, J=8.5 Hz), 7.81 (1H, d, J=2.5 Hz), 8.87 (1H, brs)

ESI (LC-MS positive mode) m/z 365 (M+H).

Example 91

7-(3-Hydroxypiperidin-1-yl)-3-(2-morpholin-4-ylphenyl)-2H-isoquinolin-1-one

[Formula 113]

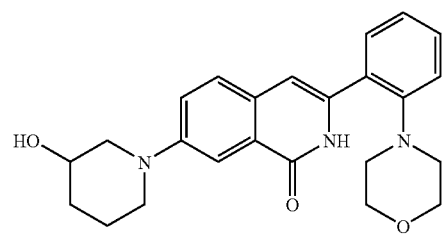

¹H-NMR (270 MHz, CDCl₃) δ (ppm): 1.66-1.77 (2H, m), 1.83-2.01 (2H, m), 2.10 (1H, d, J=7.0 Hz), 2.96-3.00 (4H, m), 3.17-3.31 (3H, m), 3.51 (1H, dd, J=12.0, 3.0 Hz), 3.86-3.90 (4H, m), 3.93-4.01 (1H, m), 6.69 (1H, d, J=1.5 Hz), 7.13-7.21 (2H, m), 7.35-7.42 (2H, m), 7.51 (1H, d, J=9.0 Hz), 7.59 (1H, dd, J=8.0, 1.5 Hz), 7.84 (1H, d, J=2.5 Hz), 10.87 (1H, brs)
ESI (LC-MS positive mode) m/z 406 (M+H).

Example 92

7-(3-Hydroxypiperidin-1-yl)-3-o-tolyl-2H-isoquinolin-1-one

[Formula 114]

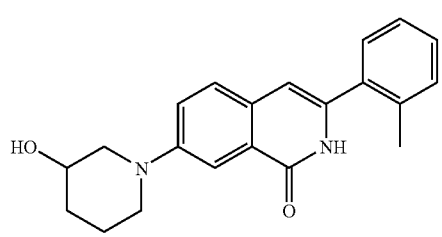

¹H-NMR (270 MHz, CDCl₃) δ (ppm): 1.60-1.79 (2H, m), 1.84-2.02 (2H, m), 2.25 (1H, d, J=7.0 Hz), 2.38 (3H, s), 3.16-3.33 (3H, m), 3.50 (1H, dd, J=12.0, 3.0 Hz), 3.93-4.03 (1H, m), 6.41 (1H, s), 7.25-7.40 (5H, m), 7.47 (1H, d, J=8.5 Hz), 7.84 (1H, d, J=2.5 Hz), 8.48 (1H, brs)
ESI (LC-MS positive mode) m/z 335 (M+H).

Example 93

7-(3-Hydroxypiperidin-1-yl)-3-(6-methoxybenzothiazol-2-yl)-2H-isoquinolin-1-one

[Formula 115]

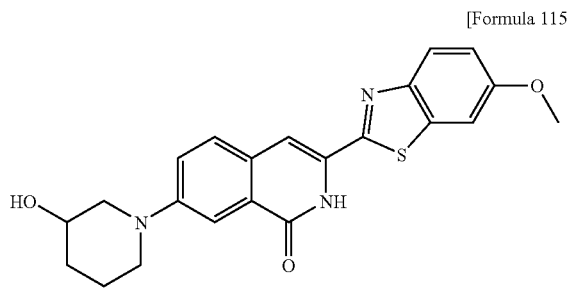

¹H-NMR (500 MHz, DMSO-d₆) δ (ppm): 1.34-1.41 (1H, m), 1.50-1.57 (1H, m), 1.77-1.81 (1H, m), 1.90-1.94 (1H, m), 2.74-2.78 (1H, m), 2.88-2.93 (1H, m), 3.17 (1H, d, J=3.0 Hz), 3.60-3.70 (2H, m), 3.78 (1H, dd, J=6.5, 3.0 Hz), 3.78 (3H, s), 7.16 (1H, dd, J=9.0, 3.0 Hz), 7.32 (1H, brs), 7.48 (1H, dd, J=8.5, 3.0 Hz), 7.56 (1H, d, J=3.0 Hz), 7.73 (1H, d, J=8.5 Hz), 7.75 (1H, d, J=3.0 Hz), 7.94 (1H, d, J=9.0 Hz)
ESI (LC-MS positive mode) m/z 408 (M+H).

Example 94

7-(3-Hydroxypiperidin-1-yl)-3-(2-morpholin-4-ylmethylphenyl)-2H-isoquinolin-1-one It is to be noted that 2-morpholin-4-ylmethylbenzonitrile used in a coupling reaction was prepared from cyanobenzyl bromide and morpholine in accordance with known methods described in publications (for example, Preparation, Bulletin de l'Academie Polonaise des Sciences, serie des Sciences Chimiques (1972), 20(5), 405-9; WO2003/048164; etc.).

[Formula 116]

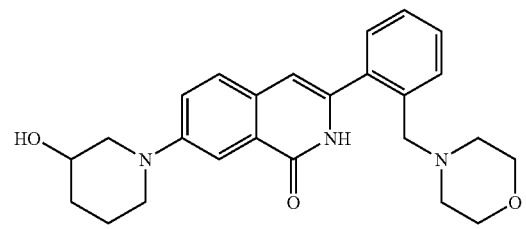

¹H-NMR (270 MHz, CDCl₃) δ (ppm): 1.62-1.74 (2H, m), 1.82-2.00 (2H, m), 2.07-2.17 (1H, m), 2.61-2.71 (4H, m), 3.15-3.31 (3H, m), 3.48 (1H, dd, J=12.0, 3.0 Hz), 3.51 (2H, s), 3.90-4.00 (5H, m), 6.59 (1H, s), 7.25-7.47 (4H, m), 7.51 (1H, d, J=9.0 Hz), 7.68 (1H, dd, J=7.5, 1.5 Hz), 7.83 (1H, d, J=2.5 Hz), 13.25 (1H, brs)
ESI (LC-MS positive mode) m/z 420 (M+H).

Example 95

7-(4-Hydroxypiperidin-1-yl)-3-[2-(methylphenylamino)phenyl]-2H-isoquinolin-1-one

[Formula 117]

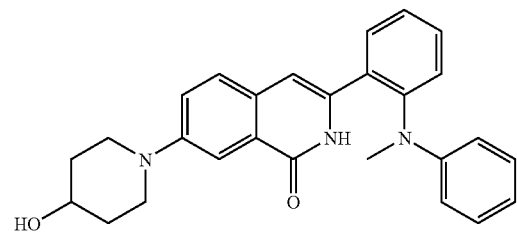

¹H-NMR (400 MHz, CDCl₃) δ (ppm): 1.50 (1H, m), 1.65-1.73 (2H, m), 2.00-2.05 (2H, m), 3.01-3.09 (2H, m), 3.11 (3H, s), 3.68-3.74 (2H, m), 3.85-3.95 (1H, m), 6.57 (1H, s), 6.78-6.82 (3H, m), 7.16-7.25 (2H, m), 7.27-7.45 (5H, m), 7.61 (1H, d, J=7.1 Hz), 7.75 (1H, s), 9.21 (1H, brs)
ESI (LC-MS positive mode) m/z 426 (M+H).

Example 96

3-(4-Fluoro-2-trifluoromethylphenyl)-7-(4-hydroxypiperidin-1-yl)-2H-isoquinolin-1-one

[Formula 118]

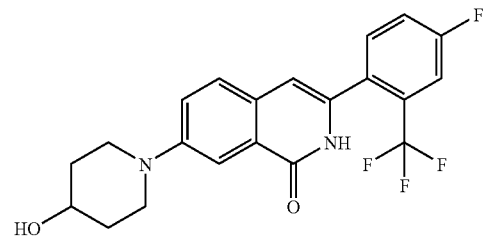

¹H-NMR (400 MHz, CDCl₃) δ (ppm): 1.40-1.50 (1H, m), 1.68-1.76 (2H, m), 2.02-2.09 (2H, m), 3.04-3.17 (2H, m), 3.70-3.79 (2H, m), 3.87-3.98 (1H, m), 6.42 (1H, s), 7.27-7.40 (2H, m), 7.43-7.57 (3H, m), 7.81 (1H, s), 8.31 (1H, brs)
ESI (LC-MS positive mode) m/z 407 (M+H).

Example 97

7-(4-Hydroxypiperidin-1-yl)-3-(2-morpholin-4-ylphenyl)-2H-isoquinolin-1-one

Step A

7-Chloro-3-(2-morpholin-4-ylphenyl)-2H-isoquinolin-1-one

[Formula 119]

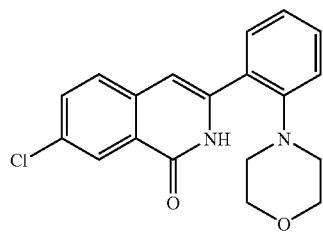

5.39 ml (9.69 mmol) of a 1.8 M lithium diisopropylamide THF solution was diluted with 10 ml of THF. Thereafter, 5 ml of a THF solution containing 383 mg (1.94 mmol) of the 5-chloro-2,N,N-trimethylbenzamide prepared in Step A of Example 80 was added dropwise to the diluted solution at −78° C. Thereafter, 5 ml of a THF solution containing 438 mg (2.33 mmol) of 2-(4-morpholino)benzonitrile was further added to the above mixture, and the obtained mixture was then stirred at −78° C. for 30 minutes. Thereafter, a saturated ammonium chloride aqueous solution was added to the reaction solution, and the mixture was then extracted with ethyl acetate. The extract was washed with a saturated saline solution, and was then dried over anhydrous sodium sulfate. The resultant was concentrated under reduced pressure. The obtained yellow oily product was crystallized from hexane/ethyl acetate (3:1), so as to obtain 575 mg (87%) of 7-chloro-3-(2-morpholin-4-ylphenyl)-2H-isoquinolin-1-one in the form of a colorless crystal.

$^1$H-NMR (400 MHz, CDCl$_3$) δ (ppm): 2.97-3.00 (4H, m), 3.87-3.90 (4H, m), 6.71 (1H, s), 7.19 (2H, m), 7.43 (1H, dt, J=1.2, 7.6 Hz), 7.53 (1H, d, J=8.4 Hz), 7.59-7.62 (2H, m), 8.39 (1H, s), 11.10 (1H, brs)

ESI (LC-MS positive mode) m/z 341 (M+H).

Step B

7-(4-Hydroxypiperidin-1-yl)-3-(2-morpholin-4-ylphenyl)-2H-isoquinolin-1-one

[Formula 120]

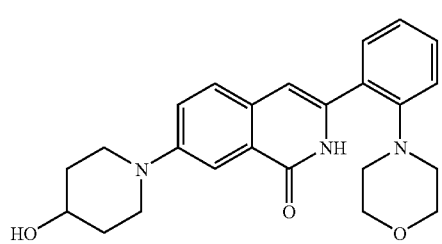

The above compound was synthesized by a method similar to that of Example 20, using the 7-chloro-3-(2-morpholin-4-ylphenyl)-2H-isoquinolin-1-one obtained in Step A as a starting material.

$^1$H-NMR (400 MHz, CDCl$_3$) δ (ppm): 1.48 (1H, d, J=4.4 Hz), 1.70-1.77 (2H, m), 2.03-2.07 (2H, m), 2.96-3.02 (4H, m), 3.04-3.13 (2H, m), 3.71-3.78 (2H, m), 3.86-3.94 (5H, m), 6.67 (1H, s), 7.12-7.21 (2H, m), 7.32-7.42 (2H, m), 7.50 (1H, d, J=8.8 Hz), 7.58 (1H, dd, J=1.4, 8.0 Hz), 7.82 (1H, d, J=3.2 Hz), 10.84 (1H, brs)

ESI (LC-MS positive mode) m/z 406 (M+H).

The following compounds (Examples 98 to 101) were synthesized by a method similar to that of Example 97, using the 5-chloro-2,N,N-trimethylbenzamide prepared in Step A of Example 80 as a starting material.

Example 98

3-Biphenyl-2-yl-7-(3-hydroxypiperidin-1-yl)-2H-isoquinolin-1-one

[Formula 121]

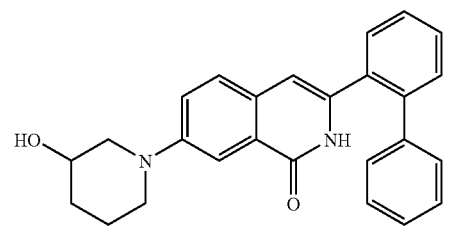

$^1$H-NMR (270 MHz, CDCl$_3$) δ (ppm): 1.57-1.76 (2H, m), 1.82-1.99 (2H, m), 2.12-2.22 (1H, m), 3.11-3.29 (3H, m), 3.46 (1H, dd, J=12.0, 3.0 Hz), 3.90-4.00 (1H, m), 6.42 (1H, s), 7.28-7.57 (11H, m), 7.72 (1H, d, J=2.5 Hz), 8.07 (1H, brs)

ESI (LC-MS positive mode) m/z 397 (M+H).

Example 99

3-(2-Ethylphenyl)-7-(3-hydroxypiperidin-1-yl)-2H-isoquinolin-1-one

[Formula 122]

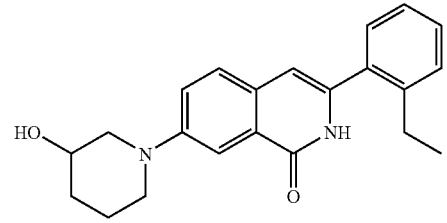

$^1$H-NMR (270 MHz, CDCl$_3$) δ (ppm): 1.18 (3H, t, J=7.5 Hz), 1.65-1.79 (2H, m), 1.84-2.00 (2H, m), 2.15 (1H, d, J=7.0 Hz), 2.71 (2H, q, J=7.5 Hz), 3.16-3.33 (3H, m), 3.49 (1H, dd, J=12.0, 3.0 Hz), 3.94-4.03 (1H, m), 6.40 (1H, s), 7.24-7.43 (5H, m), 7.47 (1H, d, J=8.5 Hz), 7.85 (1H, d, J=2.5 Hz), 8.31 (1H, brs)

ESI (LC-MS positive mode) m/z 349 (M+H).

Example 100

7-(4-Hydroxypiperidin-1-yl)-3-[2-(2-methoxy-ethoxy)phenyl]-2H-isoquinolin-1-one It is to be noted that 2-(2-methoxyethoxy)benzonitrile used in a coupling reaction was prepared from cyanobenzyl bromide and morpholine in accordance with known methods described in publications (for example, WO2003/048164, etc.).

[Formula 123]

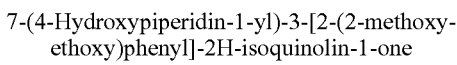

$^1$H-NMR (270 MHz, CDCl$_3$) δ (ppm): 1.73-1.78 (2H, m), 2.01-2.08 (2H, m), 3.01-3.11 (2H, m), 3.57 (3H, s), 3.71-3.77 (2H, m), 3.79-3.82 (2H, m), 3.85-3.93 (1H, m), 4.28-4.32 (2H, m), 6.65 (1H, s), 6.99-7.10 (2H, m), 7.31-7.40 (2H, m), 7.49 (1H, d, J=8.58 Hz), 7.55-7.59 (1H, m), 7.83 (1H, d, J=2.64 Hz) 10.1 (1H, brs)

ESI (LC-MS positive mode) m/z 395 (M+H).

Example 101 t-Butyl 4-{2-[7-(3-hydroxypiperidin-1-yl)-1-oxo-1,2-dihydroisoquinolin-3-yl]phenyl}piperazin-1-carboxylate It is to be noted that 2-(4-t-butoxycarbonyl)piperazin-1-ylbenzonitrile used in a coupling reaction was prepared from cyanobenzyl bromide and morpholine in accordance with known methods described in publications (for example, WO2003/048164, etc.).

[Formula 124]

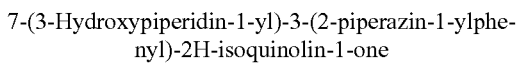

$^1$H-NMR (270 MHz, CDCl$_3$) δ (ppm): 1.44 (9H, s), 1.60-1.78 (2H, m), 1.86-2.01 (2H, m), 2.24-2.34 (1H, m), 2.87-2.98 (4H, m), 3.14-3.35 (3H, m), 3.52 (1H, dd, J=12.0, 3.0 Hz), 3.55-3.64 (4H, m), 3.91-4.01 (1H, m), 6.68 (1H, s), 7.11 (1H, d, J=8.0 Hz), 7.17 (1H, t, J=8.0 Hz), 7.34-7.40 (2H, m), 7.50 (1H, d, J=9.0 Hz), 7.58 (1H, dd, J=8.0, 1.5 Hz), 7.83 (1H, d, J=2.5 Hz), 10.84 (1H, brs)

ESI (LC-MS positive mode) m/z 505 (M+H).

Example 102

7-(3-Hydroxypiperidin-1-yl)-3-(2-piperazin-1-ylphenyl)-2H-isoquinolin-1-one

[Formula 125]

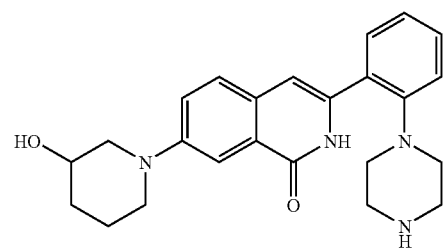

Trifluoroacetic acid (0.2 ml) was added to a dichloromethane solution (0.3 ml) containing 11.5 mg (0.0227 mmol) of t-butyl 4-{2-[7-(3-hydroxypiperidin-1-yl)-1-oxo-1,2-dihydroisoquinolin-3-yl]phenyl}piperazin-1-carboxylate obtained in Example 101. The obtained mixture was stirred at a room temperature for 30 minutes. Thereafter, the solvent was distilled away under reduced pressure. The obtained residue was purified using BondElute NH2 (register trade mark; Varian; 1 g; dichloromethane:methanol=20:1), so as to obtain 8.9 mg (97%) of 7-(3-hydroxypiperidin-1-yl)-3-(2-piperazin-1-ylphenyl)-2H-isoquinolin-1-one in the form of a yellow solid.

$^1$H-NMR (270 MHz, CDCl$_3$) δ (ppm): 1.64-2.02 (5H, m), 2.95-2.99 (4H, m), 3.05-3.08 (4H, m), 3.15-3.34 (3H, m), 3.51 (1H, dd, J=12.0, 3.0 Hz), 3.94-4.01 (1H, m), 6.69 (1H, d, J=1.5 Hz), 7.13-7.18 (2H, m), 7.34-7.40 (2H, m), 7.51 (1H, d, J=8.5 Hz), 7.59 (1H, dd, J=8.0, 1.5 Hz), 7.84 (1H, d, J=2.5 Hz), 11.18 (1H, brs)

ESI (LC-MS positive mode) m/z 405 (M+H).

Example 103

7-(3-Hydroxypiperidin-1-yl)-3-[2-(4-methylpiperazin-1-yl)phenyl]-2H-isoquinolin-1-one

[Formula 126]

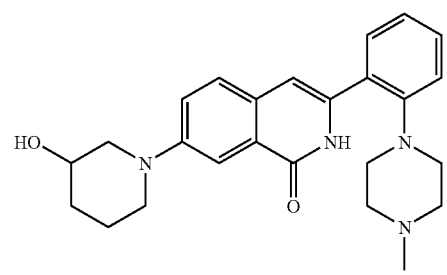

0.0185 ml (0.133 mmol) of triethylamine and 0.00665 ml (0.107 mmol) of iodomethane were added to an acetonitrile solution (0.4 ml) containing 3.6 mg (0.0089 mmol) of the 7-(3-hydroxypiperidin-1-yl)-3-(2-piperazin-1-ylphenyl)-2H-isoquinolin-1-one obtained in Example 102. The obtained mixture was stirred at a room temperature for 4 hours. Thereafter, the solvent was distilled away under reduced pressure. The obtained residue was developed and purified by thin-layer chromatography (NH$_2$ F254s, Merck, developing solvent; dichloromethane:methanol=10:1, Rf value: 0.8), so as to obtain 1.8 mg (48%) of 7-(3-hydroxypiperidin-1-yl)-3-[2-(4-methylpiperazin-1-yl)phenyl]-2H-isoquinolin-1-one in the form of a yellow solid.

$^1$H-NMR (270 MHz, CD$_3$OD) δ (ppm): 1.41-1.55 (1H, m), 1.64-1.77 (1H, m), 1.90-2.07 (2H, m), 2.38 (3H, s), 2.48-2.66 (4H, m), 2.83 (1H, dd, J=12.0, 8.0 Hz), 2.90-3.03 (5H, m), 3.56-3.64 (1H, m), 3.73-3.87 (2H, m), 6.87 (1H, s), 7.17 (1H, ddd, J=8.0, 8.0, 1.5 Hz), 7.22 (1H, dd, J=8.0, 1.5 Hz), 7.40 (1H, ddd, J=8.0, 8.0, 1.5 Hz), 7.50 (1H, dd, J=9.0, 3.0 Hz), 7.58 (1H, dd, J=8.0, 1.5 Hz), 7.63 (1H, d, J=9.0 Hz), 7.71 (1H, d, J=3.0 Hz)

ESI (LC-MS positive mode) m/z 419 (M+H).

Example 104

7-Thiomorpholin-4-yl-3-(2-trifluoromethylphenyl)-2H-isoquinolin-1-one

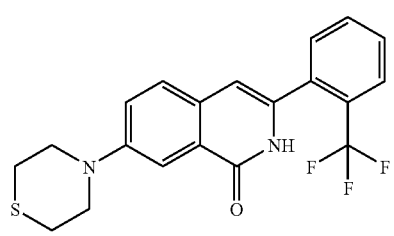

[Formula 127]

The above compound was synthesized by a method similar to that of Example 4, using the 7-chloro-3-(2-trifluoromethylphenyl)-2H-isoquinolin-1-one obtained in Step B of Example 1 as a starting material.

$^1$H-NMR (270 MHz, CDCl$_3$) δ (ppm): 2.70-2.85 (4H, m), 3.65-3.83 (4H, m), 6.46 (1H, s), 7.32 (1H, dd, J=2.6, 8.9 Hz), 7.45-7.70 (4H, m), 7.75 (1H, d, J=2.6 Hz), 7.81 (1H, d, J=7.3 Hz), 8.93 (1H, brs)

ESI (LC-MS positive mode) m/z 391 (M+H).

Example 105

7-(1-Oxothiomorpholin-4-yl)-3-(2-trifluoromethylphenyl)-2H-isoquinolin-1-one

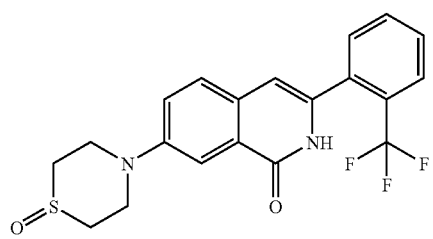

[Formula 128]

20.1 mg (0.0515 mmol) of the 7-thiomorpholin-4-yl-3-(2-trifluoromethylphenyl)-2H-isoquinolin-1-one obtained in Example 104 was dissolved in 2.3 ml of methylene chloride, and 9.8 mg (0.0566 mmol) of m-chloroperbenzoic acid was further added to the solution. The obtained mixture was stirred at 0° C. for 2 hours. Thereafter, a saturated sodium bicarbonate aqueous solution was added to the reaction solution, and the obtained mixture was then extracted with methylene chloride. The extract was dried over anhydrous sodium sulfate, and was then concentrated. The obtained residue was purified by silica gel column chromatography (methylene chloride:methanol=20:1), so as to obtain 16.6 mg (79%) of 7-(1-oxothiomorpholin-4-yl)-3-(2-trifluoromethylphenyl)-2H-isoquinolin-1-one in the form of a light yellow solid.

$^1$H-NMR (270 MHz, CDCl$_3$) δ (ppm): 2.80-3.00 (4H, m), 3.80 (2H, dt, J=14.9, 3.8 Hz), 4.16 (2H, ddd, J=3.8, 9.2, 13.9 Hz), 6.47 (1H, s), 7.37 (1H, dd, J=2.6, 8.9 Hz), 7.50-7.70 (4H, m), 7.77-7.85 (2H, m), 8.81 (1H, brs)

ESI (LC-MS positive mode) m/z 407 (M+H).

The following compounds (Examples 106 and 107) were synthesized by a method similar to that of Example 20, using the 7-chloro-3-(2-trifluoromethylphenyl)-2H-isoquinolin-1-one obtained in Step B of Example 1 as a starting material.

Example 106

7-((R)-3-Hydroxypiperidin-1-yl)-3-(2-trifluoromethylphenyl)-2H-isoquinolin-1-one

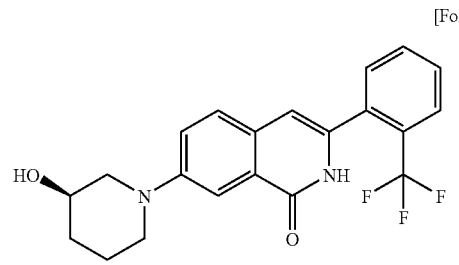

[Formula 129]

$^1$H-NMR (270 MHz, CDCl$_3$) δ (ppm): 1.58-1.80 (2H, m), 1.82-2.00 (2H, m), 2.18 (1H, d, J=6.9 Hz), 3.13-3.38 (3H, m), 3.51 (1H, dd, J=3.0, 12.2 Hz), 3.91-4.02 (1H, m), 6.45 (1H, s), 7.39 (1H, dd, J=2.3, 8.9 Hz), 7.43-7.70 (4H, m), 7.77-7.86 (2H, m), 8.50 (1H, brs)

ESI (LC-MS positive mode) m/z 389 (M+H).

Example 107

7-((S)-3-Hydroxypiperidin-1-yl)-3-(2-trifluoromethylphenyl)-2H-isoquinolin-1-one

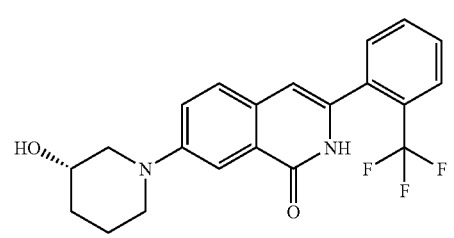

[Formula 130]

¹H-NMR (270 MHz, CDCl₃) δ (ppm): 1.60-1.80 (2H, m), 1.82-2.03 (2H, m), 2.32 (1H, d, J=6.6 Hz), 3.13-3.38 (3H, m), 3.52 (1H, dd, J=3.1, 12.0 Hz), 3.91-4.02 (1H, m), 6.45 (1H, s), 7.38 (1H, dd, J=2.6, 8.9 Hz), 7.44-7.70 (4H, m), 7.77-7.85 (2H, m), 8.69 (1H, brs)

ESI (LC-MS positive mode) m/z 389 (M+H).

The following compounds (Examples 108 to 111) were synthesized by a method similar to that in Step B of Example 1, using the 2,N,N-trimethyl-5-morpholin-4-ylbenzamide prepared in Step B of Example 80 as a starting material.

Example 108

7-Morpholin-4-yl-3-o-tolyl-2H-isoquinolin-1-one

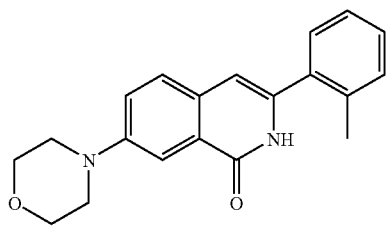

[Formula 131]

¹H-NMR (400 MHz, CDCl₃) δ (ppm): 2.41 (3H, s), 3.30 (4H, t, J=4.9 Hz), 3.91 (4H, t, J=4.9 Hz), 6.42. (1H, s), 7.28-7.37 (5H, m), 7.50 (1H, d, J=8.8 Hz), 7.81 (1H, d, J=2.9 Hz), 8.37 (1H, brs)

ESI (LC-MS positive mode) m/z 321 (M+H).

Example 109

7-Morpholin-4-yl-3-naphthalen-2-yl-2H-isoquinolin-1-one

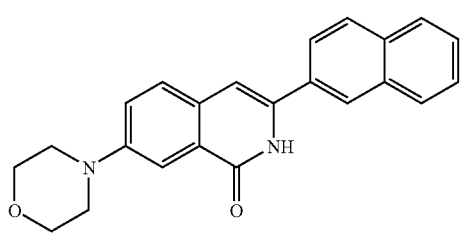

[Formula 132]

¹H-NMR (400 MHz, CDCl₃) δ (ppm): 3.33 (4H, t, J=4.9 Hz), 3.91 (4H, t, J=4.9 Hz), 6.87 (1H, s), 7.37 (1H, dd, J=2.4, 8.8 Hz), 7.50-7.60 (3H, m), 7.74 (1H, dd, J=1.7, 8.5 Hz), 7.82 (1H, d, J=2.9 Hz), 7.85-7.93 (2H, m), 7.96 (1H, d, J=8.8 Hz), 8.06 (1H, s), 8.80 (1H, brs)

ESI (LC-MS positive mode) m/z 357 (M+H).

Example 110

3-(2-Dimethylaminophenyl)-7-morpholin-4-yl-2H-isoquinolin-1-one

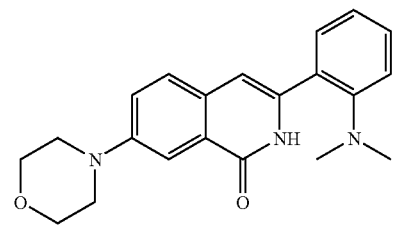

[Formula 133]

2-(N,N-dimethylamino)benzonitrile used in the reaction was prepared in accordance with known methods described in publications (for example, J. Org. Chem., Vol. 48, 2933-2935 (1983), etc.).

¹H-NMR (400 MHz, CDCl₃) δ (ppm): 2.71 (6H, s), 3.31 (4H, t, J=4.8 Hz), 3.91 (4H, t, J=4.8 Hz), 6.70 (1H, s), 7.09-7.25 (2H, m), 7.33-7.37 (2H, m), 7.52-7.57 (2H, m), 7.81 (1H, s), 10.70 (1H, brs)

ESI (LC-MS positive mode) m/z 350 (M+H).

Example 111

7-Morpholin-4-yl-3-(2-pyrrolidin-1-ylphenyl)-2H-isoquinolin-1-one

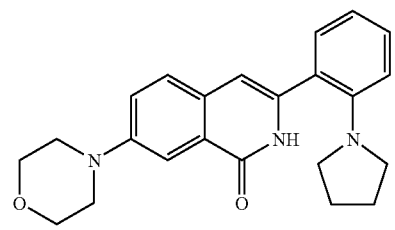

[Formula 134]

2-(1-Pyrrolidinyl)benzonitrile used in the reaction was prepared in accordance with known methods described in publications (for example, US 2002/0193389, etc.).

¹H-NMR (400 MHz, CDCl₃) δ (ppm): 1.85-1.90 (4H, m), 3.04-3.08 (4H, m), 3.30 (4H, t, J=4.8 Hz), 3.90 (4H, t, J=4.8 Hz), 6.61 (1H, s), 6.96-7.02 (2H, m), 7.31-7.53 (4H, m), 7.80 (1H, s), 9.67 (1H, brs)

ESI (LC-MS positive mode) m/z 376 (M+H).

Example 112

7-((S)-2,3-Dihydroxypropylamino)-3-(2-trifluoromethylphenyl)-2H-isoquinolin-1-one

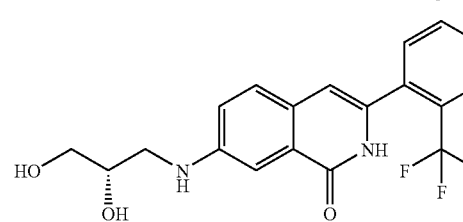

[Formula 135]

132.6 μl (20 mmol) of (R)-glycidol was added to an ethanol solution (10 ml) containing 608.5 mg (2.0 mmol) of the 7-amino-3-(2-trifluoromethylphenyl)-2H-isoquinolin-1-one obtained in Example 38. The obtained mixture was stirred under heating to reflux overnight. The residue obtained by concentration of the reaction solution was purified by silica gel column chromatography (methylene chloride:methanol=20:1), so as to obtain 514.3 mg (68%) of 7-((S)-2,3-dihydroxypropylamino)-3-(2-trifluoromethylphenyl)-2H-isoquinolin-1-one in the form of a light yellow amorphous substance.

$^1$H-NMR (270 MHz, DMSO-$d_6$) δ (ppm): 2.95-3.05 (1H, m), 3.23-3.46 (3H, m), 3.64-3.73 (1H, m), 4.66 (1H, t, J=5.3 Hz), 4.84 (1H, d, J=5.0 Hz), 6.03 (1H, t, J=5.4 Hz), 6.29 (1H, s), 7.13 (1H, dd, J=2.0, 8.8 Hz), 7.24 (1H, d, J=2.0 Hz), 7.40 (1H, d, J=8.8 Hz), 7.58 (1H, d, J=7.5 Hz), 7.66 (1H, t, J=7.5 Hz), 7.75 (1H, t, J=7.5 Hz), 7.84 (1H, d, J=7.5 Hz), 11.24 (1H, brs)

ESI (LC-MS positive mode) m/z 379 (M+H).

Example 113

7-((R)-2,3-Dihydroxypropylamino)-3-(2-trifluoromethylphenyl)-2H-isoquinolin-1-one

[Formula 136]

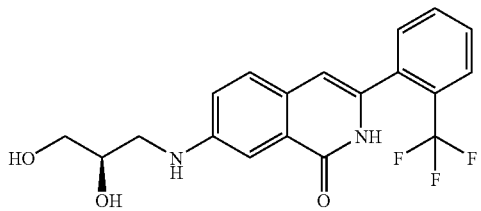

The above compound was synthesized by a method similar to that of Example 112, using the 7-amino-3-(2-trifluoromethylphenyl)-2H-isoquinolin-1-one obtained in Example 38.

$^1$H-NMR (270 MHz, DMSO-$d_6$) δ (ppm): 2.95-3.05 (1H, m), 3.20-3.46 (3H, m), 3.64-3.73 (1H, m), 4.60-4.70 (1H, m), 4.85 (1H, d, J=4.6 Hz), 6.00-6.08 (1H, m), 6.29 (1H, s), 7.13 (1H, dd, J=2.0, 8.3 Hz), 7.24 (1H, s), 7.40 (1H, d, J=8.3 Hz), 7.58 (1H, d, J=7.3 Hz), 7.66 (1H, t, J=7.3 Hz), 7.75 (1H, t, J=7.3 Hz), 7.84 (1H, d, J=7.3 Hz), 11.24 (1H, brs)

ESI (LC-MS positive mode) m/z 379 (M+H).

Example 114

7-Imidazol-1-yl-3-(2-trifluoromethylphenyl)-2H-isoquinolin-1-one

Step A

7-Iodo-3-(2-trifluoromethylphenyl)-2H-isoquinolin-1-one

[Formula 137]

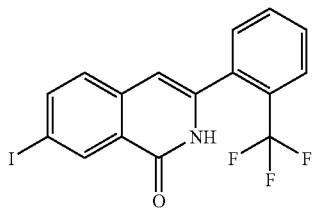

A 1 N sulfuric acid aqueous solution (30 ml) and 862.5 mg (12.5 mmol) of sodium nitrite were added at 0° C. to an acetic acid solution (15 ml) containing 1.52 g (5.0 mmol) of the 7-amino-3-(2-trifluoromethylphenyl)-2H-isoquinolin-1-one obtained in Example 38. The obtained mixture was stirred for 30 minutes. Thereafter, 2.62 g (17.5 mmol) of sodium iodide and 952.3 mg (5.0 mmol) of copper iodide (I) were added to the reaction solution, and the obtained mixture was stirred at 80° C. for 1 hour. Thereafter, the reaction solution was cooled, and a saturated sodium bicarbonate aqueous solution was added thereto, followed by extraction with ethyl acetate. The extract was washed with a saturated saline solution, and was then dried over anhydrous sodium sulfate, followed by concentration. The obtained residue was purified by silica gel column chromatography (ethyl acetate:hexane=1:4 to 1:2), and was then washed with a sodium thiosulfate aqueous solution, so as to obtain 1.87 g (90%) of 7-iodo-3-(2-trifluoromethylphenyl)-2H-isoquinolin-1-one in the form of a light yellow solid.

$^1$H-NMR (270 MHz, CDCl$_3$) δ (ppm): 6.47 (1H, s), 7.31 (1H, d, J=8.6 Hz), 7.55 (1H, dd, J=1.7, 7.3 Hz), 7.59-7.73 (2H, m), 7.83 (1H, dd, J=2.0, 6.9 Hz), 7.96 (1H, dd, J=1.8, 8.4 Hz), 8.72 (1H, d, J=1.6 Hz), 9.06 (1H, brs)

ESI (LC-MS positive mode) m/z 416 (M+H).

Step B

7-Imidazol-1-yl-3-(2-trifluoromethylphenyl)-2H-isoquinolin-1-one

[Formula 138]

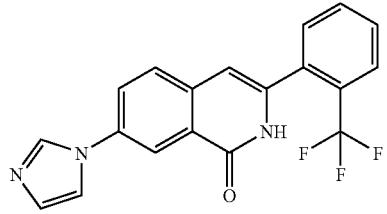

10.4 mg (0.025 mmol) of the 7-iodo-3-(2-trifluoromethylphenyl)-2H-isoquinolin-1-one obtained in Step A, 0.48 mg (0.0025 mmol) of copper iodide (I), 2.0 mg (0.03 mmol) of imidazole, and 11.1 mg (0.0525 mmol) of potassium phosphate were suspended in 0.25 ml of 1,4-dioxane. Then, 2.6 μl of N,N'-dimethylethylenediamine was added to the suspension, and the obtained mixture was then stirred at 110° C. overnight. Thereafter, the reaction solution was cooled to a room temperature, and a saturated ammonium chloride aqueous solution was then added to the reaction solution, followed by extraction with ethyl acetate. The extract was dried over anhydrous sodium sulfate, and was then concentrated. The obtained residue was purified by silica gel column chromatography (methylene chloride:methanol=25:1 to 20:1), so as to obtain 8.3 mg (93%) of 7-imidazol-1-yl-3-(2-trifluoromethylphenyl)-2H-isoquinolin-1-one in the form of a colorless viscous oily substance.

$^1$H-NMR (270 MHz, CDCl$_3$) δ (ppm): 6.58 (1H, s), 7.24 (1H, s), 7.41 (1H, s), 7.55-7.77 (5H, m), 7.84 (1H, dd, J=1.7, 7.6 Hz), 7.98 (1H, s), 8.35 (1H, d, J=2.0 Hz), 9.89 (1H, brs)

ESI (LC-MS positive mode) m/z 356 (M+H).

Example 115

7-[1,2,4]Triazol-1-yl-3-(2-trifluoromethylphenyl)-2H-isoquinolin-1-one

[Formula 139]

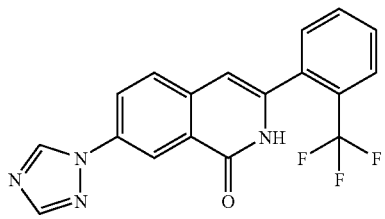

The above compound was synthesized by a method similar to that in Step B of Example 114, using the 7-iodo-3-(2-trifluoromethylphenyl)-2H-isoquinolin-1-one obtained in Step A as a starting material.

$^1$H-NMR (270 MHz, CDCl$_3$) δ (ppm): 6.58 (1H, s), 7.55-7.75 (4H, m), 7.80-7.88 (1H, m), 8.16 (1H, s), 8.17 (1H, dd, J=2.3H, 8.6 Hz), 8.64 (1H, d, J=2.3 Hz), 8.68 (1H, brs), 8.75 (1H, s)

ESI (LC-MS positive mode) m/z 357 (M+H).

Example 116

7-Tetrazol-1-yl-3-(2-trifluoromethylphenyl)-2H-isoquinolin-1-one

[Formula 140]

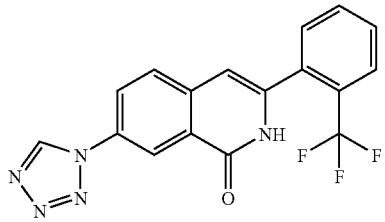

17.5 μl (0.16 mmol) of trimethyl orthoformate and 9.8 mg (0.15 mmol) of sodium azide were added to 0.2 ml of an acetic acid solution containing the 7-amino-3-(2-trifluoromethylphenyl)-2H-isoquinolin-1-one obtained in Example 38. The obtained mixture was stirred at 80° C. for 6 hours. Thereafter, the reaction solution was cooled to a room temperature, and water was then added to thereto, followed by extraction with ethyl acetate. The extract was washed with a saturated sodium bicarbonate aqueous solution, and was then dried over anhydrous sodium sulfate, followed by concentration. The obtained residue was purified by silica gel column chromatography (ethyl acetate:hexane=2:1), so as to obtain 29.8 mg (83%) of 7-tetrazol-1-yl-3-(2-trifluoromethylphenyl)-2H-isoquinolin-1-one in the form of a colorless solid.

$^1$H-NMR (270 MHz, CDCl$_3$) δ (ppm): 6.62 (1H, s), 7.57-7.90 (5H, m), 8.19 (1H, dd, J=2.3, 8.6 Hz), 8.61 (1H, d, J=2.3 Hz), 9.24 (1H, s), 9.71 (1H, brs)

ESI (LC-MS positive mode) m/z 358 (M+H).

Example 117

7-((R)-3-Benzyloxy-2-methylaminopropylamino)-3-(2-trifluoromethylphenyl)-2H-isoquinolin-1-one; and

Example 118

7-((R)-4-Benzyloxymethyl-3-methylimidazolidin-1-yl)-3-(2-trifluoromethylphenyl)-2H-isoquinolin-1-one

[Formula 141]

Chiral

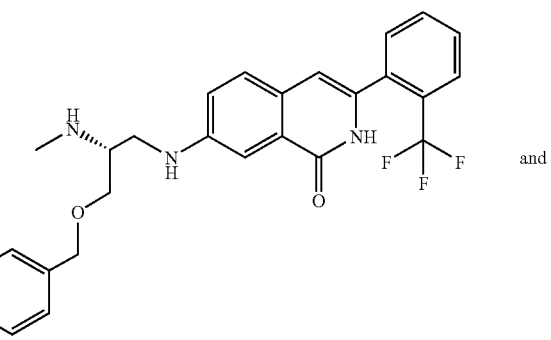

and

Chiral

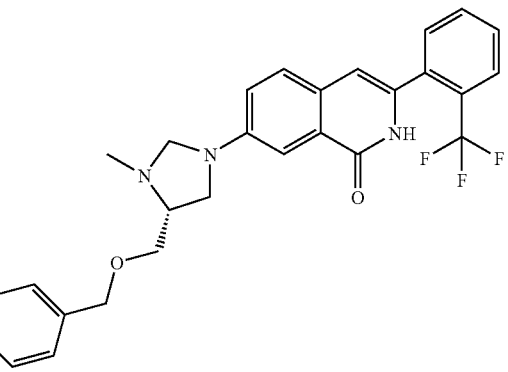

1.2 g (2.8 mmol) of a BOP reagent, 0.5 ml (3 mmol) of N,N-diisopropylethylamine, and 273 mg (2.8 mmol) of N,O-dimethylhydroxylamine hydrochloride were added to a dichloromethane solution containing 1 g (2.3 mmol) of Fmoc-Meser(Bzl)—OH. The obtained mixture was stirred at a room temperature over a day and a night. Thereafter, the reaction solution was successively washed with 1 N hydrochloric acid, a saturated sodium bicarbonate aqueous solution, and a saturated saline solution. The resultant was dried over anhydrous sodium sulfate, and the solvent was then distilled away under reduced pressure. The obtained residue was purified by silica gel column chromatography (ethyl acetate:hexane=1:2). 238 mg out of 850 mg of the obtained oily product was added to 2 ml of a THF solution, and the obtained solution was then added dropwise to 8 ml of a THF solution containing 10 mg (0.25 mmol) of aluminum lithium hydride at −78° C. The obtained mixture was stirred at −78° C. for 1.5 hours. Thereafter, 10 mg (0.25 mmol) of aluminum lithium hydride was further added to the reaction solution, and the obtained mixture was then stirred at −78° C. for 30 minutes. Thereafter, a saturated ammonium chloride aqueous solution was added to the reaction solution at −78° C., and the temperature of the mixture was increased to a room temperature. Thereafter, the mixture was filtrated with celite, and the filtrate was then extracted with dichloromethane. The extract was washed with a saturated saline solution, and was dried over anhydrous sodium sulfate, followed by concentration under reduced pressure. The generated oil product was dissolved in 5 ml of methanol without being purified. Thereafter, 100 mg (0.33 mmol) of 7-amino-3-(2-trifluoromethylphenyl)-2H-isoquinolin-1-one and 1 ml of acetic acid were added thereto. Thereafter, 135 mg (2.1 mmol) of sodium cyanoborohydride was added to the mixture under cooling on ice, and the temperature of the obtained mixture was increased to a room temperature, followed by stirring for 3 hours. Thereafter, a saturated sodium bicarbonate aqueous solution was added to the reaction solution, and the mixture was then extracted with dichloromethane. The extract was dried over anhydrous sodium sulfate, and was then concentrated. The obtained residue was purified by silica gel column chromatography (ethyl acetate:hexane=1:2 to 2:1), so as to obtain a yellow foaming substance. This yellow foaming substance was dissolved in 5 ml of dichloromethane, and 1 ml of piperidine was then added to the solution. The obtained mixture was stirred at a room temperature. Four hours later, the reaction solution was concentrated, and 2 ml of 1 N hydrochloric acid and 2 ml of methanol were then added thereto, followed by stirring at 40° C. Six hours later, the reaction solution was neutralized with a 1 N sodium hydroxide aqueous solution under cooling on ice. A saturated sodium bicarbonate aqueous solution was added to the resultant, and the mixture was then extracted with dichloromethane. The extract was dried over anhydrous sodium sulfate, and was then concentrated. The obtained residue was purified by amino TLC used for preparative separation (Fuji Silysia Chemical Ltd., PLC05; dichloromethane:methanol=20:1), so as to obtain 48 mg (31%) of 7-((R)-3-benzyloxy-2-methylaminopropylamino)-3-(2-trifluoromethylphenyl)-2H-isoquinolin-1-one in the form of a yellow foaming substance, as well as 28 mg (17%) of 7-((R)-4-benzyloxymethyl-3-methylimidazolidin-1-yl)-3-(2-trifluoromethylphenyl)-2H-isoquinolin-1-one in the form of a yellow foaming substance.

7-((R)-3-benzyloxy-2-methylaminopropylamino)-3-(2-trifluoromethylphenyl)-2H-isoquinolin-1-one (Example 117)

$^1$H-NMR (270 MHz, CDCl$_3$) δ (ppm): 2.43 (3H, s), 2.99-3.04 (1H, m), 3.18-3.27 (1H, m), 3.34-3.42 (1H, m), 3.54-3.66 (2H, m), 4.55 (2H, s), 4.73 (1H, brt), 6.42 (1H, s), 7.01 (1H, dd, J=2.31, 8.24 Hz), 7.31-7.39 (6H, m), 7.48 (1H, d, J=2.47 Hz), 7.52-7.67 (3H, m), 7.80 (1H, d, J=6.76 Hz)
ESI (LC-MS positive mode) m/z 482 (M+H).

7-((R)-4-benzyloxymethyl-3-methylimidazolidin-1-yl)-3-(2-trifluoromethylphenyl)-2H-isoquinolin-1-one (Example 118)

$^1$H-NMR (270 MHz, CDCl$_3$) δ (ppm): 2.53 (3H, s), 3.05-3.10 (1H, m), 3.38-3.44 (1H, m), 3.57 (1H, dd, J=5.44, 9.73 Hz), 3.63-3.71 (2H, m), 3.86 (1H, d, J=4.78 Hz), 4.57 (1H, d, J=4.78 Hz), 4.60 (2H, s), 6.44 (1H, s), 6.91-6.95 (1H, m), 7.27-7.37 (5H, m), 7.43 (1H, d, J=8.90 Hz), 7.47-7.67 (3H, m), 7.80 (1H, d, J=7.42 Hz), 8.30 (1H, s)
ESI (LC-MS positive mode) m/z 494 (M+H).

Example 119

7-Methylamino-3-(2-trifluoromethylphenyl)-2H-isoquinolin-1-one

Step A

7-Bromo-3-(2-trifluoromethylphenyl)-2H-isoquinolin-1-one

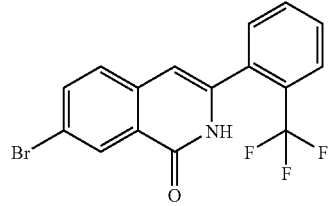

[Formula 142]

5-Bromo-2,N-dimethylbenzamide was prepared by a method similar to that in Step A of Example 1 from 2-bromo-5-methylbenzoic acid that can be prepared by the method disclosed in WO2002/083066 or U.S. Pat. No. 4,282,365. Using this compound as a starting material, 7-bromo-3-(2-trifluoromethylphenyl)-2H-isoquinolin-1-one was synthesized by a method similar to that in Step B of Example 1.
$^1$H-NMR (270 MHz, CDCl$_3$) δ (ppm): 6.48 (1H, s), 7.45 (1H, d, J=8.58 Hz), 7.53-7.56 (1H, m), 7.61-7.72 (2H, m), 7.76-7.84 (2H, m), 8.53 (1H, d, J=1.98 Hz), 8.87 (1H, brs)
ESI (LC-MS positive mode) m/z 368 (M+H), 370 (M+H+2).

Step B

7-Methylamino-3-(2-trifluoromethylphenyl)-2H-isoquinolin-1-one

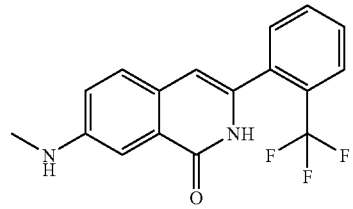

[Formula 143]

30 mg (0.08 mmol) of the 7-bromo-3-(2-trifluoromethylphenyl)-2H-isoquinolin-1-one prepared in Step A, 18.6 mg (0.098 mmol) of copper iodide (I), and 39.1 mg (0.204 mmol) of cesium acetate were suspended in 0.5 ml of dry dimethylformamide. Thereafter, 200 μl of a 40% methylamine-methanol solution was added to the suspension, and the obtained mixture was then stirred at 100° C. overnight. Thereafter, water was added to the reaction solution, and the mixture was then extracted with methylene chloride. The extract was washed with a saturated saline solution, and was then dried over anhydrous magnesium sulfate. The extract was concentrated. The obtained residue was purified by silica gel column chromatography (methylene chloride:methanol=100:1), so as to obtain 15.4 mg (61%) of 7-methylamino-3-(2-trifluoromethylphenyl)-2H-isoquinolin-1-one.
$^1$H-NMR (270 MHz, CDCl$_3$) δ (ppm): 1.25 (1H, s), 2.98 (3H, s), 6.44 (1H, s), 7.02 (1H, dd, J=2.6, 8.6 Hz), 7.40 (1H, d, J=8.6 Hz), 7.50-7.65 (4H, m), 7.80 (1H, d, J=7.9 Hz), 8.29 (1H, m)
ESI (LC-MS positive mode) m/z 319 (M+H).

The following compounds (Examples 120 to 130) were synthesized by a method similar to that of Example 57, using the 7-amino-3-(2-trifluoromethylphenyl)-2H-isoquinolin-1-one obtained in Example 38 as a starting material.

Example 120

Propyl[1-oxo-3-(2-trifluoromethylphenyl)-1,2-dihydroisoquinolin-7-yl]carbamate

[Formula 144]

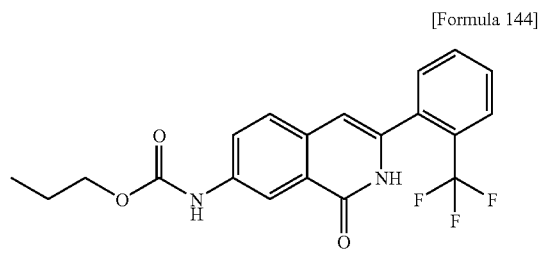

$^1$H-NMR (400 MHz, CDCl$_3$) δ (ppm): 1.00 (3H, t, J=7.2 Hz), 1.58-1.78 (2H, m), 4.17 (2H, t, J=6.8 Hz), 6.48 (1H, s), 6.96-7.00 (1H, m), 7.54-7.69 (4H, m), 7.82 (1H, d, J=7.2 Hz), 8.05-8.30 (2H, m), 8.56 (1H, brs)
ESI (LC-MS positive mode) m/z 391 (M+H).

Example 121

Isopropyl[1-oxo-3-(2-trifluoromethylphenyl)-1,2-dihydroisoquinolin-7-yl]carbamate

[Formula 145]

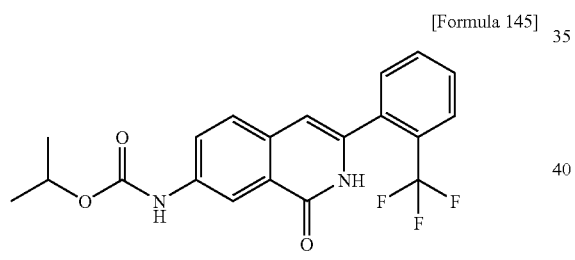

$^1$H-NMR (400 MHz, CDCl$_3$) δ (ppm): 1.34 (3H, d, J=6.4 Hz), 1.37 (3H, d, J=6.4 Hz), 5.03-5.09 (1H, m), 6.48 (1H, s), 6.75-6.85 (1H, m), 7.52-7.69 (4H, m), 7.82 (1H, d, J=8.0 Hz), 8.09 (1H, d, J=2.4 Hz), 8.12 (1H, brs), 8.41 (1H, brs)
ESI (LC-MS positive mode) m/z 391 (M+H).

Example 122

Isobutyl[1-oxo-3-(2-trifluoromethylphenyl)-1,2-dihydroisoquinolin-7-yl]carbamate

[Formula 146]

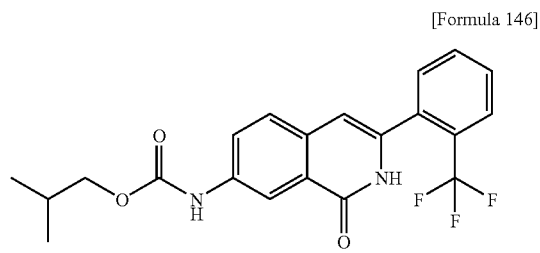

$^1$H-NMR (270 MHz, CDCl$_3$) δ (ppm): 0.99 (6H, d, J=6.6 Hz), 1.95-2.06 (1H, m), 4.00 (2H, d, J=6.6 Hz), 6.49 (1H, s), 6.93-7.02 (1H, m), 7.55-7.70 (4H, m), 7.82 (1H, d, J=7.3 Hz), 8.09-8.20 (2H, m), 8.53 (1H, brs)
ESI (LC-MS positive mode) m/z 405 (M+H).

Example 123

Pentyl[1-oxo-3-(2-trifluoromethylphenyl)-1,2-dihydroisoquinolin-7-yl]carbamate

[Formula 147]

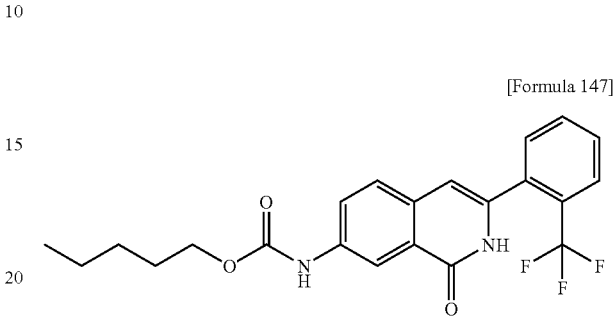

$^1$H-NMR (270 MHz, CDCl$_3$) δ (ppm): 0.92 (3H, t, J=6.60 Hz), 1.35-1.38 (4H, m), 1.65-1.72 (2H, m), 4.19 (2H, t, J=6.60 Hz), 6.49 (1H, s), 7.11 (1H, s), 7.56 (2H, d, J=8.58 Hz), 7.60-7.70 (2H, m), 7.82 (1H, d, J=7.92 Hz), 8.11-8.16 (2H, m), 8.80 (1H, brs)
EI-MS m/z 418 (M$^+$).

Example 124

Benzyl[1-oxo-3-(2-trifluoromethylphenyl)-1,2-dihydroisoquinolin-7-yl]carbamate

[Formula 148]

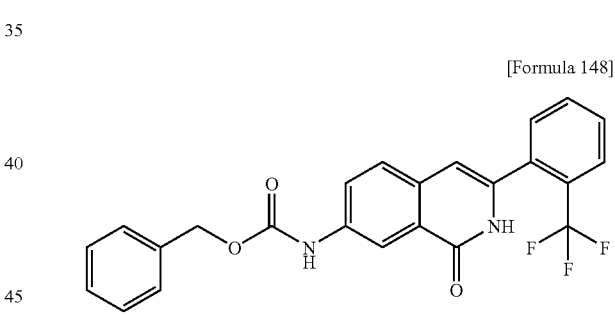

$^1$H-NMR (270 MHz, CDCl$_3$) δ (ppm): 5.23 (2H, s), 6.49 (1H, s), 7.31-7.43 (6H, m), 7.52-7.69 (4H, m), 7.81 (1H, d, J=7.26 Hz), 8.10-8.20 (2H, m), 8.82 (1H, brs)
EI-MS m/z 438 (M$^+$).

Example 125

Allyl[1-oxo-3-(2-trifluoromethylphenyl)-1,2-dihydroisoquinolin-7-yl]carbamate

[Formula 149]

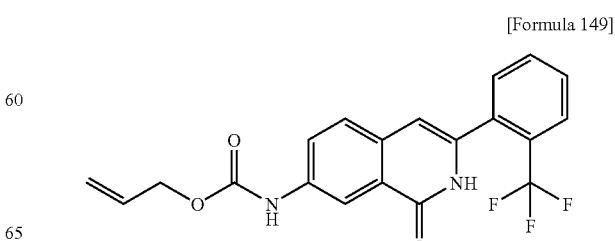

¹H-NMR (400 MHz, CDCl₃) δ (ppm): 4.70-4.73 (2H, m), 5.29 (1H, d, J=10.4 Hz), 5.39 (1H, d, J=16.0 Hz), 5.95-6.05 (1H, m), 6.49 (1H, s), 6.97-7.01 (1H, m), 7.54-7.69 (4H, m), 7.82 (1H, d, J=8.0 Hz), 8.05-8.20 (2H, m), 8.43 (1H, brs)
ESI (LC-MS positive mode) m/z 389 (M+H).

Example 126

But-2-ynyl[1-oxo-3-(2-trifluoromethylphenyl)-1,2-dihydroisoquinolin-7-yl]carbamate

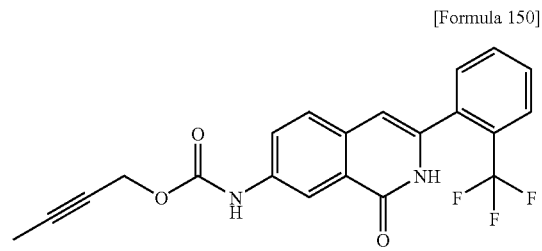

[Formula 150]

¹H-NMR (270 MHz, DMSO-d₆) δ (ppm): 1.86 (3H, s), 4.77 (2H, s), 6.43 (1H, s), 7.62-7.81 (5H, m), 7.87 (1H, d, J=7.9 Hz), 8.37 (1H, s), 10.14 (1H, s), 11.53 (1H, brs)
ESI (LC-MS positive mode) m/z 401 (M+H).

Example 127

2-(2-Methoxyethoxy)ethyl[1-oxo-3-(2-trifluoromethylphenyl)-1,2-dihydroisoquinolin-7-yl]carbamate

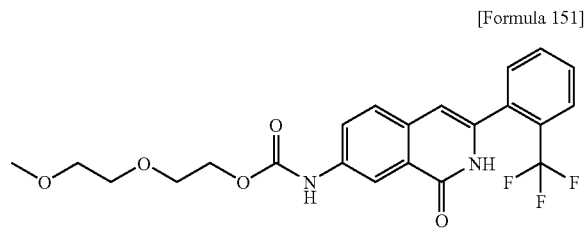

[Formula 151]

¹H-NMR (270 MHz, CDCl₃) δ (ppm): 3.38 (3H, s), 3.55-3.58 (2H, m), 3.66-3.69 (2H, m), 3.76-3.79 (2H, m), 4.36-4.39 (2H, m), 6.49 (1H, s), 7.33 (1H, s), 7.55 (2H, d, J=8.57 Hz), 7.60-7.70 (2H, m), 7.81 (1H, d, J=7.25 Hz), 8.12 (1H, brs), 8.14 (1H, s), 8.78 (1H, brs)
EI-MS m/z 450 (M⁺).

Example 128

3-Methoxy-2,2-dimethylpropyl[1-oxo-3-(2-trifluoromethylphenyl)-1,2-dihydroisoquinolin-7-yl]carbamate

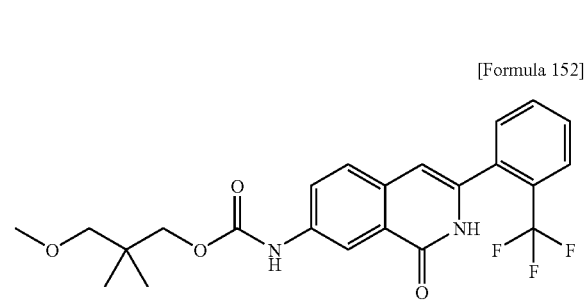

[Formula 152]

¹H-NMR (400 MHz, CDCl₃) δ (ppm): 0.98 (6H, s), 3.19 (2H, s), 3.33 (3H, s), 4.04 (2H, s), 6.49 (1H, s), 7.10-7.20 (1H, m), 7.55-7.69 (4H, m), 7.82 (1H, d, J=7.2 Hz), 8.10-8.20 (2H, m), 8.61 (1H, brs)
ESI (LC-MS positive mode) m/z 449 (M+H).

Example 129

2-Methoxyethyl[1-oxo-3-(2-trifluoromethylphenyl)-1,2-dihydroisoquinolin-7-yl]carbamate

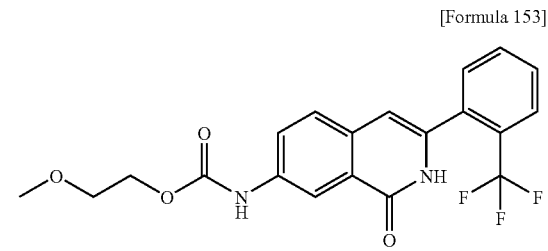

[Formula 153]

¹H-NMR (270 MHz, DMSO-d₆) δ (ppm): 3.30 (3H, s), 3.59 (2H, t, J=4.6 Hz), 4.25 (2H, t, J=4.6 Hz), 6.42 (1H, s), 7.60-7.88 (6H, m), 8.40 (1H, s), 10.10 (1H, s), 11.51 (1H, s)
ESI (LC-MS positive mode) m/z 407 (M+H).

Example 130

2-Benzyloxyethyl[1-oxo-3-(2-trifluoromethylphenyl)-1,2-dihydroisoquinolin-7-yl]carbamate

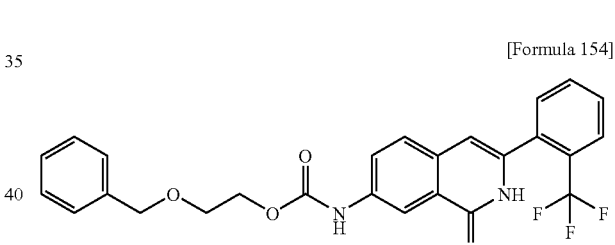

[Formula 154]

¹H-NMR (400 MHz, CDCl₃) δ (ppm): 3.75 (2H, t, J=4.7 Hz), 4.39 (2H, t, J=4.7 Hz), 4.60 (2H, s), 6.48 (1H, s), 7.02-7.12 (1H, m), 7.29-7.37 (5H, m), 7.52-7.69 (4H, m), 7.82 (1H, d, J=7.2 Hz), 8.05-8.15 (2H, m), 8.49 (1H, brs)
ESI (LC-MS positive mode) m/z 483 (M+H).

Example 131

2-Hydroxyethyl[1-oxo-3-(2-trifluoromethylphenyl)-1,2-dihydroisoquinolin-7-yl]carbamate

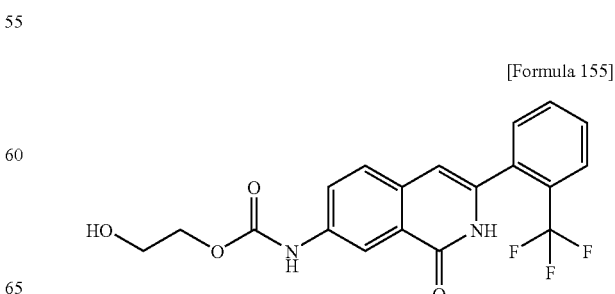

[Formula 155]

4.5 mg of 10% Pd/C was added to a methanol solution (5 ml) containing 44.9 mg (0.093 mmol) of 2-benzyloxyethyl [1-oxo-3-(2-trifluoromethylphenyl)-1,2-dihydroisoquinolin-7-yl]carbamate obtained in Example 130. The obtained mixture was intensively stirred under a hydrogen atmosphere at a room temperature for 2 hours 20 minutes. Thereafter, insoluble matters were removed by filtration, and the filtrate was then concentrated. The obtained residue was purified by silica gel column chromatography (ethyl acetate), so as to obtain 33 mg (90%) of 2-hydroxyethyl[1-oxo-3-(2-trifluoromethylphenyl)-1,2-dihydroisoquinolin-7-yl]carbamate.

$^1$H-NMR (400 MHz, CDCl$_3$) δ (ppm): 2.68-2.78 (1H, m), 3.83-3.93 (2H, m), 4.33 (2H, t, J=4.6 Hz), 6.51 (1H, s), 7.53-7.67 (5H, m), 7.79 (1H, d, J=7.3 Hz), 8.14-8.24 (2H, m), 8.94 (1H, brs)

ESI (LC-MS positive mode) m/z 393 (M+H).

Example 132

(R)-2,3-Bisbenzyloxypropyl[1-oxo-3-(2-trifluoromethylphenyl)-1,2-dihydroisoquinolin-7-yl]carbamate

[Formula 156]

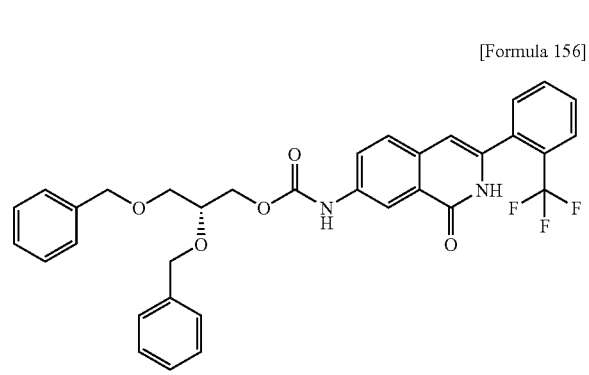

A mixture consisting of 0.50 ml (1.98 mmol) of (S)-(−)-1,2-dibenzylglycerol and 0.69 ml (3.96 mmol) of N,N-diisopropylethylamine was dissolved in 5 ml of dichloromethane. The obtained solution was added dropwise to 5 ml of a dichloromethane solution containing 294 mg (0.99 mmol) of triphosgene under cooling on ice. The obtained mixture was stirred at a room temperature for 30 minutes. Thereafter, the reaction solution was concentrated, and the concentrate was then dissolved in 5 ml of dichloromethane, so as to obtain a dichloromethane solution of (R)-2,3-bis-benzyloxy-propyl chloroformate (1.98 mmol/5 ml).

A mixture consisting of 100 mg (0.33 mmol) of the 7-amino-3-(2-trifluoromethylphenyl)-2H-isoquinolin-1-one prepared in Example 38 and 0.29 ml (1.65 mmol) of N,N-diisopropylethylamine was dissolved in 3 ml of dichloromethane, and 2.5 ml of the aforementioned chloroformate solution was then added thereto under cooling on ice. The obtained mixture was stirred at a room temperature for 20 hours. Thereafter, the reaction solution was poured into a saturated ammonium chloride aqueous solution, followed by extraction with ethyl acetate. The extract was washed with a saturated saline solution, and was then dried over anhydrous sodium sulfate, followed by concentration. The obtained residue was purified by silica gel chromatography (dichloromethane:methanol=100:1), so as to obtain 49 mg (25%) of (R)-2,3-bisbenzyloxypropyl [1-oxo-3-(2-trifluoromethylphenyl)-1,2-dihydroisoquinolin-7-yl]carbamate in the form of a light yellow oily substance.

$^1$H-NMR (270 MHz, DMSO-d$_6$) δ (ppm): 3.60 (2H, ddd, J=12.0, 10.1, 5.3 Hz), 3.84 (1H, m), 4.27 (1H, dd, J=11.6, 5.3 Hz), 4.38 (1H, dd, J=11.6, 4.0 Hz), 4.50 (2H, s), 4.63 (2H, s), 6.48 (1H, s), 7.23-7.33 (11H, m), 7.45-7.60 (4H, m), 7.74 (1H, d, J=8.2 Hz), 7.93 (1H, s), 8.17 (1H, brs), 9.72 (1H, brs)

ESI (LC-MS positive mode) m/z 603 (M+H).

The following compounds (Examples 133-137) were synthesized by a method similar to that of Example 132, using the 7-amino-3-(2-trifluoromethylphenyl)-2H-isoquinolin-1-one and a suitable alcohol or thiol as starting materials.

Example 133

2-Benzyloxy-1-benzyloxymethylethyl[1-oxo-3-(2-trifluoromethylphenyl)-1,2-dihydroisoquinolin-7-yl]carbamate

[Formula 157]

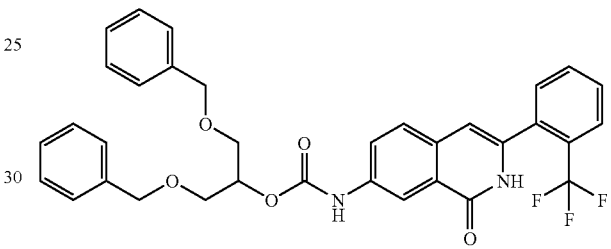

$^1$H-NMR (270 MHz, DMSO-d$_6$) δ (ppm): 3.71 (4H, d, J=5.0 Hz), 4.49 (2H, d, J=12.0 Hz), 4.54 (2H, d, J=12.2 Hz), 5.20 (1H, dt, J=5.0, 5.0 Hz), 6.45 (1H, s), 7.24-7.31 (10H, m), 7.50-7.63 (4H, m), 7.75 (1H, d, J=8.2 Hz), 7.83 (1H, brs), 8.12 (1H, d, J=2.3 Hz), 8.17 (1H, d, J=8.4 Hz), 9.89 (1H, brs)

ESI (LC-MS positive mode) m/z 603 (M+H).

Example 134

Cyclohexylmethyl[1-oxo-3-(2-trifluoromethylphenyl)-1,2-dihydroisoquinolin-7-yl]carbamate

[Formula 158]

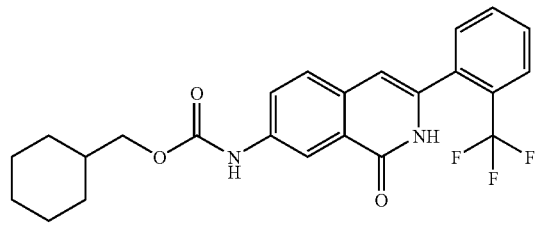

$^1$H-NMR (270 MHz, DMSO-d$_6$) δ (ppm): 0.97-1.25 (6H, m), 1.64-1.76 (5H, m), 3.93 (2H, d, J=6.4 Hz), 6.40 (1H, s), 7.58-7.86 (6H, m), 8.38 (1H, d, J=2.3 Hz), 9.92 (1H, s), 11.50 (1H, s)

ESI (LC-MS positive mode) m/z 445 (M+H).

Example 135

Cyclohexyl[1-oxo-3-(2-trifluoromethylphenyl)-1,2-dihydroisoquinolin-7-yl]carbamate

[Formula 159]

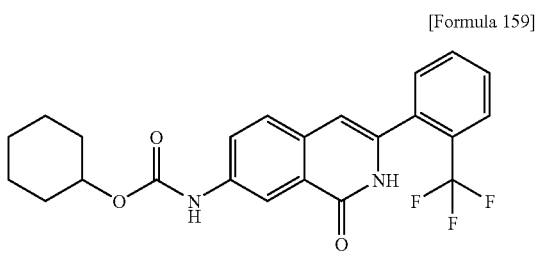

¹H-NMR (270 MHz, DMSO-d₆) δ (ppm): 1.15-1.99 (10H, m), 4.67 (1H, m), 6.41 (1H, s), 7.59-7.88 (6H, m), 8.40 (1H, d, J=2.2 Hz), 9.90 (1H, s), 11.48 (1H, s)
ESI (LC-MS positive mode) m/z 431 (M+H).

Example 136

Furan-3-ylmethyl[1-oxo-3-(2-trifluoromethylphenyl)-1,2-dihydroisoquinolin-7-yl]carbamate

[Formula 160]

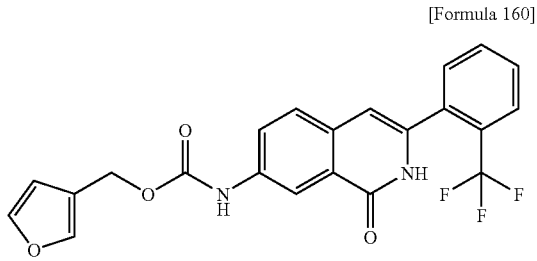

¹H-NMR (270 MHz, DMSO-d₆) δ (ppm): 5.06 (2H, s), 6.41 (1H, s), 6.60 (1H, s), 7.59-7.87 (9H, m), 8.40 (1H, d, J=2.3 Hz), 10.0 (1H, brs)
ESI (LC-MS positive mode) m/z 429 (M+H).

Example 137

S-Ethyl[1-oxo-3-(2-trifluoromethylphenyl)-1,2-dihydroisoquinolin-7-yl]thiocarbamate

[Formula 161]

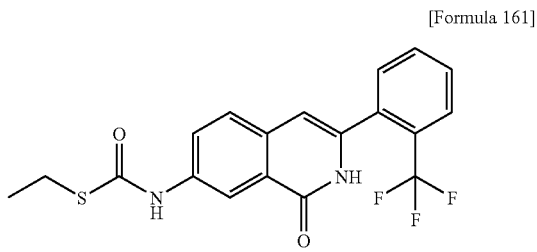

¹H-NMR (270 MHz, DMSO-d₆) δ (ppm): 1.29 (3H, t, J=7.3 Hz), 2.92 (2H, dd, J=14.5, 7.3 Hz), 6.44 (1H, s), 7.62-7.89 (6H, m), 8.48 (1H, d, J=2.3 Hz), 10.60 (1H, s), 11.55 (1H, s)
ESI (LC-MS positive mode) m/z 393 (M+H).

Example 138

(R)-2,3-Dihydroxypropyl[1-oxo-3-(2-trifluoromethylphenyl)-1,2-dihydroisoquinolin-7-yl]carbamate

[Formula 162]

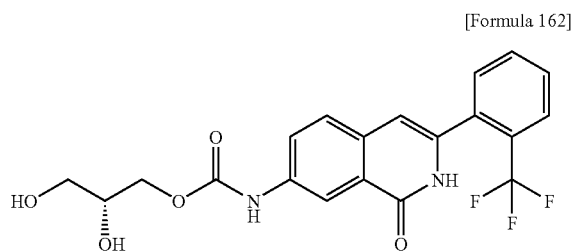

A mixture consisting of 26 mg (0.043 mmol) of (R)-2,3-bisbenzyloxypropyl[1-oxo-3-(2-trifluoromethylphenyl)-1,2-dihydroisoquinolin-7-yl]carbamate synthesized in Example 132; 5 mg (0.036 mmol) of palladium hydroxide; and 0.2 ml (3.49 mmol) of acetic acid, was suspended in 3 ml of ethanol, and the obtained suspension was then stirred under a hydrogen atmosphere for 2 hours. Thereafter, the reaction solution was filtrated with celite, and was then concentrated. The obtained residue was purified by silica gel chromatography (dichloromethane:methanol=10:1), so as to obtain 18 mg (100%) of (R)-2,3-dihydroxypropyl[1-oxo-3-(2-trifluoromethylphenyl)-1,2-dihydroisoquinolin-7-yl]carbamate in the form of a light yellow oily substance.

¹H-NMR (270 MHz, DMSO-d₆) δ (ppm): 3.42 (2H, m), 3.73 (1H, dt, J=5.0, 5.0 Hz), 4.03 (1H, dd, J=11.0, 6.4 Hz), 4.17 (1H, dd, 11.0, 4.2 Hz), 5.40 (2H, brs), 6.41 (1H, s), 7.59-7.88 (6H, m), 8.41 (1H, s), 10.04 (1H, s), 11.50 (1H, brs)
ESI (LC-MS positive mode) m/z 423 (M+H).

Example 139

2-Hydroxy-1-hydroxymethylethyl[1-oxo-3-(2-trifluoromethylphenyl)-1,2-dihydroisoquinolin-7-yl]carbamate

[Formula 163]

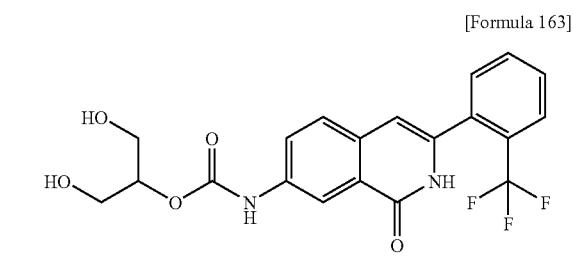

The above compound was synthesized by a method similar to that of Example 138, using the 2-benzyloxy-1-benzyloxymethylethyl[1-oxo-3-(2-trifluoromethylphenyl)-1,2-dihydroisoquinolin-7-yl]carbamate synthesized in Example 133 as a starting material.

¹H-NMR (270 MHz, DMSO-d₆) δ (ppm): 3.58 (2H, dd, J=11.6, 5.5 Hz), 3.63 (2H, dd, J=11.6, 5.5 Hz), 4.77 (1H, dt, J=5.5, 5.5 Hz), 5.70 (2H, brs), 6.41 (1H, s), 7.59-7.88 (6H, m), 8.42 (1H, s), 10.02 (1H, s) 11.50 (1H, brs)
ESI (LC-MS positive mode) m/z 423 (M+H).

Example 140

Ethyl[3-(2-morpholin-4-ylphenyl)-1-oxo-1,2-dihydroisoquinolin-7-yl]carbamate

Step A

7-Amino-3-(2-morpholin-4-ylphenyl)-2H-isoquinolin-1-one

[Formula 164]

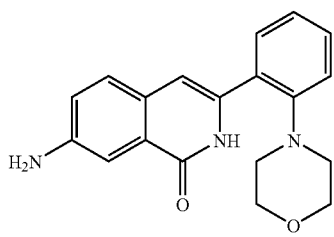

The above compound was synthesized by a method similar to that of Example 38, using the 7-chloro-3-(2-morpholin-4-ylphenyl)-2H-isoquinolin-1-one synthesized in Step A of Example 97 as a raw material.
¹H-NMR (400 MHz, CDCl₃) δ (ppm): 2.95-2.99 (4H, m), 3.84-3.90 (4H, m), 4.00 (2H, brs), 6.67 (1H, s), 7.05 (1H, dd, J=2.0, 7.1 Hz), 7.10-7.20 (2H, m), 7.35-7.45 (2H, m), 7.55-7.59 (1H, m), 7.64 (1H, d, J=2.4 Hz), 10.86 (1H, brs)
ESI (LC-MS positive mode) m/z 322 (M+H).

Step B

Ethyl[3-(2-morpholin-4-ylphenyl)-1-oxo-1,2-dihydroisoquinolin-7-yl]carbamate

[Formula 165]

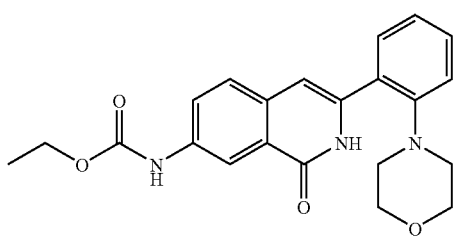

The above compound was synthesized by a method similar to that of Example 57, using the 7-amino-3-(2-morpholin-4-ylphenyl)-2H-isoquinolin-1-one obtained in Step A as a starting material.
¹H-NMR (400 MHz, CDCl₃) δ (ppm): 1.35 (3H, t, J=7.2 Hz), 2.98 (4H, t, J=4.4 Hz), 3.88 (4H, t, J=4.4 Hz), 4.27 (2H, q, J=7.2 Hz), 6.72 (1H, s), 6.81 (1H, brs), 6.99-7.25 (2H, m), 7.37-7.43 (1H, m), 7.56-7.63 (2H, m), 8.04 (1H, brs), 8.20 (1H, bs), 10.95 (1H, brs)
ESI (LC-MS positive mode) m/z 394 (M+H).

Example 141

Ethyl[3-(4-fluoro-2-trifluoromethylphenyl)-1-oxo-1,2-dihydroisoquinolin-7-yl]carbamate

[Formula 166]

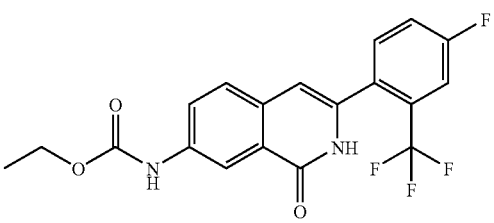

The above compound was synthesized by a method similar to that of Example 140.
¹H-NMR (400 MHz, CDCl₃) δ (ppm): 1.35 (3H, t, J=6.8 Hz), 4.27 (2H, q, J=6.8 Hz), 6.46 (1H, s), 6.85 (1H, brs), 7.35-7.39 (1H, m), 7.51-7.57 (3H, m), 8.09 (1H, brs), 8.17 (1H, brs), 8.45 (1H, brs)
ESI (LC-MS positive mode) m/z 395 (M+H).

Example 142

Ethyl[1-oxo-3-(2-trifluoromethoxyphenyl)-1,2-dihydroisoquinolin-7-yl]carbamate

[Formula 167]

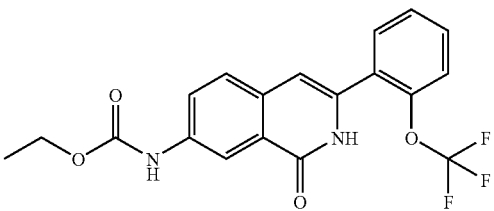

The above compound was synthesized by a method similar to that of Example 141.
¹H-NMR (270 MHz, CDCl₃) δ (ppm): 1.35 (3H, t, J=7.1 Hz), 4.28 (2H, q, J=7.1 Hz), 6.66 (1H, s), 6.83-6.93 (1H, m), 7.40-7.61 (5H, m), 8.08-8.13 (2H, m), 8.64 (1H, brs)
ESI (LC-MS positive mode) m/z 393 (M+H).

Example 143

Ethyl methyl[1-oxo-3-(2-trifluoromethylphenyl)-1,2-dihydroisoquinolin-7-yl]carbamate

[Formula 168]

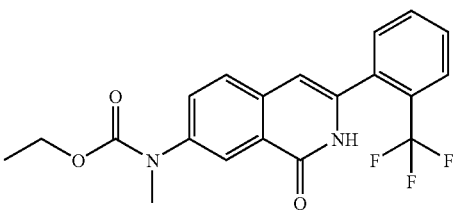

The above compound was synthesized by a method similar to that of Example 57, using the 7-methylamino-3-(2-trifluoromethylphenyl)-2H-isoquinolin-1-one obtained in Step B of Example 119 as a starting material.

¹H-NMR (270 MHz, CDCl₃) δ (ppm): 1.27 (3H, t, J=7.1 Hz), 3.41 (3H, s), 4.22 (2H, q, J=7.1 Hz), 6.52 (1H, s), 7.55-7.72 (5H, m), 7.83 (1H, dd, J=1.7, 8.1 Hz), 8.20 (1H, d, J=2.3 Hz), 8.72 (1H, brs)

ESI (LC-MS positive mode) m/z 391 (M+H).

Example 144

2-Hydroxyethyl methyl[1-oxo-3-(2-trifluoromethylphenyl)-1,2-dihydroisoquinolin-7-yl]carbamate

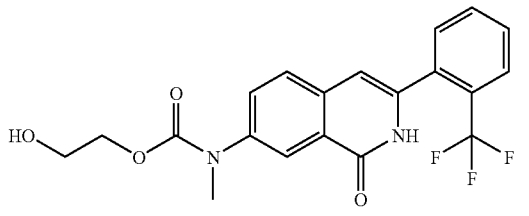

[Formula 169]

The above compound was synthesized by applying a method similar to that of Example 130 and then applying a method similar to that of Example 131, using the 7-methylamino-3-(2-trifluoromethylphenyl)-2H-isoquinolin-1-one obtained in Step B of Example 119 as a starting material.

¹H-NMR (500 MHz, CDCl₃) δ (ppm): 2.47 (1H, brs), 3.43 (3H, s), 3.78-3.88 (2H, m), 4.29-4.33 (2H, m), 6.52 (1H, s), 7.53-7.60 (2H, m), 7.63-7.71 (3H, m), 7.82-7.84 (1H, m), 8.26 (1H, d, J=1.81 Hz), 8.72 (1H, brs)

EI-MS m/z 406 (M⁺).

Example 145

3-(4-Hydroxy-2-methylphenyl)-7-(3-hydroxypiperidin-1-yl)-2H-isoquinolin-1-one

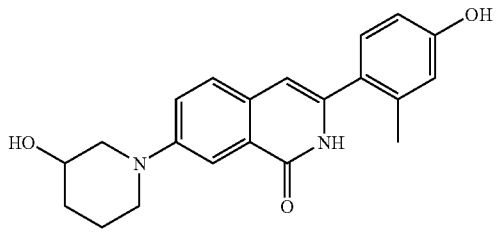

[Formula 170]

0.070 ml (0.070 mmol) of a 1 M boron tribromide dichloromethane solution was added at 0° C. to a dichloromethane solution (0.5 ml) containing 17 mg (0.0466 mmol) of the 7-(3-hydroxypiperidin-1-yl)-3-(4-methoxy-2-methylphenyl)-2H-isoquinolin-1-one obtained in Example 90. The obtained mixture was stirred at the same above temperature for 30 minutes. Thereafter, a saturated sodium bicarbonate aqueous solution was added to the reaction solution, and the mixture was then extracted with dichloromethane/methanol (5:1). The extract was concentrated under reduced pressure.

The obtained residue was purified by silica gel column chromatography (dichloromethane:methanol=20:1 to 10:1), so as to obtain 10 mg (61%) of 3-(4-hydroxy-2-methylphenyl)-7-(3-hydroxypiperidin-1-yl)-2H-isoquinolin-1-one in the form of a light brown solid.

¹H-NMR (270 MHz, CD₃OD) δ (ppm): 1.30-1.43 (1H, m), 1.52-1.66 (1H, m), 1.77-1.95 (2H, m), 2.17 (3H, s), 2.70 (1H, dd, J=11.5, 8.5 Hz), 2.76-2.85 (1H, m), 3.41-3.50 (1H, m), 3.60-3.76 (2H, m), 6.36 (1H, s), 6.60 (1H, dd, J=8.5, 2.5 Hz), 6.63 (1H, d, J=2.5 Hz), 7.07 (1H, d, J=8.5 Hz), 7.38 (1H, dd, J=9.0, 2.5 Hz), 7.44 (1H, d, J=9.0 Hz), 7.61 (1H, d, J=2.5 Hz)

ESI (LC-MS positive mode) m/z 351 (M+H).

Example 146

3-(2-Chlorophenyl)-7-morpholin-4-yl-2H-isoquinolin-1-one

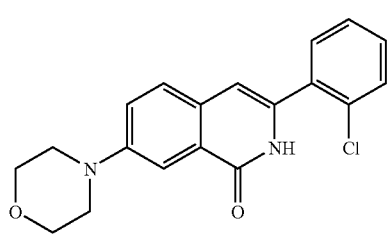

[Formula 171]

The above compound was synthesized by a method similar to that in Step B of Example 1, using the 2,N,N-trimethyl-5-morpholin-4-ylbenzamide prepared in Step B of Example 80 as a raw material.

¹H-NMR (400 MHz, CDCl₃) δ (ppm): 3.32 (4H, m), 3.91 (4H, m), 6.57 (1H, s), 7.34-7.41 (3H, m), 7.48-7.53 (3H, m), 7.81 (1H, d, J=2.9 Hz), 8.49 (1H, brs)

ESI (LC-MS positive mode) m/z 341 (M+H).

Example 147

2-Hydroxy-N-(1-oxo-3-phenyl-1,2-dihydroisoquinolin-7-yl)acetamide

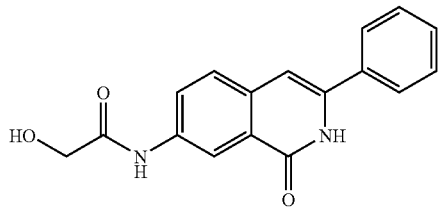

[Formula 172]

Dichloromethane was added to 5 ml of a whitish methanol solution containing the 2-benzyloxy-N-(1-oxo-3-phenyl-1,2-dihydroisoquinolin-7-yl)acetamide prepared in Example 60, until the solution became transparent. Thereafter, 10 mg of 10% Pd—C was added thereto, and the obtained mixture was then stirred under a hydrogen atmosphere for 8 hours. Thereafter, the reaction solution was filtrated with celite, and the filtrate was then concentrated, so as to obtain 7.8 mg (46%) of 2-hydroxy-N-(1-oxo-3-phenyl-1,2-dihydroisoquinolin-7-yl)acetamide in the form of a yellow solid.

¹H-NMR (270 MHz, DMSO-d₆) δ (ppm): 4.04 (2H, s), 5.81 (1H, brs), 6.68 (1H, s), 7.44-7.52 (2H, m), 7.67 (1H, d, J=8.58 Hz), 7.77-7.80 (2H, m), 7.97 (1H, dd, J=1.98, 8.58 Hz), 8.68 (1H, d, J=2.31 Hz), 11.46 (1H, m)

EI-MS m/z 293 (M−H⁺).

Example 148

3-Phenyl-7-((2S,3R)-2,3,4-trihydroxybutylamino)-2H-isoquinolin-1-one

[Formula 173]

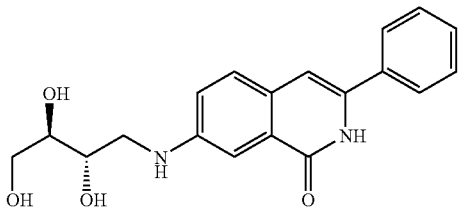

The above compound was synthesized by a method similar to that of Example 41, using the 7-amino-3-phenyl-2H-isoquinolin-1-one prepared in Example 39 as a raw material.

$^1$H-NMR (270 MHz, CD$_3$OD) δ (ppm): 3.24 (1H, dd, J=7.59, 12.87 Hz), 3.57-3.64 (2H, m), 3.68 (1H, d, J=5.94 Hz), 3.77-3.86 (2H, m), 6.84 (1H, s), 7.19 (1H, dd, J=2.31, 8.58 Hz), 7.37-7.52 (5H, m), 7.66-7.70 (2H, m)

FAB-MS m/z 341 (M+H).

Example 149

7-(2,2-Dimethylhydrazino)-3-(2-trifluoromethylphenyl)-2H-isoquinolin-1-one

[Formula 174]

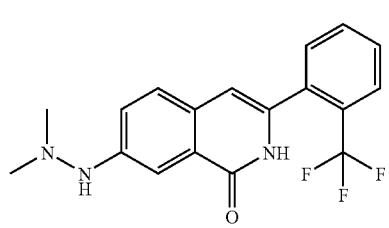

The above compound was synthesized via a reaction similar to that of Example 4, using the 7-chloro-3-(2-trifluoromethylphenyl)-2H-isoquinolin-1-one prepared in Step B of Example 1 as a raw material.

$^1$H-NMR (270 MHz, CDCl$_3$) δ (ppm): 2.58 (6H, s), 4.54 (1H, s), 6.44 (1H, s), 7.32 (1H, dd, J=2.5, 8.6 Hz), 7.44 (1H, d, J=8.6 Hz), 7.50-7.68 (3H, m), 7.76-7.83 (2H, m), 8.58 (1H, brs)

ESI (LC-MS positive mode) m/z 348 (M+H).

Example 150

3-(2-Trifluoromethylphenyl)-7-(1,2,2-trimethylhydrazino)-2H-isoquinolin-1-one

[Formula 175]

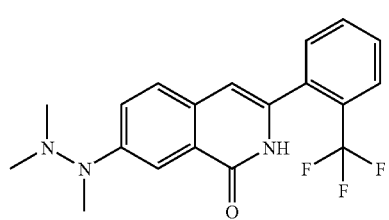

0.1 ml of acetic acid, 26.2 μl of a 37% formalin aqueous solution, and 25.3 mg (0.403 mmol) of sodium cyanoborohydride were added to 1 ml of a methanol solution containing 28 mg of the 7-(2,2-dimethylhydrazino)-3-(2-trifluoromethylphenyl)-2H-isoquinolin-1-one obtained in Example 149. The obtained mixture was stirred at a room temperature overnight. Thereafter, a saturated sodium bicarbonate aqueous solution was added to the reaction solution. The mixture was extracted with ethyl acetate, and was then dried over anhydrous sodium sulfate. The extract was concentrated. The obtained residue was purified by silica gel column chromatography (ethyl acetate:hexane=1:2 to 2:1), so as to obtain 25.5 mg (88%) of 3-(2-trifluoromethylphenyl)-7-(1,2,2-trimethylhydrazino)-2H-isoquinolin-1-one in the form of a light yellow solid.

$^1$H-NMR (270 MHz, CDCl$_3$) δ (ppm): 2.52 (6H, s), 2.92 (3H, s), 6.46 (1H, s), 7.46 (1H, d, J=8.9 Hz), 7.50-7.67 (4H, m), 7.72 (1H, dd, J=2.6, 8.9 Hz), 7.76-7.83 (1H, m), 8.33 (1H, brs)

ESI (LC-MS positive mode) m/z 362 (M+H).

Example 151

7-(N-Benzhydrylidenehydrazino)-3-(2-trifluoromethylphenyl)-2H-isoquinolin-1-one

[Formula 176]

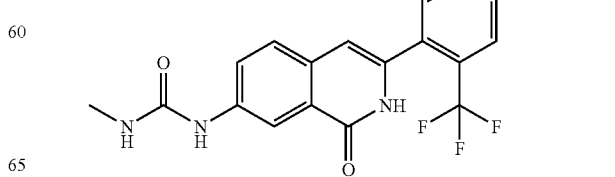

The above compound was synthesized via a reaction similar to that of Example 4, using the 7-chloro-3-(2-trifluoromethylphenyl)-2H-isoquinolin-1-one prepared in Step B of Example 1 as a raw material.

$^1$H-NMR (270 MHz, CDCl$_3$) δ (ppm): 6.47 (1H, s), 7.30-7.40 (5H, m), 7.47-7.70 (9H, m), 7.71-7.84 (4H, m), 8.36 (1H, brs)

ESI (LC-MS positive mode) m/z 484 (M+H).

Example 152

1-Methyl-3-[1-oxo-3-(2-trifluoromethylphenyl)-1,2-dihydroisoquinolin-7-yl]urea

[Formula 177]

0.5 ml of a 1,4-dioxane solution contained 20.8 mg (0.05 mmol) of the 7-iodo-3-(2-trifluoromethylphenyl)-2H-isoquinolin-1-one obtained in Step A of Example 114; 2.2 mg (0.0025 mmol) of tris(dibenzylideneacetone)dipalladium; 4.2 mg (0.0075 mmol) of 9,9-dimethyl-4,5-bis(diphenylphosphino)xanthene; 22.8 mg (0.07 mmol) of cesium carbonate, and 4.44 mg (0.06 mmol) of methylurea, was stirred at 110° C. overnight. Thereafter, the reaction solution was cooled to a room temperature, and a saturated ammonium chloride aqueous solution was then added thereto. The mixture was extracted with ethyl acetate, and the extract was then dried over anhydrous sodium sulfate. The extract was concentrated, and the obtained residue was then purified by thin-layer chromatography (methylene chloride:methanol=20:1), so as to obtain 1.7 mg (9%) of 1-methyl-3-[1-oxo-3-(2-trifluoromethylphenyl)-1,2-dihydroisoquinolin-7-yl]urea in the form of a colorless solid.

$^1$H-NMR (270 MHz, DMSO-$d_6$) δ (ppm): 2.67 (3H, d, J=4.6 Hz), 6.25-6.35 (1H, m), 6.38 (1H, s), 7.54 (1H, d, J=8.6 Hz), 7.57-7.90 (5H, m), 8.28 (1H, d, J=2.3 Hz), 9.04 (1H, brs), 11.40 (1H, brs)

ESI (LC-MS positive mode) m/z 362 (M+H).

Example 153

N-Methyl-N-[1-oxo-3-(2-trifluoromethylphenyl)-1,2-dihydroisoquinolin-7-yl]formamide

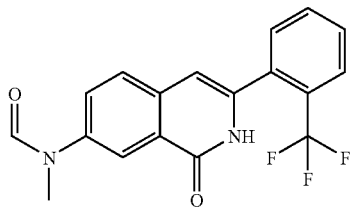

[Formula 178]

The above compound was synthesized by a method similar to that of Example 57, using the 7-methylamino-3-(2-trifluoromethylphenyl)-2H-isoquinolin-1-one obtained in Step B of Example 119 as a starting material.

$^1$H-NMR (270 MHz, CDCl$_3$) δ (ppm): 3.41 (3H, s), 6.54 (1H, s), 7.47-7.74 (5H, m), 7.79-7.88 (1H, m), 8.14 (1H, d, J=2.6 Hz), 8.63 (1H, s), 9.37 (1H, brs)

ESI (LC-MS positive mode) m/z 347 (M+H).

Example 154

N-[1-Oxo-3-(2-trifluoromethylphenyl)-1,2-dihydroisoquinolin-7-yl]benzamide

[Formula 179]

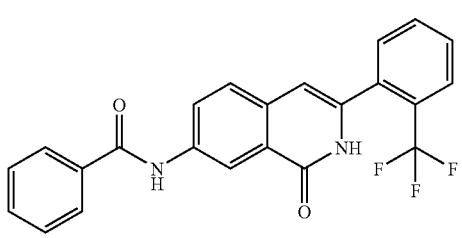

The above compound was synthesized by a method similar to that of Example 57, using the 7-amino-3-(2-trifluoromethylphenyl)-2H-isoquinolin-1-one obtained in Example 38 as a starting material.

$^1$H-NMR (270 MHz, DMSO-$d_6$) δ (ppm): 6.48 (1H, s), 7.54-7.82 (8H, m), 7.89 (1H, d, J=7.8 Hz), 8.05 (2H, dd, J=7.8, 2.1 Hz), 8.75 (1H, d, J=2.1 Hz), 10.59 (1H, s), 11.57 (1H, s)

ESI (LC-MS positive mode) m/z 409 (M+H).

Example 155

N-[1-Oxo-3-(2-trifluoromethylphenyl)-1,2-dihydroisoquinolin-7-yl]-2-thiophen-2-ylacetamide

[Formula 180]

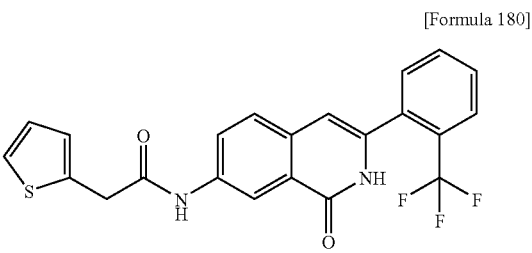

The above compound was synthesized by a method similar to that of Example 57, using the 7-amino-3-(2-trifluoromethylphenyl)-2H-isoquinolin-1-one obtained in Example 38 as a starting material.

$^1$H-NMR (270 MHz, DMSO-$d_6$) δ (ppm): 3.95 (2H, s), 6.45 (1H, s), 7.00-7.04 (2H, m), 7.42 (1H, dd, J=5.0, 1.4 Hz), 7.62-7.80 (4H, m), 7.86 (1H, d, J=8.7 Hz), 7.93 (1H, dd, J=8.7, 2.1 Hz), 8.55 (1H, d, J=2.1 Hz), 10.55 (1H, s), 11.54 (1H, s)

ESI (LC-MS positive mode) m/z 429 (M+H).

Example 156

N-(1-Oxo-3-phenyl-1,2-dihydroisoquinolin-7-yl)acetamide

[Formula 181]

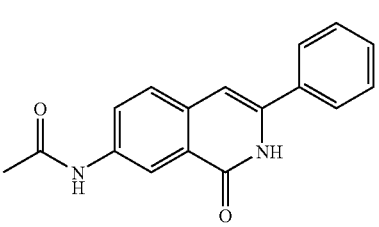

The above compound was synthesized by a method similar to that of Example 57, using the 7-amino-3-phenyl-2H-isoquinolin-1-one obtained in Example 39 as a starting material.

$^1$H-NMR (270 MHz, DMSO-$d_6$) δ (ppm): 2.10 (3H, s), 6.87 (1H, s), 7.40-7.52 (3H, m), 7.65 (1H, d, J=8.4 Hz), 7.78 (2H, d, J=8.4 Hz), 7.86 (1H, d, J=8.4 Hz), 8.52 (1H, s), 10.22 (1H, s), 11.43 (1H, s)

EIMS m/z 278 (M$^+$).

Example 157

6-Chloro-7-morpholin-4-yl-3-(2-trifluoromethylphenyl)-2H-isoquinolin-1-one

Step A

2,N-Dimethyl-5-morpholin-4-ylbenzamide

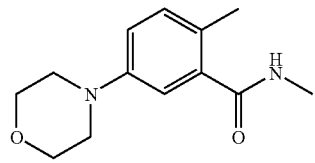

[Formula 182]

The above compound was synthesized by a method similar to that in Step B of Example 80, using the 5-chloro-2,N-dimethylbenzamide obtained in Step A of Example 1 as a starting material.

$^1$H-NMR (400 MHz, CDCl$_3$) δ (ppm): 2.34 (3H, s), 2.99 (3H, d, J=5.2 Hz), 3.11 (4H, t, J=4.8 Hz), 3.85 (4H, t, J=4.6 Hz), 5.71 (1H, brs), 6.87 (1H, dd, J=2.4, 8.4 Hz), 6.91 (1H, d, J=3.2 Hz), 7.11 (1H, d, J=8.4 Hz)

ESI (LC-MS positive mode) m/z 235 (M+H).

Step B

4-Chloro-2,N-dimethyl-5-morpholin-4-ylbenzamide and 2-chloro-6,N-dimethyl-3-morpholin-4-ylbenzamide

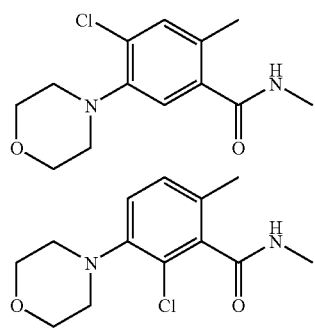

[Formula 183]

100 mg (0.427 mmol) of 2,N-dimethyl-5-morpholin-4-ylbenzamide prepared in Step A was dissolved in 3 ml of N,N-dimethylformamide, and thereafter, 63 mg (0.47 mmol) of N-chlorosuccinimide was added thereto under cooling on ice. The obtained mixture was stirred at 50° C. for 1 hour. Thereafter, the reaction solution was concentrated, and water was then added thereto. The mixture was extracted with ethyl acetate. The extract was washed with water and a saturated saline solution, and was then dried over anhydrous sodium sulfate. The extract was concentrated, and the obtained residue was then purified by silica gel column chromatography (ethyl acetate:methylene chloride=1:5), so as to obtain 54.5 mg (47%) of 4-chloro-2,N-dimethyl-5-morpholin-4-ylbenzamide in the form of a colorless solid, as well as 46 mg (40%) of 2-chloro-6,N-dimethyl-3-morpholin-4-ylbenzamide in the form of a colorless solid.

4-Chloro-2,N-dimethyl-5-morpholin-4-ylbenzamide $^1$H-NMR (400 MHz, CDCl$_3$) δ (ppm): 2.36 (3H, s), 2.97-3.03 (7H, m), 3.87 (4H, t, J=4.4 Hz), 5.72 (1H, brs), 7.03 (1H, s), 7.23 (1H, s)

ESI (LC-MS positive mode) m/z 269 (M+H).

2-Chloro-6,N-dimethyl-3-morpholin-4-ylbenzamide $^1$H-NMR (400 MHz, CDCl$_3$) δ (ppm): 2.28 (3H, s), 3.00 (4H, t, J=4.6 Hz), 3.04 (3H, d, J=4.8 Hz), 3.86 (4H, t, J=4.4 Hz), 5.64 (1H, brs), 6.96 (1H, d, J=8.4 Hz), 7.08 (1H, d, J=8.4 Hz)

ESI (LC-MS positive mode) m/z 269 (M+H).

Step C

6-Chloro-7-morpholin-4-yl-3-(2-trifluoromethylphenyl)-2H-isoquinolin-1-one

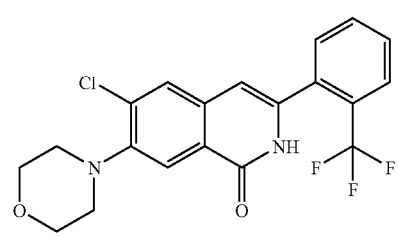

[Formula 184]

167 μl of a 1.8 M lithium diisopropylamide THF solution (0.3 mmol) was diluted with 1.5 ml of THF. Thereafter, 1 ml of a THF solution containing 27 mg (0.10 mol) of the 4-chloro-2,N-dimethyl-5-morpholin-4-ylbenzamide prepared in Step B was added dropwise to the diluted solution at −78° C. Thereafter, 1 ml of a THF solution containing 17 mg (0.10 mmol) of 2-(trifluoromethyl)benzonitrile was further added thereto, and the obtained mixture was then stirred at −78° C. for 1 hour. The temperature of the reaction solution was increased to 0° C., and a saturated ammonium chloride aqueous solution was added thereto, followed by extraction with ethyl acetate. The extract was washed with a saturated saline solution, and was then dried over anhydrous sodium sulfate, followed by concentration under reduced pressure. Thereafter, the obtained residue was purified by silica gel column chromatography (ethyl acetate:hexane=1:2 to 1:1), so as to obtain 5.4 mg (13%) of 6-chloro-7-morpholin-4-yl-3-(2-trifluoromethylphenyl)-2H-isoquinolin-1-one in the form of a colorless solid.

$^1$H-NMR (400 MHz, CDCl$_3$) δ (ppm): 3.17 (4H, t, J=4.6 Hz), 3.92 (4H, t, J=4.6 Hz), 6.40 (1H, s), 7.53 (1H, d, J=7.6 Hz), 7.62-7.70 (3H, m), 7.82 (1H, d, J=7.6 Hz), 7.99 (1H, s), 8.62 (1H, brs)

ESI (LC-MS positive mode) m/z 409 (M+H).

Example 158

8-Chloro-7-morpholin-4-yl-3-(2-trifluoromethylphenyl)-2H-isoquinolin-1-one

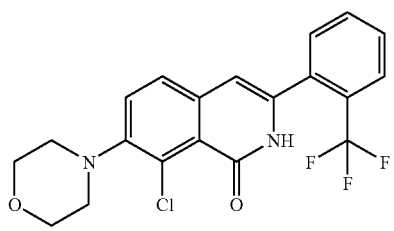

[Formula 185]

The above compound was synthesized by a method similar to that in Step C of Example 157, using the 2-chloro-6,N-dimethyl-3-morpholin-4-ylbenzamide obtained in Step B of Example 157 as a raw material.

$^1$H-NMR (400 MHz, CDCl$_3$) δ (ppm): 3.11 (4H, t, J=4.4 Hz), 3.93 (4H, t, J=4.4 Hz), 6.42 (1H, s), 7.40-7.47 (2H, m), 7.56 (1H, d, J=7.6 Hz), 7.61 (1H, t, J=7.6 Hz), 7.68 (1H, t, J=7.4 Hz), 7.81 (1H, d, J=8.0 Hz), 9.00 (1H, brs)

ESI (LC-MS positive mode) m/z 409 (M+H).

Example 159

6,8-Dichloro-7-morpholin-4-yl-3-(2-trifluoromethylphenyl)-2H-isoquinolin-1-one

Step A 2,4-Dichloro-6,N-dimethyl-3-morpholin-4-ylbenzamide

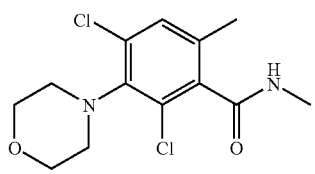

[Formula 186]

70 mg (0.30 mmol) of the 2,N-dimethyl-5-morpholin-4-ylbenzamide prepared in Step A of Example 157 was dissolved in 2 ml of N,N-dimethylformamide, and thereafter, 60 mg (0.45 mmol) of N-chlorosuccinimide was added thereto under cooling on ice. The obtained mixture was stirred at 0° C. for 1.5 hours, then at a room temperature for 0.5 hours, and then at 50° C. for 3 hours. Thereafter, the reaction solution was concentrated, and water was then added thereto, followed by extraction with ethyl acetate. The extract was washed with water and a saturated saline solution, and was then dried over anhydrous sodium sulfate. The extract was concentrated, and the obtained residue was then purified by silica gel column chromatography (ethyl acetate:methylene chloride=1:5), so as to obtain 17.3 mg (19%) of 2,4-dichloro-6,N-dimethyl-3-morpholin-4-ylbenzamide in the form of a colorless solid.

$^1$H-NMR (400 MHz, CDCl$_3$) δ (ppm): 2.27 (3H, s), 3.03 (3H, d, J=4.8 Hz), 3.11-3.24 (4H, m), 3.81 (4H, t, J=4.6 Hz), 5.67 (1H, brs), 7.14 (1H, s)

ESI (LC-MS positive mode) m/z 303 (M+H).

Step B 6,8-Dichloro-7-morpholin-4-yl-3-(2-trifluoromethylphenyl)-2H-isoquinolin-1-one

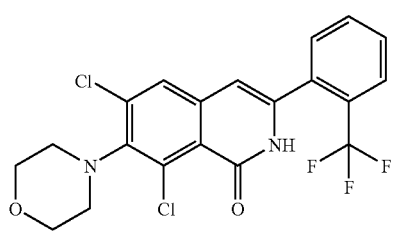

[Formula 187]

The above compound was synthesized by a method similar to that in Step C of Example 157, using the 2,4-dichloro-6,N-dimethyl-3-morpholin-4-ylbenzamide obtained in Step A as a raw material.

$^1$H-NMR (400 MHz, CDCl$_3$) δ (ppm): 3.15-3.18 (2H, m), 3.37-3.42 (2H, m), 3.83-3.91 (4H, m), 6.33 (1H, s), 7.49 (1H, s), 7.56 (1H, d, J=7.2 Hz), 7.62-7.71 (2H, m), 7.82 (1H, d, J=7.6 Hz), 9.39 (1H, brs)

ESI (LC-MS positive mode) m/z 444 (M+H).

Example 160

6-Fluoro-7-morpholin-4-yl-3-(2-trifluoromethylphenyl)-2H-isoquinolin-1-one

Step A

4-Fluoro-2,N,N-trimethyl-5-morpholin-4-ylbenzamide and 2-fluoro-6,N,N-trimethyl-3-morpholin-4-ylbenzamide

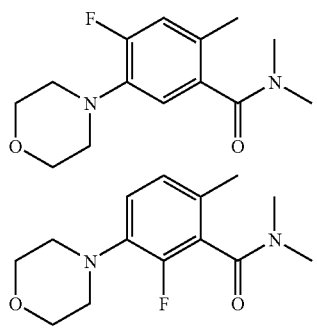

[Formula 188]

393 mg (1.10 mmol) of N,N'-difluoro-2,2'-bipyridinium bis(tetrafluoroborate) was added to 7 ml of an acetonitrile solution containing 458 mg (1.84 mmol) of the 2,N,N-trimethyl-5-morpholin-4-ylbenzamide obtained in Step B of Example 80 under cooling on ice. The obtained mixture was stirred at 0° C. for 1 hour, then at a room temperature for 1 hour, then at 50° C. for 1 hour, then at 80° C. for 2.5 days, and then under heating to reflux for 2 hours. Thereafter, 357 mg (1.0 mmol) of N,N'-difluoro-2,2'-bipyridinium bis(tetrafluoroborate) was further added to the reaction solution, and the obtained mixture was further stirred for 20 minutes. Thereafter, a saturated sodium bicarbonate aqueous solution was added to the reaction solution, and the mixture was then extracted with ethyl acetate. The extract was dried over anhydrous sodium sulfate, and was then concentrated. The obtained residue was purified by silica gel column chromatography (ethyl acetate:hexane=1:3 to 1:1), so as to obtain 25.8 mg (5.3%) of 4-fluoro-2,N,N-trimethyl-5-morpholin-4-ylbenzamide in the form of an oily substance, and also obtain 35.1 mg (7.2%) of 2-fluoro-6,N,N-trimethyl-3-morpholin-4-ylbenzamide in the form of an oily substance.

4-fluoro-2,N,N-trimethyl-5-morpholin-4-ylbenzamide $^1$H-NMR (400 MHz, CDCl$_3$) δ (ppm): 2.21 (3H, s), 2.84 (3H, s), 3.05 (4H, t, J=4.6 Hz), 3.12 (3H, s), 3.86 (4H, t, J=4.4 Hz), 6.75 (1H, d, J=8.8 Hz), 6.88 (1H, d, J=13.2 Hz)
ESI (LC-MS positive mode) m/z 267 (M+H).

2-fluoro-6,N,N-trimethyl-3-morpholin-4-ylbenzamide $^1$H-NMR (400 MHz, CDCl$_3$) δ (ppm): 2.21 (3H, s), 2.92 (3H, s), 2.93-2.97 (2H, m), 3.11-3.32 (2H, m), 3.17 (3H, s), 3.81-3.90 (4H, m), 6.84 (1H, t, J=8.6 Hz), 6.92 (1H, d, J=8.4 Hz)
ESI (LC-MS positive mode) m/z 267 (M+H).

Step B

6-Fluoro-7-morpholin-4-yl-3-(2-trifluoromethylphenyl)-2H-isoquinolin-1-one

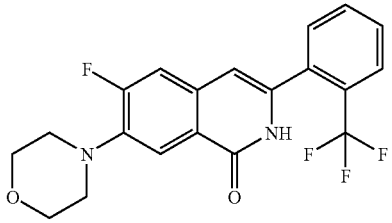

[Formula 189]

The above compound was synthesized by a method similar to that in Step C of Example 157, using the 4-fluoro-2, N,N-trimethyl-5-morpholin-4-ylbenzamide obtained in Step A as a raw material.

$^1$H-NMR (400 MHz, CDCl$_3$) δ (ppm): 3.21 (4H, t, J=4.6 Hz), 3.92 (4H, t, J=4.8 Hz), 6.41 (1H, s), 7.21 (1H, d, J=12.8 Hz), 7.53 (1H, d, J=7.2 Hz), 7.60-7.69 (2H, m), 7.82 (1H, d, J=8.0 Hz), 7.90 (1H, d, J=7.2 Hz), 8.52 (1H, brs)
ESI (LC-MS positive mode) m/z 393 (M+H).

Example 161

8-Fluoro-7-morpholin-4-yl-3-(2-trifluoromethylphenyl)-2H-isoquinolin-1-one

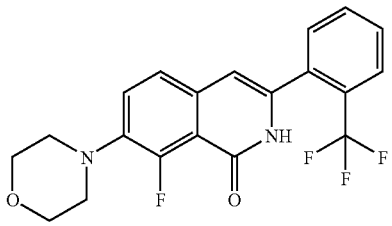

[Formula 190]

The above compound was synthesized by a method similar to that in Step C of Example 157, using the 2-fluoro-6, N,N-trimethyl-3-morpholin-4-ylbenzamide obtained in Step A of Example 160 as a raw material.

$^1$H-NMR (400 MHz, CDCl$_3$) δ (ppm): 3.17-3.20 (4H, m), 3.89-3.91 (4H, m), 6.40 (1H, d, J=2.0 Hz), 7.27-7.36 (2H, m), 7.53 (1H, d, J=7.2 Hz), 7.59-7.68 (2H, m), 7.81 (1H, d, J=7.2 Hz), 8.40 (1H, brs)
ESI (LC-MS positive mode) m/z 393 (M+H).

Example 162

3-Furan-2-yl-7-morpholin-4-yl-2H-isoquinolin-1-one

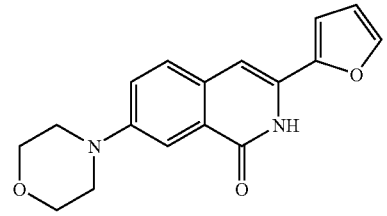

[Formula 191]

The above compound was synthesized by a method similar to that of Example 97, using the 5-chloro-2, N,N-trimethylbenzamide prepared in Step A of Example 80 as a starting material.

$^1$H-NMR (270 MHz, DMSO-d$_6$) δ (ppm): 3.22 (4H, t, J=4.6 Hz), 3.77 (4H, t, J=4.6 Hz), 6.62-6.65 (1H, m), 6.88 (1H, s), 7.27 (1H, d, J=3.5 Hz), 7.45-7.64 (2H, m), 7.80 (1H, s), 11.38 (1H, brs)
ESI (LC-MS positive mode) m/z 297 (M+H).

Example 163

7-Morpholin-4-yl-3-pyridin-4-ylisoquinolin-1-one ditrifluoroacetate

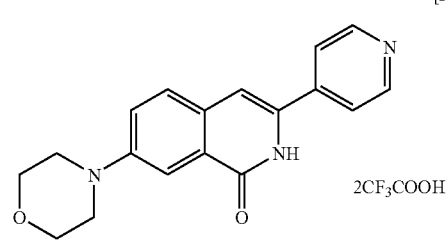

[Formula 192]

The above compound was synthesized by a method similar to that of Example 97, using the 5-chloro-2, N,N-trimethylbenzamide prepared in Step A of Example 80 as a starting material.

$^1$H-NMR (270 MHz, DMSO-d$_6$) δ (ppm): 3.28 (4H, t, J=4.8 Hz), 3.77 (4H, t, J=4.8 Hz), 7.37 (1H, s), 7.51-7.58 (2H, m), 7.69 (1H, d, J=8.7 Hz), 8.10 (2H, d, J=5.4 Hz), 8.78 (2H, d, J=5.4 Hz), 11.60 (1H, brs)
ESI (LC-MS positive mode) m/z 308 (M+H−2TFA).

Example B-1

Test Example 1

[Measurement of Cell Growth Inhibitory Activity]

Several representative examples of the compound group of the present invention were measured in terms of cell growth inhibitory activity.

Cancer cell growth inhibitory activity was measured using Cell Counting Kit-8 manufactured by Dojindo Laboratories. The human colon cancer cell line HCT116 obtained from American Type Culture Collection (Virginia, U.S.A) was inoculated in a 96-well culture plate at a concentration of 2,000 cells/well. Thereafter, a certain concentration of compound was added thereto, and the obtained mixture was then cultured at 37° C. in 5% $CO_2$ for 4 days. On the $4^{th}$ day of the culture, a Cell Counting Kit-8 solution was added to the culture product, and absorbance (measurement wavelength: 450 nm; reference wavelength: 615 nm) was measured in accordance with protocols included with the kit. Thereafter, 50% growth inhibitory concentration (IC50) was calculated.

The results are shown in Table 6.

TABLE 6

| Compound No. | Cell growth inhibitory activity (HCT116) IC50 (μM) |
|---|---|
| 8 | 0.028 |
| 10 | 0.097 |
| 21 | 0.02 |
| 29 | 0.052 |
| 36 | 0.018 |
| 41B | 0.034 |
| 43B | 0.024 |
| 61 | 0.021 |

Test Example 2

[Measurement of Antitumor Effect]

A representative example of the compound group of the present invention was measured in terms of antitumor effect.

Such antitumor effect was examined, using a tumor-bearing mouse produced by transplanting the human colon cancer cell line HCT116 obtained from American Type Culture Collection (Virginia, U.S.A) into the inguinal subcutis of a BALB/c nude mouse purchased from Charles River Laboratories Japan, Inc. The purchased nude mouse was quarantined for 1 week. Thereafter, approximately $5 \times 10^6$ HCT116 cells were transplanted subcutaneously. When the size of a tumor thereof became about 200 $mm^3$, the mouse was subjected to the present experiment.

Each compound was dissolved or suspended in a solution to be administered, and 0.5 ml of the solution was orally administered. Such administration was carried out twice in total, that is, on the initiation date of administration and 3 days after the administration. The antitumor effect was calculated as a tumor growth inhibition by comparing the solution administration group with a control group in terms of tumor growth.

Tumor growth inhibition(TGI)=(1−the tumor growth amount of agent-treated group/the tumor growth amount of control group)×100(%)

The results are shown in Table 7.

TABLE 7

| | Antitumor effect | |
| Compound No. | Dose (mg/kg) | TGI (%) on day 7 |
|---|---|---|
| 8 | 12.5 | 96 |
| 10 | 50 | 91 |
| 61 | 200 | 73 |

The invention claimed is:
1. A compound represented by the following formula (I):

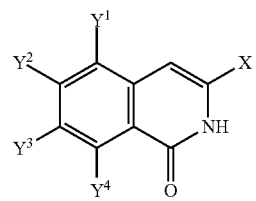

(1)

wherein,
$Y^1$ and $Y^4$ are independently selected from a hydrogen atom and a halogen atom,
either one of $Y^2$ and $Y^3$ represents $-NR^1R^2$, and the other represents a hydrogen atom or a halogen atom;
X represents an aryl group or a heteroaryl group, and the aryl group or heteroaryl group may be substituted with one or more substituents selected from Group A;
Group A consists of a $C_{1-8}$ alkyl group (wherein the alkyl group may be substituted with one or more substituents selected from a halogen atom, an aryl group, a heteroaryl group, $-OR^{11}$, and $-NR^{12}R^{13}$), a $C_{2-7}$ alkenyl group (wherein the $C_{2-7}$ alkenyl group may be substituted with one or more substituents selected from a halogen atom, a $C_{1-8}$ alkyl group, an aryl $C_{1-6}$ alkyl group, an aryl group, and a heteroaryl group), a $C_{2-7}$ alkynyl group (wherein the $C_{2-7}$ alkynyl group may be substituted with one or more substituents selected from a halogen atom, a $C_{1-8}$ alkyl group, an aryl $C_{1-6}$ alkyl group, an aryl group, and a heteroaryl group), a halogen atom, a hydroxyl group, an aryl group, a heteroaryl group, a cyano group, an amino group (wherein the nitrogen atom of the amino group may be substituted with one or two substituents selected from a $C_{1-8}$ alkyl group, which may be substituted with $-OR^{11}$ or $-NR^{12}R^{13}$, an aryl group, an aryl $C_{1-6}$ alkyl group, and a heteroaryl group), $-S(O)_nR^{14}$ (wherein n represents an integer between 0 and 2), a $C_{1-6}$ alkoxy group (wherein the alkoxy group may be substituted with one or more groups selected from an aryl group, a heteroaryl group, $-OR^{11}$, $-NR^{12}R^{13}$, and a halogen atom), a 4- to 7-membered hetero ring group (wherein the hetero ring group may be substituted with one or more substituents selected from Group D), an aryloxy group, a heteroaryloxy group, and a $C_{2-6}$ alkylenedioxy group; wherein $R^{11}$, $R^{12}$, $R^{13}$, and $R^{14}$ are independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an amino group, a $C_{1-6}$ alkylamino group, a di($C_{1-6}$ alkyl) amino group, an aryl group, and a heteroaryl group), an aryl group, and a heteroaryl group; or $R^{12}$ and $R^{13}$, together with nitrogen to which they are bonded, may form a 4- to 7-membered hetero ring containing at least one nitrogen atom;

$R^1$ represents a hydrogen atom, or a $C_{1-8}$ alkyl group that may be substituted with one or more substituents selected from Group B;

$R^2$ represents a $C_{1-8}$ alkyl group substituted with one or more substituents selected from Group B; or $R^2$ represents —COOR$^3$, —COR$^4$, —COSR$^5$, —CONR$^6$R$^7$, —NR$^{22}$R$^{23}$, —N=CR$^{24}$R$^{25}$; or $R^1$ and $R^2$, together with a nitrogen atom to which they are bonded, may form a 4- to 10-membered hetero ring containing at least one nitrogen atom (wherein the hetero ring may be substituted with one or more substituents selected from Group C); wherein $R^3$ represents a hydrogen atom, a $C_{1-8}$ alkyl group, a $C_{2-7}$ alkenyl group, a $C_{2-7}$ alkynyl group (wherein the alkyl group, alkenyl group, and alkynyl group may be substituted with one or more substituents selected from a halogen atom, a hydroxyl group, a $C_{1-6}$ alkoxy group (wherein the alkoxy group may be substituted with one or more substituents selected from a hydroxyl group, a $C_{1-6}$ alkoxy group, and a phenyl group), a $C_{3-8}$ cycloalkyl group, an aryl group, and a heteroaryl group), a $C_{3-8}$ cycloalkyl group, an aryl group, or a heteroaryl group;

$R^4$ is selected from a hydrogen atom, a $C_{1-8}$ alkyl group that is substituted with one or more $R^{20}$s, 1-naphthyl group, 2-naphthyl group, and a heteroaryl group;

$R^5$ is selected from a hydrogen atom, a $C_{1-8}$ alkyl group, an aryl group, and a heteroaryl group;

$R^{20}$ represents a hydroxyl group, a halogen atom, an aryl group, a heteroaryl group, a $C_{1-6}$ alkoxy group (wherein the alkoxy group may be substituted with one or more substituents selected from a halogen atom, an aryl group, and a heteroaryl group), an aryloxy group, a heteroaryloxy group, an amino group (wherein the nitrogen atom of the amino group may be substituted with one or two substituents selected from a $C_{1-8}$ alkyl group, an aryl group, an aryl $C_{1-6}$ alkyl group, a heteroaryl group, and —COOR$^{21}$), or a 4- to 7-membered hetero ring group containing at least one nitrogen atom (wherein the hetero ring group may be substituted with a $C_{1-8}$ alkyl group);

$R^{21}$ represents a $C_{1-8}$ alkyl group, an aryl $C_{1-6}$ alkyl group, or an aryl group;

$R^6$ and $R^7$ are independently selected from a hydrogen atom, a $C_{1-8}$ alkyl group, an aryl group, and a heteroaryl group;

$R^{22}$ and $R^{23}$ are independently selected from a hydrogen atom, a $C_{1-8}$ alkyl group, an aryl group, and a heteroaryl group;

$R^{24}$ and $R^{25}$ are independently selected from a hydrogen atom, a $C_{1-8}$ alkyl group, an aryl group, and a heteroaryl group;

Group B consists of a halogen atom, a $C_{1-6}$ alkylcarbonyl group, a $C_{1-6}$ alkylaminocarbonyl group, a $C_{1-6}$alkoxycarbonyl group, an aryl group (wherein the aryl group may be substituted with one or more substituents selected from a halogen atom, a $C_{1-8}$ alkyl group, a $C_{1-8}$ haloalkyl group, a hydroxyl group, a $C_{1-6}$ alkoxy group, and a $C_{1-6}$ haloalkoxy group), a heteroaryl group, —OR$^{31}$, and —NR$^{32}$R$^{33}$; wherein $R^{31}$, $R^{32}$, and $R^{33}$ are independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an aryl group, an amino group, a $C_{1-6}$ alkylamino group, and a di($C_{1-6}$ alkyl)amino group), an aryl group, a heteroaryl group, and —COOR$^{34}$; wherein $R^{34}$ represents a $C_{1-8}$ alkyl group, an aryl $C_{1-6}$ alkyl group, or an aryl group; or $R^{32}$ and $R^{33}$, together with a nitrogen atom to which they are bonded, may form a 4- to 7-membered hetero ring containing at least one nitrogen atom (wherein the hetero ring group may be substituted with one or more groups selected from Group D);

Group C consists of an aryl group, a heteroaryl group, a $C_{1-6}$ alkylcarbonyl group, a $C_{1-6}$ alkylaminocarbonyl group, a $C_{1-6}$ alkoxycarbonyl group, a hydroxyl group, a $C_{1-8}$ alkyl group, a $C_{1-6}$ alkoxy group (wherein the alkyl group and alkoxy group may be substituted with one or more substituents selected from a halogen atom, an aryl group, a heteroaryl group, —NR$^{41}$R$^{42}$, and —OR$^{43}$), an aryloxy group, and a heteroaryloxy group; wherein $R^{41}$, $R^{42}$, and $R^{43}$ are independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an amino group, a $C_{1-6}$ alkylamino group, and a di($C_{1-6}$ alkyl)amino group), an aryl $C_{1-6}$ alkyl group, an aryl group, and a heteroaryl group; or $R^{41}$ and $R^{42}$, together with a nitrogen atom to which they are bonded, may form a 4- to 7-membered hetero ring containing at least one nitrogen atom; and Group D consists of a halogen atom, an aryl group, a heteroaryl group, an aryloxy group, a heteroaryloxy group, an amino group (wherein the nitrogen atom of the amino group may be substituted with one or two substituents selected from a $C_{1-8}$ alkyl group, a hydroxy $C_{1-6}$ alkyl group, a $C_{1-6}$ alkoxy $C_{1-6}$ alkyl group, a $C_{1-6}$ alkylamino $C_{1-6}$ alkyl group, a di($C_{1-6}$ alkyl)amino $C_{1-6}$ alkyl group, an aryl group, an aryl $C_{1-6}$alkyl group, and a heteroaryl group), a hydroxyl group, a $C_{1-6}$ alkoxy group (wherein the alkoxy group may be substituted with one or more substituents selected from a halogen atom, a hydroxyl group, a $C_{1-6}$ alkoxy group, a $C_{1-6}$ alkylamino group, and di($C_{1-6}$ alkyl)amino group), a $C_{1-6}$ alkoxycarbonyl group, a $C_{1-8}$ alkyl group (wherein the alkyl group may be substituted with one or more substituents selected from a halogen atom, a hydroxyl group, a $C_{1-6}$ alkoxy group, a $C_{1-6}$ alkoxycarbonyl group, an amino group, an aryl group, a heteroaryl group, a $C_{1-6}$ alkylamino group, and a di($C_{1-6}$ alkyl) amino group;

or a pharmaceutically acceptable salt of said compound.

2. The compound, or pharmaceutically acceptable salt thereof according to claim 1, wherein $Y^3$ represents —NR$^1$R$^2$.

3. The compound, or pharmaceutically acceptable salt thereof according to claim 1, wherein $Y^1$, $Y^2$, and $Y^4$ represent a hydrogen atom;

$Y^3$ represents —NR$^1$R$^2$;

X represents an aryl group or a heteroaryl group, and the aryl group may be substituted with one or more substituents selected from Group A;

Group A consists of a $C_{1-8}$ alkyl group (wherein the alkyl group may be substituted with one or more substituents selected from a halogen atom and —NR$^{12}$R$^{13}$) a halogen atom, a hydroxyl group, an aryl group, an amino group (wherein the nitrogen atom of the amino group may be substituted with one or two substituents selected from a $C_{1-8}$ alkyl group and an aryl group), —SR$^{14}$, a $C_{1-6}$ alkoxy group (wherein the alkoxy group may be substituted with one or more groups selected from —OR$^{11}$ and a halogen atom), and a 4- to 7-membered hetero ring group (wherein the nitrogen atom of the hetero ring group may be substituted with one or two substituents selected from a $C_{1-8}$ alkyl group and a $C_{1-6}$ alkoxycarbonyl group); wherein $R^{11}$, $R^{12}$, $R^{13}$, and $R^{14}$ are independently selected from a hydrogen atom, a $C_{1-8}$ alkyl group, and an aryl group; or $R^{12}$ and $R^{13}$, together with nitrogen to which they are bonded, may form a 4- to 7-membered hetero ring containing at least one nitrogen atom;

$R^1$ represents a hydrogen atom, or a $C_{1-8}$ alkyl group that may be substituted with one or more substituents selected from Group B;

$R^2$ represents a $C_{1-8}$ alkyl group substituted with one or more substituents selected from Group B, —COOR$^3$, —COR$^4$, —COSR$^5$, —CONR$^6$R$^7$, —NR$^{22}$R$^{23}$, or —N=CR$^{24}$R$^{25}$; or $R^1$ and $R^2$, together with a nitrogen atom to which they are bonded, may form a 4- to 10-membered hetero ring containing at least one nitrogen atom (wherein the hetero ring may be substituted with one or more substituents selected from Group C); wherein $R^3$ represents a $C_{1-8}$ alkyl group (wherein the alkyl group may be substituted with one or more substituents selected from a halogen atom, a hydroxyl group, a $C_{1-6}$alkoxy group (wherein the alkoxy group may be substituted with one or more substituents selected from a hydroxyl group, a $C_{1-6}$ alkoxy group, and a phenyl group), a $C_{3-8}$ cycloalkyl group, an aryl group, and a heteroaryl group), a $C_{2-7}$ alkenyl group, a $C_{2-7}$ alkynyl group, a $C_{3-8}$ cycloalkyl group, an aryl group, or a heteroaryl group;

$R^4$ is selected from a hydrogen atom, a $C_{1-8}$ alkyl group that is substituted with one or more $R^{20}$s, 1-naphthyl group, 2-naphthyl group, and a heteroaryl group, and $R^5$ is selected from a $C_{1-8}$ alkyl group and an aryl group;

$R^{20}$ represents a hydroxyl group, a halogen atom, an aryl group, a heteroaryl group, a $C_{1-6}$ alkoxy group, an aryloxy group, an aryl $C_{1-6}$ alkoxy group, an amino group (wherein the nitrogen atom of the amino group may be substituted with one or two substituents selected from a $C_{1-8}$ alkyl group, an aryl group, and —COOR$^{21}$), or a 4- to 7-membered hetero ring group containing at least one nitrogen atom (wherein the hetero ring group may be substituted with a $C_{1-8}$ alkyl group);

$R^{21}$ represents a $C_{1-8}$ alkyl group, an aryl $C_{1-6}$ alkyl group, or an aryl group;

$R^6$ and $R^7$ are independently selected from a hydrogen atom, a $C_{1-8}$ alkyl group, and an aryl group;

$R^{22}$, $R^{23}$, $R^{24}$, and $R^{25}$ are independently selected from a hydrogen atom, a $C_{1-8}$ alkyl group, an aryl group, and a heteroaryl group;

Group B consists of a halogen atom, a $C_{1-6}$ alkoxycarbonyl group, an aryl group, —OR$^{31}$, and —NR$^{32}$R$^{33}$; wherein $R^{31}$, $R^{32}$, and $R^{33}$ are independently selected from a hydrogen atom, a $C_{1-8}$ alkyl group, an aryl $C_{1-6}$ alkyl group, an aryl group, a heteroaryl group, and —COOR$^{34}$; wherein $R^{34}$ represents a $C_{1-8}$ alkyl group, an aryl $C_{1-6}$ alkyl group, or an aryl group; or $R^{32}$ and $R^{33}$, together with a nitrogen atom to which they are bonded, may form a 4- to 7-membered hetero ring containing at least one nitrogen atom; and Group C consists of a $C_{1-6}$alkoxycarbonyl group, a hydroxyl group, a $C_{1-8}$ alkyl group, an aryl $C_{1-6}$ alkoxy $C_{1-8}$ alkyl group, a hydroxy $C_{1-8}$ alkyl group, an aryloxy group, and a heteroaryloxy group.

4. The compound, or pharmaceutically acceptable salt thereof according to claim 1, wherein $R^1$ and $R^2$, together with a nitrogen atom to which they are bonded, form a 4- to 10-membered hetero ring containing at least one nitrogen atom, wherein the hetero ring may have a substituent selected from Group C.

5. The compound, or pharmaceutically acceptable salt thereof according to claim 1, wherein $Y^2$ or $Y^3$ represents a morpholinyl group, an azetidinyl group, a pyrrolidinyl group, or piperidinyl group, and the hetero ring group may be substituted with one or more substituents selected from a hydroxyl group and a hydroxy $C_{1-6}$ alkyl group.

6. The compound, or pharmaceutically acceptable salt thereof according to claim 1, wherein $Y^2$ or $Y^3$ represents a morpholinyl group, an azetidinyl group, a pyrrolidinyl group, a 3-hydroxypyrrolidinyl group, a 2-hydroxymethylpyrrolidinyl group, a 3-hydroxymethylpyrrolidinyl group, a piperidinyl group, a 3-hydroxypiperidinyl group, a 4-hydroxypiperidinyl group, a 2-hydroxymethylpiperidinyl group, a 3-hydroxymethylpiperidinyl group, a 4-hydroxymethylpiperidinyl group, or a 4-hydroxy-4-hydroxymethylpiperidinyl group.

7. The compound, or pharmaceutically acceptable salt thereof according to claim 1, wherein
$R^1$ represents a hydrogen atom or a $C_{1-8}$ alkyl group (wherein the alkyl group may be substituted with one or more substituents selected from Group B); and
$R^2$ represents a $C_{1-8}$ alkyl group substituted with one or more substituents selected from Group B, —COOR$^3$, or —COCH$_2$NHCOOR$^{21}$.

8. The compound, or pharmaceutically acceptable salt thereof according to claim 1, wherein
$R^1$ represents a hydrogen atom; and
$R^2$ represents —COOR$^3$, —COSR$^5$, —CONR$^6$R$^7$, or —COR$^4$.

9. The compound, or pharmaceutically acceptable salt thereof according to claim 1, wherein $R^2$ represents —COOR$^3$.

10. The compound, or pharmaceutically acceptable salt thereof according to claim 9, wherein $R^3$ represents a $C_{1-8}$ alkyl group, a $C_{2-7}$ alkenyl group, or a $C_{2-7}$ alkynyl group (wherein the alkyl group, alkenyl group, and alkynyl group may be substituted with one or more substituents selected from a halogen atom, a hydroxyl group, or a $C_{1-6}$ alkoxy group (wherein the alkoxy group may be substituted with one or more substituents selected from a hydroxyl group, a $C_{1-6}$ alkoxy group, and a phenyl group)).

11. The compound, or pharmaceutically acceptable salt thereof according to claim 10, wherein $R^3$ represents a $C_{1-8}$ alkyl group that is substituted with one or more hydroxyl groups, a $C_{2-7}$ alkenyl group that is substituted with one or more hydroxyl groups, or a $C_{2-7}$ alkynyl group that is substituted with one or more hydroxyl groups.

12. The compound, or pharmaceutically acceptable salt thereof according to claim 11, wherein $R^3$ represents a $C_{1-6}$ alkyl group that is substituted with one or more hydroxyl groups.

13. The compound, or pharmaceutically acceptable salt thereof according to claim 1, wherein $Y^2$ or $Y^3$ represents a bis(hydroxy $C_{1-6}$ alkyl)amino group, a methyl(hydroxy $C_{1-6}$alkyl)amino group, a hydroxy $C_{1-6}$ alkylamino group, a methyl(morpholinyl $C_{1-6}$ alkyl)amino group, an amino $C_{1-6}$ alkylamino group, a $C_{1-6}$alkoxycarbonylamino group, or a hydroxy $C_{1-6}$ alkoxycarbonylamino group.

14. The compound, or pharmaceutically acceptable salt thereof according to claim 1, wherein $Y^2$ or $Y^3$ represents a bis(2-hydroxyethyl)amino group, a methyl(2-hydroxyethyl)

amino group, a 2-hydroxyethylamino group, a methyl(2-morpholin-4-ylethyl)amino group, a methyl(2-aminoethyl)amino group, or a 2-hydroxyethyloxycarbonylamino group.

15. The compound, or pharmaceutically acceptable salt thereof according to claim 1, wherein X represents a phenyl group or a heteroaryl group, and the phenyl group or heteroaryl group may be substituted with one or more substituents selected from Group A.

16. The compound, or pharmaceutically acceptable salt thereof according to claim 1, wherein X represents a phenyl group, and the phenyl group may be substituted with one or more substituents selected from Group A.

17. The compound, or pharmaceutically acceptable salt thereof according to claim 1, wherein
X represents a phenyl group or a heteroaryl group, and the phenyl group or heteroaryl group may be substituted with one or more substituents selected from Group A; and
Group A consists of a $C_{1-8}$ alkyl group that is substituted with one or more halogen atoms, an aryl group, a $C_{1-6}$ alkylthio group, a di($C_{1-6}$ alkyl)amino group, a 4- to 7-membered hetero ring group containing at least one nitrogen atom, a $C_{1-8}$ alkyl group, a $C_{2-7}$ alkenyl group, a $C_{2-7}$ alkynyl group, a $C_{1-6}$ alkoxy group (wherein the alkoxy group may be substituted with one or more halogen atoms), and a hydroxyl group.

18. The compound, or pharmaceutically acceptable salt thereof according to claim 1, wherein X represents a phenyl group, and the phenyl group may be substituted with one or more substituents selected from an ethyl group, a trifluoromethyl group, a trifluoromethoxy group, a methylthio group, a methoxy group, a chloro group, a phenyl group, a dimethylamino group, a morpholinyl group, a piperidinyl group, and a pyrrolidinyl group.

19. A compound represented by the following formula IV:

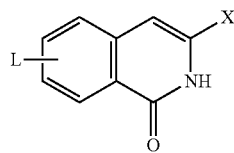

wherein X represents a phenyl group or a heteroaryl group, and the phenyl group or heteroaryl group may be substituted with one or more substituents selected from Group A; and L represents a fluorine atom, a bromine atom, or an iodine atom that is bonded to the 6- or 7-position on an isoquinolone ring;
Group A consists of a $C_{1-8}$ alkyl group (wherein the alkyl group may be substituted with one or more substituents selected from a halogen atom, an aryl group, a heteroaryl group, —$OR^{11}$, and —$NR^{12}R^{13}$), a $C_{2-7}$ alkenyl (wherein the $C_{2-7}$ alkenyl group may be substituted with one or more substituents selected from a halogen atom, a $C_{1-8}$ alkyl group, an aryl $C_{1-6}$ alkyl group, an aryl group, and a heteroaryl group), a $C_{2-7}$ alkynyl group (wherein the $C_{2-7}$ alkynyl group may be substituted with one or more substituents selected from a halogen atom, a $C_{1-8}$ alkyl group, an aryl $C_{1-6}$ alkyl group, an aryl group, and a heteroaryl group), a halogen atom, a hydroxyl group, an aryl group, a heteroaryl group, a cyano group, an amino group (wherein the nitrogen atom of the amino group may be substituted with one or two substituents selected from a $C_{1-8}$ alkyl group, which may be substituted with —$OR^{11}$ or —$NR^{12}R^{13}$, an aryl group, an aryl $C_{1-6}$ alkyl group, and a heteroaryl group), —$S(O)_nR^{14}$ (wherein n represents the integer between 0 and 2), a $C_{1-6}$ alkoxy group (wherein the alkoxy group may be substituted with one or more groups selected from an aryl group, a heteroaryl group, —$OR^{11}$, —$NR^{12}R^{13}$, and a halogen atom), a 4-to 7-membered hetero ring group (wherein the hetero ring group may be substituted with one or more substituents selected from Group D), an aryloxy group, a heteroaryloxy group, and a $C_{1-6}$ alkylenedioxy group; wherein $R^{11}$, $R^{12}$, $R^{13}$, and $R^{14}$ are independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an amino group, a $C_{1-6}$ alkylamino group, a di($C_{1-6}$alkyl)amino group, an aryl group, and a heteroaryl group), an aryl group, and a heteroaryl group; or $R^{12}$ and $R^{13}$, together with nitrogen to which they are bonded, may form a 4- to 7-membered hetero ring containing at least one nitrogen atom;
Group D consists of a halogen atom, an aryl group, a heteroaryl group, an aryloxy group, a heteroaryloxy group, an amino group (wherein the nitrogen atom of the amino group may be substituted with one or two substituents selected from a $C_{1-8}$ alkyl group, a hydroxyl $C_{1-6}$ alkyl group, a $C_{1-6}$ alkoxy $C_{1-6}$ alkyl group, a $C_{1-6}$ alkylamino $C_{1-6}$ alkyl group, a di($C_{1-6}$alkyl)amino $C_{1-6}$ alkyl group, an aryl group, an aryl $C_{1-6}$ alkyl group, and a heteroaryl group), a hydroxyl group, a $C_{1-6}$ alkoxy group (wherein the alkoxy group may be substituted with one or more substituents selected from a halogen atom, a hydroxyl group, a $C_{1-6}$ alkoxy group, a $C_{1-6}$ alkylamino group, and di($C_{1-6}$alkyl)amino group), a $C_{1-6}$ alkoxycarbonyl group, a $C_{1-8}$ alkyl group (wherein the alkyl group may be substituted with one or more substituents selected from a halogen atom, a hydroxyl group, a $C_{1-6}$ alkoxy group, a $C_{1-6}$ alkoxycarbonyl group, an amino group, an aryl group, a heteroaryl group, a $C_{1-6}$ alkylamino group, and a di($C_{1-6}$alkyl) amino group.

20. A method for producing the compound according to claim 1, which comprises amination of a compound represented by the following formula IV:

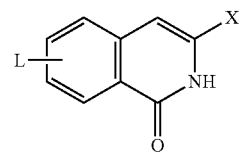

wherein X represents a phenyl group or a heteroaryl group, and the phenyl group or heteroaryl group may be substituted with one or more substituents selected from Group A; and L represents a fluorine atom, a bromine atom, or an iodine atom that is bonded to the 6- or 7-position on an isoquinolone ring;
Group A consists of a $C_{1-8}$ alkyl group (wherein the alkyl group may be substituted with one or more substituents selected from a halogen atom, an aryl group, a heteroaryl group, —$OR^{11}$, and —$NR^{12}R^{13}$), a $C_{2-7}$ alkenyl (wherein the $C_{2-7}$ alkenyl group may be substituted with one or more substituents selected from a halogen atom, a $C_{1-8}$ alkyl group, an aryl $C_{1-6}$ alkyl group, an aryl group, and a heteroaryl group), a $C_{2-7}$ alkynyl group (wherein the $C_{2-7}$ alkynyl group may be substituted with one or more substituents selected from a halogen atom, a $C_{1-8}$ alkyl group, an aryl $C_{1-6}$ alkyl group, an aryl group, and a heteroaryl group), a halogen atom, a hydroxyl group, an aryl group, a heteroaryl group, a cyano group, an amino group (wherein the nitrogen atom of the amino group may be substituted with one or two substituents selected from a $C_{1-8}$ alkyl group, which may be substituted with one or two substituents selected from a $C_{1-8}$ alkyl group, which may be substituted with $-OR^{11}$, $-NR^{12}R^{13}$, an aryl group, an aryl $C_{1-6}$ alkyl group, and a heteroaryl group), $-S(O)_n R^{14}$ (wherein n represents the integer between 0 and 2), a $C_{1-6}$ alkoxy group (wherein the alkoxy group may be substituted with one or more groups selected from an aryl group, a heteroaryl group, $-OR^{11}$, $-NR^{12}R^{13}$, and a halogen atom), a 4-to 7-membered hetero ring group (wherein the hetero ring group may be substituted with one or more substituents selected from Group D), an aryloxy group, a heteroaryloxy group, and a $C_{1-6}$ alkylendioxy group; wherein $R^{11}$, $R^{12}$, $R^{13}$, and $R^{14}$ are independently selected from a hydrogen atom, a $C_{1-8}$ alkyl group (wherein the alkyl group may be substituted with one or more substituents selected from a halogen atom, a hydroxyl group, a $C_{1-6}$ alkoxy group, an amino group, a $C_{1-6}$ alkylamino group, a di($C_{1-6}$alkyl)amino group, an aryl group, and a heteroaryl group), an aryl group, and a heteroaryl group; or $R^{12}$ and $R^{13}$, together with nitrogen to which they are bonded, may form a 4- to 7-membered hetero ring containing at least one nitrogen atom; Group D consists of a halogen atom, an aryl group, a heteroaryl group, an aryloxy group, a heteroaryloxy group, an amino group (wherein the nitrogen atom of the amino group may be substituted with one or two substituents selected from a $C_{1-8}$ alkyl group, a hydroxyl $C_{1-6}$ alkyl group, a $C_{1-6}$ alkoxy $C_{1-6}$ alkyl group, a $C_{1-6}$ alkylamino $C_{1-6}$ alkyl group, a di($C_{1-6}$alkyl)amino $C_{1-6}$ alkyl group, an aryl group, an aryl $C_{1-6}$ alkyl group, and a heteroaryl group), a hydroxyl group, a $C_{1-6}$ alkoxy group (wherein the alkoxy group may be substituted with one or more substituents selected from a halogen atom, a hydroxyl group, a $C_{1-6}$ alkoxy group, a $C_{1-6}$ alkylamino group, and di($C_{1-6}$alkyl)amino group), a $C_{1-6}$ alkoxycarbonyl group, a $C_{1-8}$ alkyl group (wherein the alkyl group may be substituted with one or more substituents selected from a halogen atom, a hydroxyl group, a $C_{1-6}$ alkoxy group, a $C_{1-6}$ alkoxycarbonyl group, an amino group, an aryl group, a heteroaryl group, a $C_{1-6}$ alkylamino group, and a di($C_{1-6}$alkyl)amino group.

21. A pharmaceutical composition, which comprises, as an active ingredient, the compound, or pharmaceutically acceptable salt thereof according to claim 1.

* * * * *